US012778781B2

(12) United States Patent
Yoo et al.

(10) Patent No.: US 12,778,781 B2
(45) Date of Patent: Nov. 3, 2026

(54) ANKLE FOOT ORTHOSIS DEVICES AND PROCESSES FOR MAKING AND USING THE SAME

(71) Applicant: Protect3D, Inc., Durham, NC (US)

(72) Inventors: Jaeah Yoo, Durham, NC (US); Clark Harrison Bulleit, Tampa, FL (US); Kevin Andrew Gehsmann, Greensboro, NC (US); Timothy John Skapek, Dallas, TX (US); Brian Rock, Raleigh, NC (US)

(73) Assignee: PROTECT3D, INC., Durham, NC (US)

( * ) Notice: Subject to any disclaimer, the term of this patent is extended or adjusted under 35 U.S.C. 154(b) by 0 days.

(21) Appl. No.: 18/889,306

(22) Filed: Sep. 18, 2024

(65) Prior Publication Data

US 2025/0090358 A1 Mar. 20, 2025

Related U.S. Application Data

(60) Provisional application No. 63/583,565, filed on Sep. 18, 2023.

(51) Int. Cl.
*A61F 5/01* (2006.01)
*B29C 64/386* (2017.01)
(Continued)

(52) U.S. Cl.
CPC ............. *A61F 5/0111* (2013.01); *B33Y 80/00* (2014.12); *G16H 50/50* (2018.01); *B29C 64/386* (2017.08); *B33Y 50/00* (2014.12)

(58) Field of Classification Search
CPC .... A61F 5/0111; A61F 5/0127; A61F 5/0195; A63B 71/1225
(Continued)

(56) References Cited

U.S. PATENT DOCUMENTS

| | | | |
|---|---|---|---|
| 1,757,019 | A | 5/1930 | George |
| 1,837,499 | A | 12/1931 | Sparhawk |

(Continued)

FOREIGN PATENT DOCUMENTS

| | | | |
|---|---|---|---|
| CA | 140771 | A | 5/1912 |
| CA | 140771 | S | 4/2012 |

(Continued)

OTHER PUBLICATIONS

Anusci, Victor. "Activarmor May Have Finally Cracked the 3D Printed Cast/Orthosis Riddle." 3D Printing Media Network—The Pulse of the AM Industry, Mar. 19, 2018, https://www.3dprintingmedia.network/activarmor-may-finally-cracked-3d-printed-cast-orthosis-riddle/.

(Continued)

*Primary Examiner* — Keri J Nelson
*Assistant Examiner* — Seth R. Brown
(74) *Attorney, Agent, or Firm* — Husch Blackwell LLP; Bryan D. Stewart; Andrew C. Landsman

(57) ABSTRACT

The present disclosure relates to various embodiments of a patient-specific ankle-foot orthotic (AFO) and methods of producing the same. The AFO includes a body comprising an upper support member, a lower support member, and a footplate. The upper support member comprises a first outer surface and a first inner surface, the first inner surface designed to selectively engage with at least a portion of a patient's calf. The lower support member comprises a second outer surface and a second inner surface, the second inner surface designed to selectively engage with at least a portion of the patient's ankle. The footplate comprises a third outer surface and a third inner surface, the third inner surface designed to selectively engage with at least a portion of the patient's foot. The body includes one or more struc-
(Continued)

tural bands disposed on portions of the first outer surface, second outer surface, and third outer surface.

17 Claims, 46 Drawing Sheets

(51) Int. Cl.

| | |
|---|---|
| ***B33Y 50/00*** | (2015.01) |
| ***B33Y 80/00*** | (2015.01) |
| ***G16H 50/50*** | (2018.01) |

(58) Field of Classification Search
USPC .......................................................... 602/27
See application file for complete search history.

(56) References Cited

U.S. PATENT DOCUMENTS

| | | | | |
|---|---|---|---|---|
| 1,850,540 A | | 3/1932 | Erickson | |
| 2,247,961 A | | 7/1941 | Mulvey | |
| 2,377,339 A | | 6/1945 | Greene | |
| D181,676 S | | 12/1957 | Ristenpart | |
| D243,284 S | | 2/1977 | Myers | |
| D248,315 S | | 6/1978 | Blaisdell et al. | |
| D290,879 S | | 7/1987 | Giampapa et al. | |
| D310,278 S | | 8/1990 | Quinlan | |
| D310,721 S | | 9/1990 | Beisang, III | |
| 5,496,263 A | * | 3/1996 | Fuller | A61F 5/0127 602/23 |
| D382,052 S | | 8/1997 | Bayer | |
| 5,836,902 A | | 11/1998 | Gray | |
| D417,543 S | | 12/1999 | Gable | |
| D466,997 S | | 12/2002 | Edens et al. | |
| D472,312 S | | 3/2003 | Edens et al. | |
| 6,629,945 B1 | | 10/2003 | Stromgren | |
| D485,020 S | | 1/2004 | Yake et al. | |
| D486,231 S | | 2/2004 | Kielb et al. | |
| D554,386 S | | 11/2007 | Nobles et al. | |
| D555,254 S | | 11/2007 | Buethorn | |
| D569,044 S | | 5/2008 | Crye et al. | |
| D599,025 S | | 8/2009 | Mayhew | |
| D625,821 S | | 10/2010 | Goncalves et al. | |
| 8,272,073 B2 | | 9/2012 | Arensdorf et al. | |
| D669,228 S | | 10/2012 | Smith | |
| D698,924 S | | 2/2014 | Pieroni et al. | |
| D705,938 S | | 5/2014 | Mcdonald | |
| 8,838,263 B2 | | 9/2014 | Sivak et al. | |
| D716,958 S | | 11/2014 | Thomas et al. | |
| D724,746 S | | 3/2015 | Ruel et al. | |
| D730,132 S | | 5/2015 | Szanto | |
| D815,214 S | | 4/2018 | Lacy et al. | |
| D833,618 S | | 11/2018 | Ballsieper et al. | |
| D840,047 S | | 2/2019 | Koo et al. | |
| 10,231,862 B2 | | 3/2019 | Summit | |
| D847,350 S | | 4/2019 | Eaton | |
| D858,788 S | | 9/2019 | Giddings et al. | |
| D861,185 S | | 9/2019 | Pihlavamki et al. | |
| D863,577 S | | 10/2019 | Chobuathong | |
| D865,183 S | | 10/2019 | Otani | |
| D865,197 S | | 10/2019 | Godfrey | |
| D868,279 S | | 11/2019 | Chiu | |
| D876,640 S | | 2/2020 | King | |
| D882,808 S | | 4/2020 | Miller | |
| D885,589 S | | 5/2020 | Marcil | |
| 10,709,195 B2 | | 7/2020 | Li | |
| 10,758,396 B2 | | 9/2020 | Rivlin et al. | |
| D904,638 S | | 12/2020 | Shiota | |
| D908,905 S | | 1/2021 | Braden | |
| D908,906 S | | 1/2021 | Braden | |
| D908,910 S | | 1/2021 | Lampert | |
| D909,672 S | | 2/2021 | Williams | |
| 10,932,940 B2 | | 3/2021 | Karasahin | |
| 10,940,031 B2 | | 3/2021 | Mark | |
| D936,847 S | | 11/2021 | Bulleit et al. | |
| D942,617 S | | 2/2022 | Smith | |
| D951,467 S | | 5/2022 | Sonoda et al. | |
| D953,538 S | | 5/2022 | Onhintie | |
| D961,094 S | | 8/2022 | Gehsmann et al. | |
| D961,215 S | | 8/2022 | Qin et al. | |
| D983,381 S | | 4/2023 | Bulleit et al. | |
| 11,694,002 B1 | | 7/2023 | Bulleit | |
| 11,882,888 B1 | | 1/2024 | Bulleit et al. | |
| 11,931,281 B1 | | 3/2024 | Bulleit et al. | |
| D1,060,678 S | | 2/2025 | Takahashi | |
| D1,063,069 S | | 2/2025 | Kim et al. | |
| 12,232,549 B1 | | 2/2025 | Bulleit et al. | |
| D1,065,553 S | | 3/2025 | Xie | |
| 2001/0027284 A1 | * | 10/2001 | Wellershaus | A61F 5/0111 602/23 |
| 2004/0236259 A1 | * | 11/2004 | Pressman | A61F 5/0111 602/27 |
| 2008/0243042 A1 | * | 10/2008 | Balzer | A61F 5/0111 602/27 |
| 2008/0294083 A1 | * | 11/2008 | Chang | A61F 5/0111 602/23 |
| 2010/0268138 A1 | | 10/2010 | Summit et al. | |
| 2014/0163664 A1 | | 6/2014 | Goldsmith | |
| 2014/0180185 A1 | | 6/2014 | Zachariasen | |
| 2014/0298681 A1 | | 10/2014 | Epstein | |
| 2014/0371648 A1 | * | 12/2014 | DeHeer | A61F 5/0125 602/27 |
| 2015/0328840 A1 | | 11/2015 | Zachariasen et al. | |
| 2016/0278845 A1 | | 9/2016 | Mayse | |
| 2017/0079830 A1 | | 3/2017 | Chhatrala | |
| 2019/0117432 A1 | | 4/2019 | Park | |
| 2019/0240057 A1 | * | 8/2019 | Gunnsteinsson | A61F 5/0111 |
| 2019/0269558 A1 | | 9/2019 | Sheehan | |
| 2020/0069454 A1 | | 3/2020 | Hall | |
| 2022/0079794 A1 | | 3/2022 | Johnson et al. | |
| 2022/0313467 A1 | * | 10/2022 | Ducharme | A61F 5/01 |
| 2022/0401245 A1 | * | 12/2022 | Johnson | A61F 5/0127 |
| 2024/0148086 A1 | | 5/2024 | Bulleit | |

FOREIGN PATENT DOCUMENTS

| | | |
|---|---|---|
| CN | 105342741 A | 2/2016 |
| CN | 205041591 U | 2/2016 |
| CN | 105434092 A | 3/2016 |
| CN | 105853038 A | 8/2016 |
| CN | 205612603 U | 10/2016 |
| CN | 106361487 A | 2/2017 |
| CN | 107280841 A | 10/2017 |
| CN | 105963061 B | 12/2017 |
| CN | 108938171 A | 12/2018 |
| CN | 110115652 A | 8/2019 |
| CN | 306074538 S | 9/2020 |
| CN | 114404123 | 4/2022 |
| EP | 3102162 B1 | 11/2021 |
| GB | 2580413 A1 | 7/2020 |
| WO | 2021156894 | 8/2021 |

OTHER PUBLICATIONS

Airwolf 3D. “Amphibianskin Offers an Affordable 3D Printed Splint to Help the Healing Process.” Airwolf 3D, Jan. 28, 2019, https://airwolf3d.com/2014/10/21/3d-printed-splint/.

Knowles, Kitty. “Castprint Is 3D Printing Beautiful Healthtech.” Sifted, Aug. 4, 2019, https://sifted.eu/articles/castprint-3d-printing-healthtech-startup-wise-guys-techchill-latvia.

Tan X, Chen W, Cao J, Ahmed-Kristensen S. Identify Critical Data During Product Customisation—A Case Study of Orthoses Fabrication. In Proceedings of the Design Society: Design Conference May 2020 (vol. 1, pp. 413-422). Cambridge University.

Amazon. Impact A/C Shoulder Pad—Right, Standard (Under 250lbs). Aug. 25, 2010. https://www.amazon.com/Impact-Shoulder-Pad-Standard-250lbs/dp/B0040UVTVA (Year: 2010).

Christensen, A. and Rybicki, F.J., 2017. Maintaining safety and efficacy for 3D printing in medicine. 3D printing in medicine, 3(1), pp. 1-10.

Hale L, Linley E, Kalaskar DM. A digital workflow for design and fabrication of bespoke orthoses using 3D scanning and 3D printing,

(56) References Cited

OTHER PUBLICATIONS a patient-based case study. Scientific reports. Apr. 27, 2020;10(1):1-7.
Impact A/C Shoulder Pad—Right, Standard (Under 250lbs), Impact, Amazon, [Post date: Aug. 25, 2010], [Site seen Nov. 22, 2021], Seen at URL: https ://www.amazon.com/Impact-Shoulder-Pad-Standard-2501 bs/dp/B0040 Uvtv A/ref=asc_df_B0040 UVTV A/ (Year: 2010).
Impact Deltoid Pad, Arthron Impact, Ithaca Sports, [Post date unknown], [Site seen Nov. 22, 2021] Seen at URL: https://www.ithacasports.com/deltpad.html?cmp=googleproducts&kw=deltpad&gclid=EAlalQobCh M Ig7be796i9 AIVxdzlCh0zaAS2EAQYBiABEg LqPP% E2%80%A6 (Year: 2021).
Kim H, Jeong S. Case study: Hybrid model for the customized wrist orthosis using 3D printing. Journal of mechanical science and technology. Dec. 2015;29(12):5151-6.
Instagram. protect3d. Oct. 27, 2020. https://www.instagram.com/protect3d/p/CG2w7bCnZ8k/?img_index=2 (Year: 2020).
Magic Silicone Shoulder Pads, Boom BA, getboomba.com, [Post date unknown], [Site seen Nov. 22, 2021], Seen at URL: https://www.getboomba.com/products/si l icone-shou lder -pads?cu rrency=US D&variant=39441729224880&utm_med i um =cpc&utm_ source=google&utm%E2%80%A6 (Year: 2021).
Revit Seeflex shoulder Protectors RV16, Revit, Revzilla.com, [Post date unknown], [Site seen Jul. 11, 2023], Seen at URL: https://www.revzilla.com/motorcycle/revit-seeflex-shoulder-protectors-rv16?sku_id=1129080 (Year: 2023).
Sharma N, Welker D, Cao S, Netzer BV, Honigmann p. Thieringer F. An Interactive, Fully Digital Design Workflow for a Custom 3D Printed Facial Protection Orthosis (Face Mask). In International Conference on Additive Manufacturing in Products and Applications Sep. 1, 2020 (pp. 26-36). Springer, Cham.
Vicenzino B, Collins N, Cleland J, McPoil T. A clinical prediction rule for identifying patients with patellofemoral pain who are likely to benefit from foot orthoses: a preliminary determination. British Journal of Sports Medicine. Sep. 1, 2010 ;44(12):862.
Wall Street Journal. How Two Duke Benchwarmers and a 3-D Printer Rescued a Top NFL Quarterback Prospect. Mar. 1, 2019. https://www.wsj.com/articles/how-two-duke-benchwarmers-and-a-3-d-printer-rescued-a-top-nfl-quarterback-prospecl-11551446283 (Year: 2019).
Garcia J, Yang Z, Mongrain R, Leask RL, Lachapelle K. 3D printing materials and their use in medical education: a review of current technology and trends for the future. BMJ simulation & technology enhanced learning. Jan. 2018 ;4 (1) :27.
Lin H, Shi L, Wang D. A rapid and intelligent designing technique for patient-specific and 3D-printed orthopedic cast. 3D printing in medicine. Dec. 2016;2(1):1-0.
NFL. NFL 2020 1st and Future Winner, Protect3d, using 3D scanning and printing to help improve injury recovery. Dec. 14, 2020. https://www .nfl.com/playerhealthandsafety/equipment-and-innovation/1 st-and-future/nfl-2020-1 st-and-future-winner-protect3d-using-3d-scanning-and-printing-to-help- (Year: 2020).

* cited by examiner

ANKLE FOOT ORTHOSIS DEVICES AND PROCESSES FOR MAKING AND USING THE SAME

CROSS-REFERENCE TO RELATED APPLICATIONS

This application claims the benefit of priority to U.S. Provisional Patent Application No. 63/583,565 filed Sep. 18, 2023, which is incorporated herein by reference in its entirety.

BACKGROUND

Ankle foot orthoses (AFOs) are externally-worn assistive devices that provide critical support for patients with a variety of foot, ankle, and gait issues. Such devices generally keep joints in proper alignment, stabilize gait, control the position and motion of the ankle, stabilize the lower limb, and compensate for muscle weakness. Common medical issues that can benefit from or be alleviated by the use of AFOs include, for example, sprains and fractures, arthritis pain, or foot drop (e.g., the inability to raise the foot on one side of the body, thereby causing the toes to dangle and drag on the ground while walking), among other issues.

However, generic AFOs may not be suited to individual anatomical, activity level, or comfort needs, which can result in suboptimal treatment and healing outcomes. Further, current custom-made AFOs may require lengthy and costly fabrication/manufacturing processes often requiring duplicative measuring, casting, and adjusting. Thus, current limitations with custom-made and off-the-shelf AFOs can hinder the overall effectiveness and functionality of the AFOs, and potentially lead to suboptimal outcomes for patients. Current methods of manufacturing (e.g., hand-molding) may be time-consuming and imprecise, which can delay treatment and healing.

As a result, there is a long-felt, but unsolved need for improved AFOs and methods of producing and using the same.

BRIEF SUMMARY OF THE DISCLOSURE

Briefly described, aspects of the present disclosure generally relate to patient-specific AFOs designed to provide support for lower leg issues, as well as processes for making and using the same.

According to a first aspect, the present disclosure relates to a patient-specific ankle-foot orthotic (AFO), the AFO comprising: a body comprising: an upper support member comprising: a first outer surface and a first inner surface, the first inner surface designed to selectively engage with at least a portion of a patient's calf; a lower support member comprising: a second outer surface and a second inner surface, the second inner surface designed to selectively engage with at least a portion of the patient's ankle; a footplate comprising: a third outer surface and a third inner surface, the third inner surface designed to selectively engage with at least a portion of the patient's foot; and one or more structural bands disposed on portions of the first outer surface, second outer surface, and third outer surface.

According to a second aspect, the patient-specific AFO of the first aspect or any other aspect, further comprising a baseline thickness of about 1.5 mm to 5.0 mm.

According to a third aspect, the patient-specific AFO of the second aspect or any other aspect, wherein the one or more structural bands include a width of about 1.0 mm to 10.0 mm and contribute to an added thickness of about 0.5 mm to 5.0 mm to the baseline thickness.

According to a fourth aspect, the patient-specific AFO of the third aspect or any other aspect, wherein the lower support member comprises one or more struts.

According to a fifth aspect, the patient-specific AFO of the fourth aspect or any other aspect, wherein each of the one or more struts is angled by about 10.0 degrees to 40.0 degrees from vertical.

According to a sixth aspect, the patient-specific AFO of the third aspect or any other aspect, wherein the upper support member includes one or more ventilation holes.

According to a seventh aspect, the patient-specific AFO of the third aspect or any other aspect, wherein the upper support member includes at least one attachment opening.

According to an eighth aspect, the patient-specific AFO of the seventh aspect or any other aspect, further comprising an anterior plate, the anterior plate comprising a fourth outer surface having at least one attachment slot and a fourth inner surface, the fourth inner surface designed to selectively engage with an anterior portion of the patient's lower leg.

According to a ninth aspect, the patient-specific AFO of the eighth aspect or any other aspect, further comprising at least one attachment member designed to selectively engage with the at least one attachment opening and the at least one attachment slot.

According to a tenth aspect, the patient-specific AFO of the third aspect or any other aspect, wherein the footplate comprises one or more raised walls.

According to an eleventh aspect, the patient-specific AFO of the third aspect or any other aspect, wherein the one or more structural bands are edge structural bands.

According to a twelfth aspect, the patient-specific AFO of the third aspect or any other aspect, wherein the one or more structural bands are peripheral structural bands.

According to a thirteenth aspect, the patient-specific AFO of the third aspect or any other aspect, wherein the one or more structural bands are crossing structural bands.

According to a fourteenth aspect, the patient-specific AFO of the third aspect or any other aspect, wherein the one or more structural bands are gait-oriented structural bands.

According to a thirteenth aspect, the patient-specific AFO of the eighth aspect or any other aspect, wherein the body and the anterior plate are additively manufactured.

The present disclosure also relates to a method of treating a lower leg condition for a patient comprising, the method comprising, according to a sixteenth aspect: receiving patient data; processing the received patient data to produce a 3D model of a patient lower leg; designing a 3D model of a patient-specific and pathology-specific AFO based on the 3D model of the patient lower leg; and additively manufacturing a patient-specific and pathology-specific AFO based on the 3D model of the patient-specific and pathology-specific AFO.

According to a seventeenth aspect, the method of the sixteenth aspect or any other aspect, wherein the step of receiving patient data further comprises: positioning the patient lower leg; and scanning a top portion of the patient foot.

According to an eighteenth aspect, the method of the seventeenth aspect or any other aspect, wherein the step of positioning the patient lower leg further comprises: resting the patient foot on a platform in a semi-weight-bearing position; and orienting a patient knee perpendicular to the patient foot.

According to a nineteenth aspect, the method of the eighteenth aspect or any other aspect, wherein the patient data further comprises height, weight, age, and activity level of the patient.

According to a twentieth aspect, the method of the nineteenth aspect or any other aspect, wherein the step of additively manufacturing a patient-specific and pathology-specific AFO based on the 3D model of the patient-specific and pathology-specific AFO further comprises: generating a file for 3D-printing the patient-specific and pathology-specific AFO; and instructing a 3D printer to print the patient-specific and pathology-specific AFO.

According to a twenty-first aspect, the method of the twentieth aspect or any other aspect, wherein the patient-specific and pathology-specific AFO comprises: an additively manufactured body comprising: an upper support member comprising: a first outer surface and a first inner surface, the first inner surface designed to selectively engage with a portion of a patient's calf; a lower support member comprising: a second outer surface and a second inner surface, the second inner surface designed to selectively engage with a portion of the patient's ankle; a footplate comprising: a third outer surface and a third inner surface, the third inner surface designed to selectively engage with a portion of the patient's foot; one or more structural bands disposed on portions of the first outer surface, second outer surface, and third outer surface; and a baseline thickness of about 1.5 mm to 5.0 mm, wherein the one or more structural bands include a width of about 1.0 mm to 10.0 mm and contribute to an added thickness of about 0.5 mm to 5.0 mm to the baseline thickness.

According to a twenty-second aspect, the method of the twenty-first aspect or any other aspect, wherein a dimension of the one or more structural bands is based on the received patient data.

The present disclosure also relates to a patient-specific AFO, the AFO comprising: an additively manufactured body comprising: an upper support member comprising: a first outer surface and a first inner surface, the first inner surface designed to selectively engage with a portion of a patient's calf; a lower support member comprising: a second outer surface and a second inner surface, the second inner surface designed to selectively engage with a portion of the patient's ankle; a footplate comprising: a third outer surface and a third inner surface, the third inner surface designed to selectively engage with a portion of the patient's foot; an anterior plate comprising: a fourth outer surface having at least one attachment slots and a fourth inner surface, the fourth inner surface designed to selectively engage with an anterior portion of the patient's lower leg; at least one attachment member designed to selectively engage with at least one of the one or more attachment openings and the at least one attachment slots to secure the AFO to the patient's lower leg; one or more structural bands disposed on portions of the first outer surface, second outer surface, and third outer surface; and a baseline thickness of about 1.5 mm to 5.0 mm, wherein the one or more structural bands include a width of about 1.0 mm to 10.0 mm and contribute to an added thickness of about 0.5 mm to 5.0 mm to the baseline thickness.

It will be understood by those skilled in the art that one or more aspects of this disclosure can meet certain objectives, while one or more other aspects can lead to certain other objectives. Various modifications to the illustrated embodiments will be readily apparent to those skilled in the art, and the generic principles herein can be applied to other embodiments and applications without departing from embodiments of the disclosure. Other objects, features, benefits, and advantages of the present disclosure will be apparent in this summary and descriptions of the disclosed embodiments, and will be readily apparent to those skilled in the art. Such objects, features, benefits, and advantages will be apparent from the above as taken in conjunction with the accompanying figures and all reasonable inferences to be drawn therefrom.

DETAILED DESCRIPTION

Figure 1B:
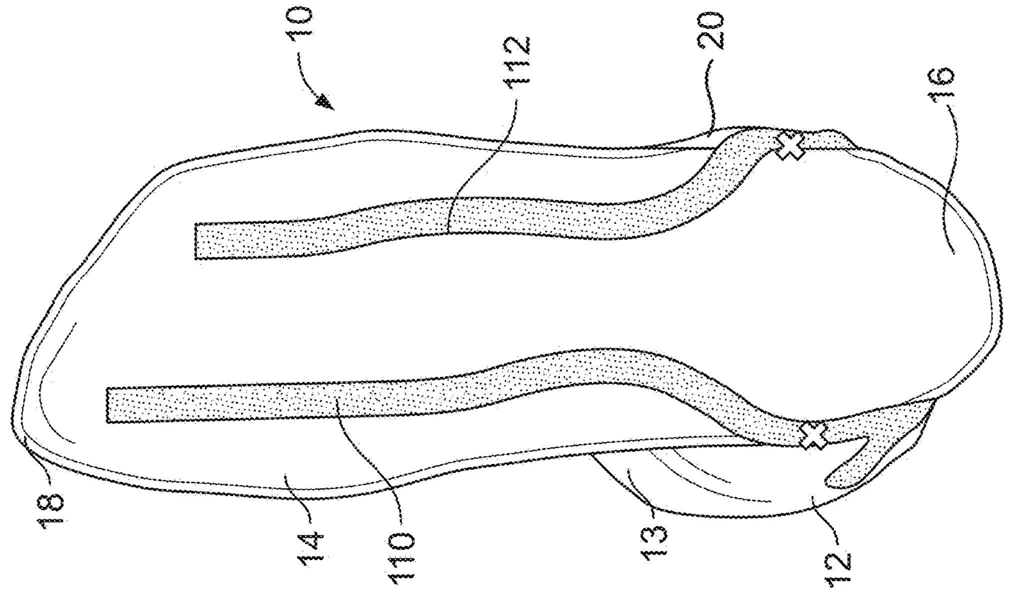
FIG. 1B is a bottom schematic view of the one or more structural bands of FIG. 1A.

Generally, a typical gait cycle (e.g., walking pattern) involves a stance phase and a swing phase for each leg. Whenever a stance phase ends and a swing phase begins, the ankle must dorsiflex for the toes to lift and avoid dragging against the ground. However, in the exemplary case of foot drop, injury to the peroneal nerve injury can affect one or more muscles in the foot that control dorsiflexion. Accordingly, it may be desirable to counteract the symptoms of foot drop (among other issues) by providing static dorsiflexion and varying levels of mediolateral ankle stability, thereby enabling the patient to assume a functional gait. One such treatment method involves use of AFOs, which can play a crucial role in assisting patients having various lower limb conditions (such as foot drop, among others) to regain mobility and stability.

Briefly described, aspects of the present disclosure generally relate to patient-specific AFOs designed to provide customized support for patients with lower leg issues and/or gait abnormalities, such as, but not limited to, foot drop, ankle sprains/fractures, ankle/hindfoot arthritis, posterior tibial tendon dysfunction (PTTD) or insufficiency (PTTI), or arch collapse. Thus, the AFOs can be used for more light to severe cases of foot and ankle ailments requiring varying levels of stability or immobilization.

In at least one embodiment, the AFOs include one or more customized and/or patient specific components that dynamically support and stabilize a portion of the lower leg to correct deformities, improve mobility, and promote healing in cases of injury or surgical treatment. In particular, the AFOs of this disclosure include components such as an upper support member designed to selectively engage with the patient's calf area, a lower support member (e.g., provided in the form of dual struts) designed to selectively engage with the patient's ankle area, and a footplate designed to selectively engage with at least a portion of a plantar surface of the patient's foot. In some cases, the upper support member can be designed to stabilize an upper portion of the lower leg. In other cases, the lower support member can be designed to flex and bend naturally at the ankle joint during gait. In yet other cases, the footplate can be designed to restrict plantarflexion while maintaining flexibility in the foot during gait. In certain embodiments, the AFOs can additionally include an anterior plate positioned at a front portion of the lower leg.

In some embodiments, the AFOs can include one or more attachment members designed to secure the AFOs to the patient's lower leg and ensure a secure and personalized fit. In some embodiments, one or more of the aforementioned components can be integrated as one body.

Further, in some embodiments—via 3D digital designing processes and additive manufacturing techniques—one or more components of the AFOs can include strategically varying reinforcement structures and thickness distributions mapped to certain areas of the lower leg. In particular, by varying the dimensions—including the thickness—of the bending area to accommodate the specific needs of a patient, the AFO can deliver a custom-tailored amount of energy return. Thus, the AFOs can provide a dynamic energy response through a patient's gait cycle while controlling the ankle foot complex.

According to certain embodiments, various materials and material properties can be optimized in order to improve the performance and life cycle of the AFOs. For instance, the material of the AFOs can be suitable for repeated cyclic loading related to routine use while providing desired rigidity/stiffness when the foot swings during gait. This can at least partially restrict dorsiflexion about the ankle joint, which can improve gait biomechanics for patients with certain lower leg issues. Exemplary materials include nylon (e.g., PA 12), molded plastic/plastic, thermoplastic/thermosetting plastic, carbon fiber, carbon composites, copolymer polypropylene, Ortholen, plaster and any other suitable materials. Any of the aforementioned materials may be beneficial for energy return at "toe-off" (e.g., efficient forward movement). Materials such as molded plastic can enable the AFOs to redistribute extension and ground reaction forces towards to the knee area, resulting in increased leverage. In some embodiments, the AFOs can comprise one or more materials in order to achieve patient-specific goals without departing from the principles of this disclosure.

Thus, custom or patient-specific AFOs such as those described herein can be particularly effective in assisting patients with various lower limb conditions in regaining mobility and stability while providing a low-profile treatment solution (e.g., a patient can comfortably wear an AFO within a shoe). As used herein, the term "patient-specific" can be used to describe a custom-made device or a component of a device for a particular patient. Patient-specific devices can be created using a variety of manufacturing techniques including, but not limited to, 3D printing, injection molding, or milling, amongst other techniques. Generally, such manufacturing techniques involve scanning patient anatomy to create a 3D rendering of the anatomy, creating a 3D model of a device designed to be specific to patient needs and anatomy, and manufacturing the device based on the 3D model. In some embodiments, one or more components of the AFOs can be at least partially additively manufactured according to patient-specific and/or pathology-specific design considerations. In alternative embodiments, one or more of the components of the AFOs can include more than one material composition.

The above features (and others) will be discussed herein in the context of an AFO. However, it will be understood that the concepts discussed here are applicable to any suitable orthotic used to support any human (or animal) anatomy without departing from the principles of this disclosure.

According to various embodiments, strategically varying material thicknesses and/or structural components can enable the AFOs to stabilize and reinforce certain areas of patient anatomy while introducing weight reduction characteristics, flexibility, and breathability components in other areas of patient anatomy.

Various areas of the AFOs may include added thicknesses designed to strategically reinforce such areas to produce certain performance characteristics (e.g., enhanced durability to support weakened patient anatomy). Generally, the added thicknesses can provide structural support for repeated bending motions and reinforce areas that are subject to high stress, while other areas of the AFOs remain low-profile. In some cases, the varying material thicknesses and/or structural components can be provided in the form of one or more structural bands disposed along a body of the AFOs. The one or more structural bands can contribute added thicknesses to baseline thicknesses of the AFOs, thus forming dynamic thickness variations at different portions of the AFOs.

Turning now to FIGS. 1A-1E, one embodiment of a structural band configuration for an AFO is shown positioned in the relation to a lower leg 10 of a patient, wherein the lower leg 10 includes a calf 12, a shin 13, a foot 14, a heel 16, toes 18, and an ankle joint 20.

Figure 1A:
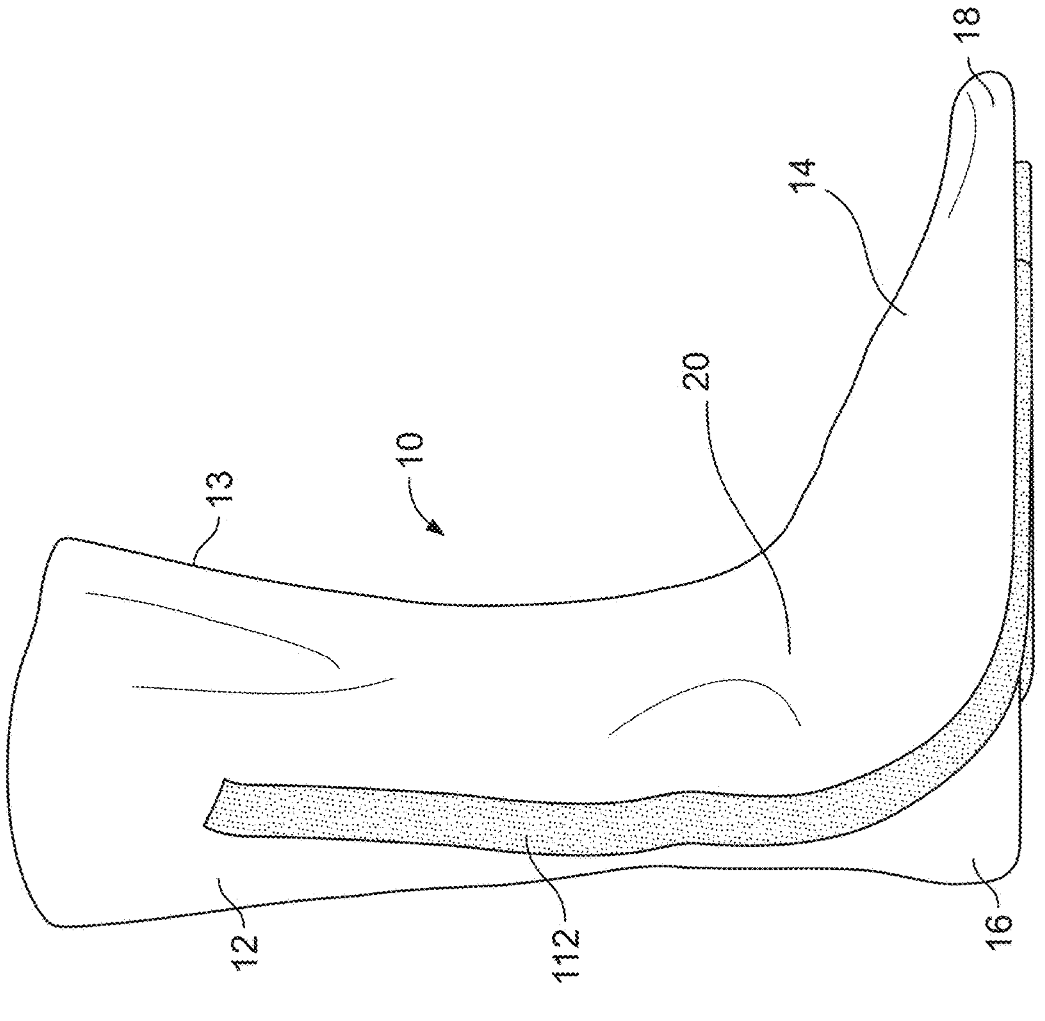
FIG. 1A is a side schematic view of one embodiment of one or more structural bands of an exemplary ankle foot orthotic (AFO) in accordance with the principles of this disclosure.

With reference to FIGS. 1A and 1B, the structural band configuration can include one or more structural bands provided in the form of one or more edge structural bands 110, 112. As shown, the one or more edge structural bands 110, 112 are provided in the form of a medial edge structural band 110 and a lateral edge structural band 112 that are positioned along about the medial and lateral sides of the ankle joint 20, respectively.

In some cases, each of the edge structural bands 110, 112 can extend downwards from about a middle portion of the calf 12, curve around about the ankle joint 20, and extend along about the medial and lateral portions of the plantar surface of the foot 14 to proximal the toes 18. In particular, the edge structural bands 110, 112 can be designed to contribute to rigidity in a sagittal plane of the AFO, provide energy loading, storing, and transfer abilities to the lower support member (e.g., like a spring or hinge), and enable a lower support member of the AFO to bend in relation to the lower leg 10. In particular, as the ankle joint 20 bends during gait, the lower support member of the AFO can bend towards and away from the lower leg 10. Thus, the increased thickness provided by the edge structural bands 110, 112 can enhance the bending and spring-back action of the overall AFO.

In some cases, the edge structural bands 110, 112 can include one or more segments that are split between about at least 10.0 mm to 12.0 mm, or about at least 11.0 mm to 13.0 mm, or about at least 12.0 mm to 14.0 mm, or about at least 13.0 mm to 15.0 mm, or about at least 14.0 mm to 16.0 mm, or about at least 15.0 mm to 17.0 mm, or about at least 16.0 mm to 18.0 mm, or about at least 17.0 mm to 19.0 mm, or about at least 18.0 mm to 20.0 mm above the floor plane.

In some cases, a superior portion of each of the edge structural bands 110, 112 can include an added width to the base width of the AFO of about at least 4.0 to 6.0 mm, or about at least 5.0 to 7.0 mm, or about at least 6.0 to 8.0 mm, or about at least 7.0 to 9.0 mm, or about at least 8.0 to 10.0 mm. Further, the superior portion of each of the edge structural bands 110, 112 can include an added thickness to the baseline thickness of about at least 1.0 mm to 2.0 mm, or about at least 1.5 mm to 2.5 mm, or about at least 2.0 mm to 3.0 mm, or about at least 2.5 mm to 3.5 mm, or about at least 3.0 mm to 4.0 mm, or about at least 3.5 mm to 4.5 mm, or about at least 4.0 mm to 5.0 mm.

An inferior portion of each of the edge structural bands 110, 112 can include an added width to the base width of the AFO of about at least 1.0 to 3.0 mm, or about at least 2.0 to 4.0 mm, or about at least 3.0 to 5.0 mm, or about at least 4.0 to 6.0 mm, or about at least 5.0 to 7.0 mm. Further, the inferior portion of each of the edge structural bands 110, 112 and can include an added thickness to the baseline thickness of about at least 0.5 to 1.5 mm, or about at least 1.0 mm to 2.0 mm, or about at least 1.5 mm to 2.5 mm, or about at least 2.0 mm to 3.0 mm, or about at least 2.5 mm to 3.5 mm, or about at least 3.0 mm to 4.0 mm. In one non-limiting example, a tall patient may require an AFO with a relatively long body that can exert an increased force during gait (e.g., similar to a relatively long lever providing increased torque). An AFO in this example may thus require increased stiffness in the sagittal plane via a widening and thickening of up to 50% of the superior portions of the medial and lateral edge structural bands 110, 112.

Figure 1D:
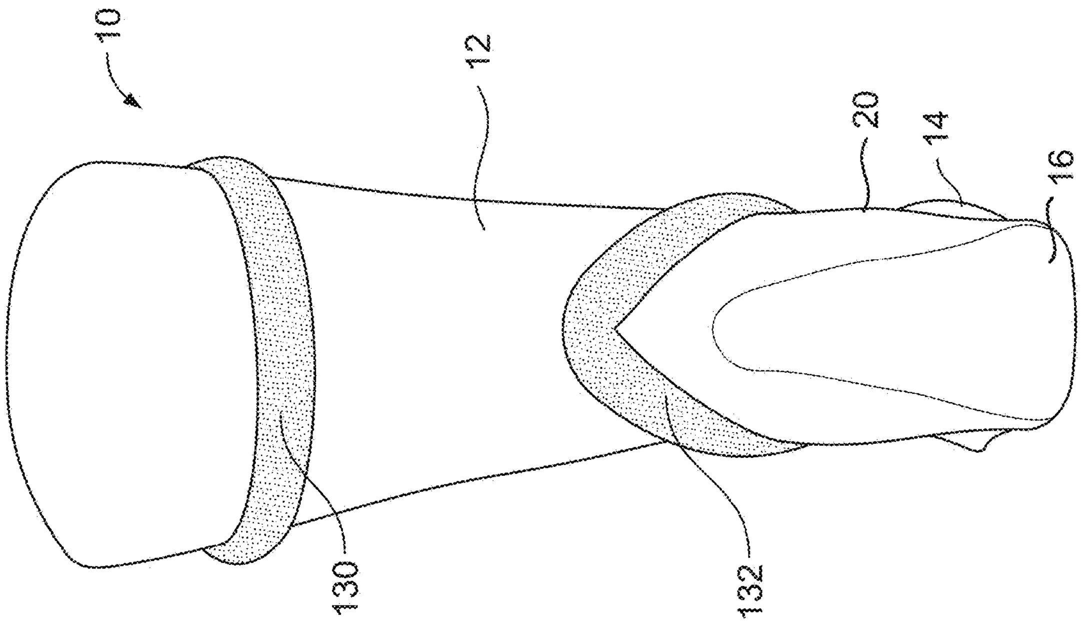
FIG. 1D is a back schematic view of the one or more structural bands of FIG. 1C.
Figure 1C:
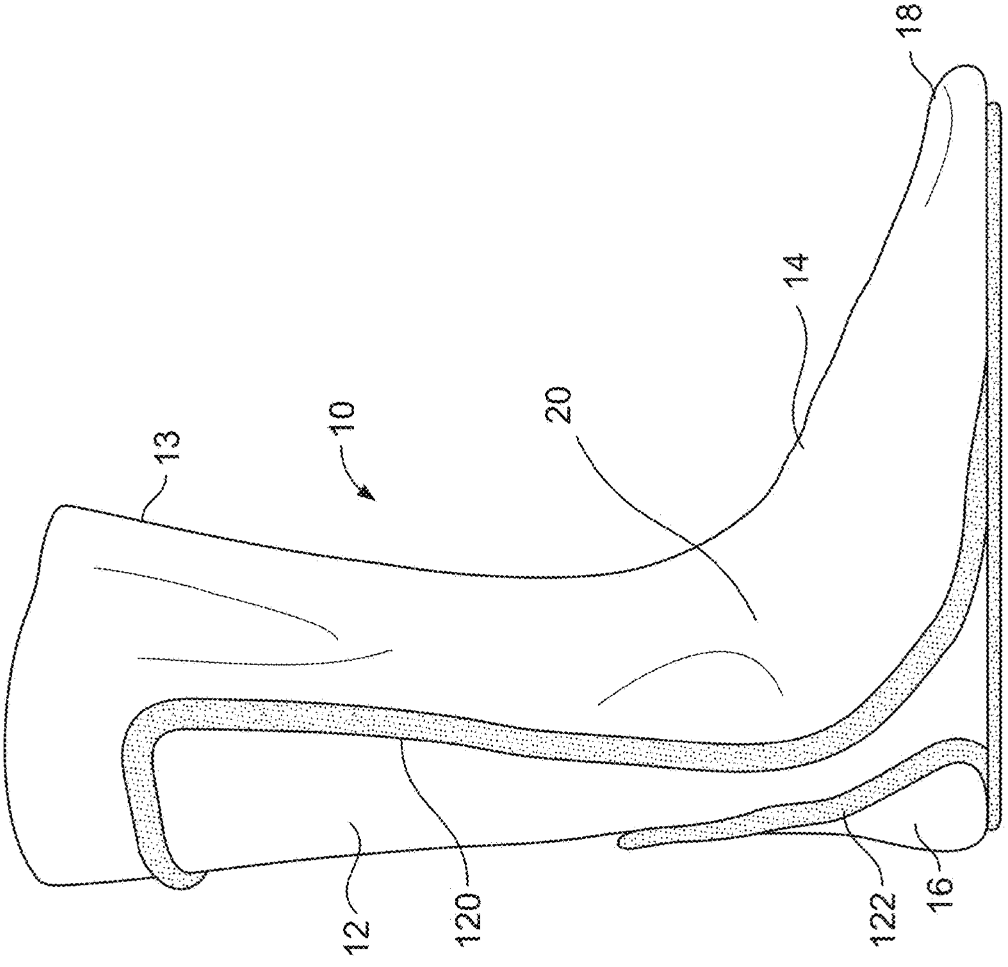
FIG. 1C is a side schematic view of one embodiment of one or more structural bands of an exemplary AFO in accordance with the principles of this disclosure.

With particular reference to FIG. 1C, one embodiment of a structural band configuration for an AFO is shown positioned in the relation to a lower leg 10 of a patient. Here, the structural band configuration can include one or more structural bands provided in the form of an outer perimeter structural band 120 and an inner perimeter structural band 122.

In some cases, the outer perimeter structural band 120 can be positioned with the contour of the overall AFO such that the outer perimeter structural band 120 extends across and downwards from about a middle portion of the calf 12, curves around about the ankle joint 20, and extends along about the medial and lateral portions of the plantar surface of the foot 14 to proximal the toes 18.

In some cases, the inner perimeter structural band 122 can be positioned with the contour of one or more features included on the AFO such that the inner perimeter structural band 122 extends around a rear portion of the patient's foot 14 and ankle joint 20 (e.g., the heel area).

The outer and inner perimeter structural bands 120, 122 can be designed to shield stress from exposed edges of the AFO, provide rigidity to the heel-area of the AFO, and prevent fracture propagation at the edges of the AFO. Thus, the outer and inner perimeter structural bands 120, 122 can encompass one or more edges of the AFO. Further, the outer and inner perimeter structural bands 120, 122 can include an added width to the base width of the AFO of about at least 1.0 to 3.0 mm, or about at least 2.0 to 4.0 mm, or about at least 3.0 to 5.0 mm, or about at least 4.0 to 6.0 mm, or about at least 5.0 to 7.0 mm. Further, the inner and outer perimeter structural bands 120, 122 can include an added thickness to the baseline thickness of about at least 0.5 to 1.5 mm, or about at least 1.0 mm to 2.0 mm, or about at least 1.5 mm to 2.5 mm, or about at least 2.0 mm to 3.0 mm, or about at least 2.5 mm to 3.5 mm, or about at least 3.0 mm to 4.0 mm.

In some embodiments, other components of the AFO having exposed edges can include similar perimeter structural bands (such as the anterior plate) that are designed to provide similar effects as the outer and inner perimeter structural bands 120, 122.

With particular reference to FIG. 1D, one embodiment of a structural band configuration for an AFO is shown positioned in the relation to a lower leg 10 of a patient. Here, the structural band configuration can include one or more structural bands provided in the form of an upper crossing structural band 130 and a lower crossing structural band 132. For instance, the upper crossing structural band 130 can extend across about the middle portion of the calf 12 to provide reinforcement and support while the AFO is in use. The lower crossing structural band 132 can form a substantially "horseshoe" pattern at about a lower portion of the calf 12/upper portion of the ankle joint 20 to reduce force felt by the patient and maintain alignment/lift for the foot (e.g., the foot remains lifted at about 90-degrees).

In some cases, the upper and lower crossing structural bands 130, 132 can be designed to improve energy transfer throughout the AFO. The upper and lower crossing structural bands 130, 132 can include an added width of the AFO of about at least 4.0 to 6.0 mm, or about at least 5.0 to 7.0 mm, or about at least 6.0 to 8.0 mm, or about at least 7.0 to 9.0 mm, or about at least 8.0 to 10.0 mm. Further, the upper and lower crossing structural bands 130, 132 can include an added thickness to the baseline thickness of about at least 1.0 mm to 2.0 mm, or about at least 1.5 mm to 2.5 mm, or about at least 2.0 mm to 3.0 mm, or about at least 2.5 mm to 3.5 mm, or about at least 3.0 mm to 4.0 mm, or about at least 3.5 mm to 4.5 mm, or about at least 4.0 mm to 5.0 mm. In one non-limiting example, a patient with elevated activity levels involving lateral movement (e.g., walking on unstable surfaces, hiking, sports, etc.) may benefit from an increased thickness of up to 50% via the upper and lower crossing structural bands.

Figure 1E:
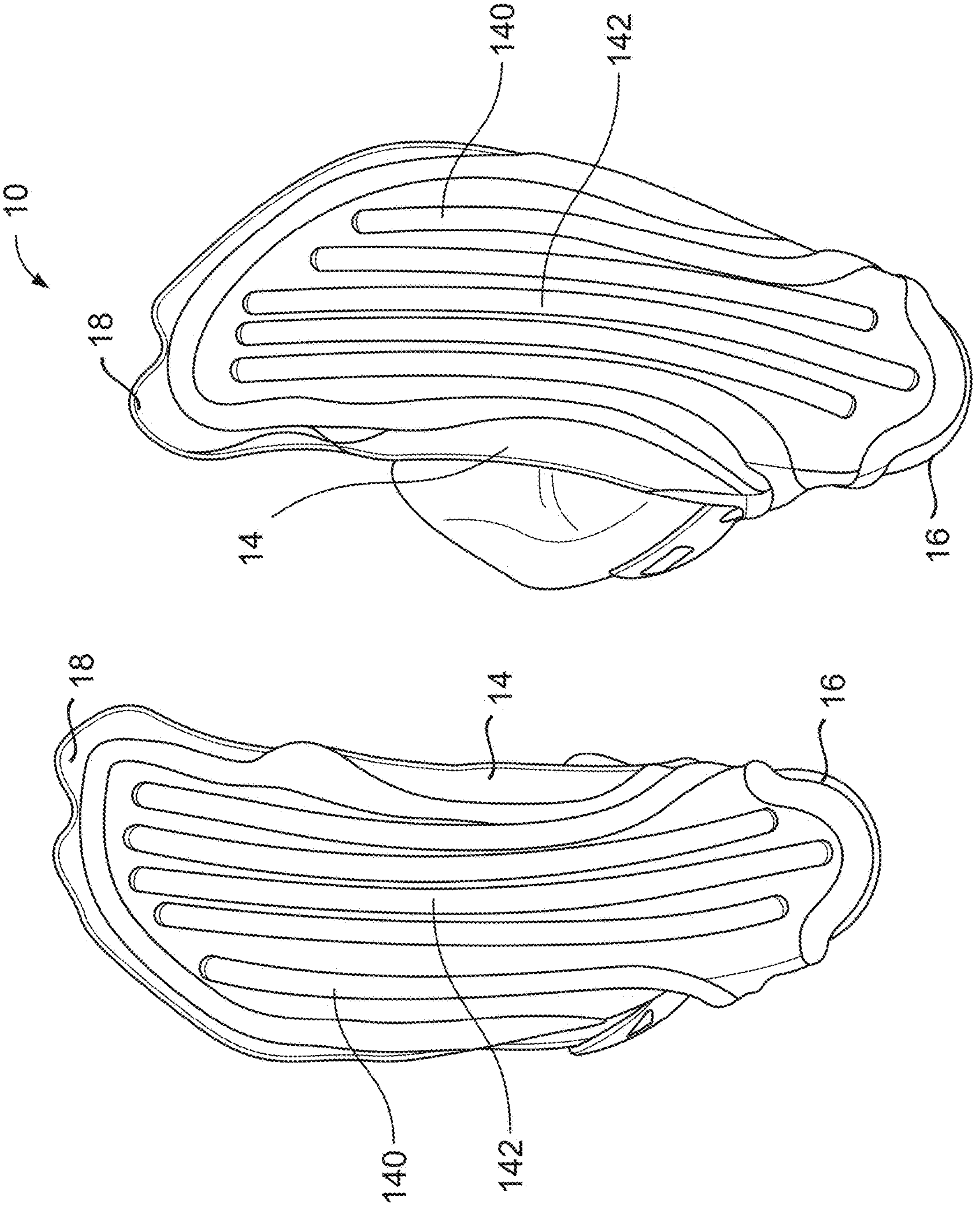
FIG. 1E is a bottom schematic view of one embodiment of one or more structural bands of an exemplary AFO in accordance with the principles of this disclosure.
Figure 2:
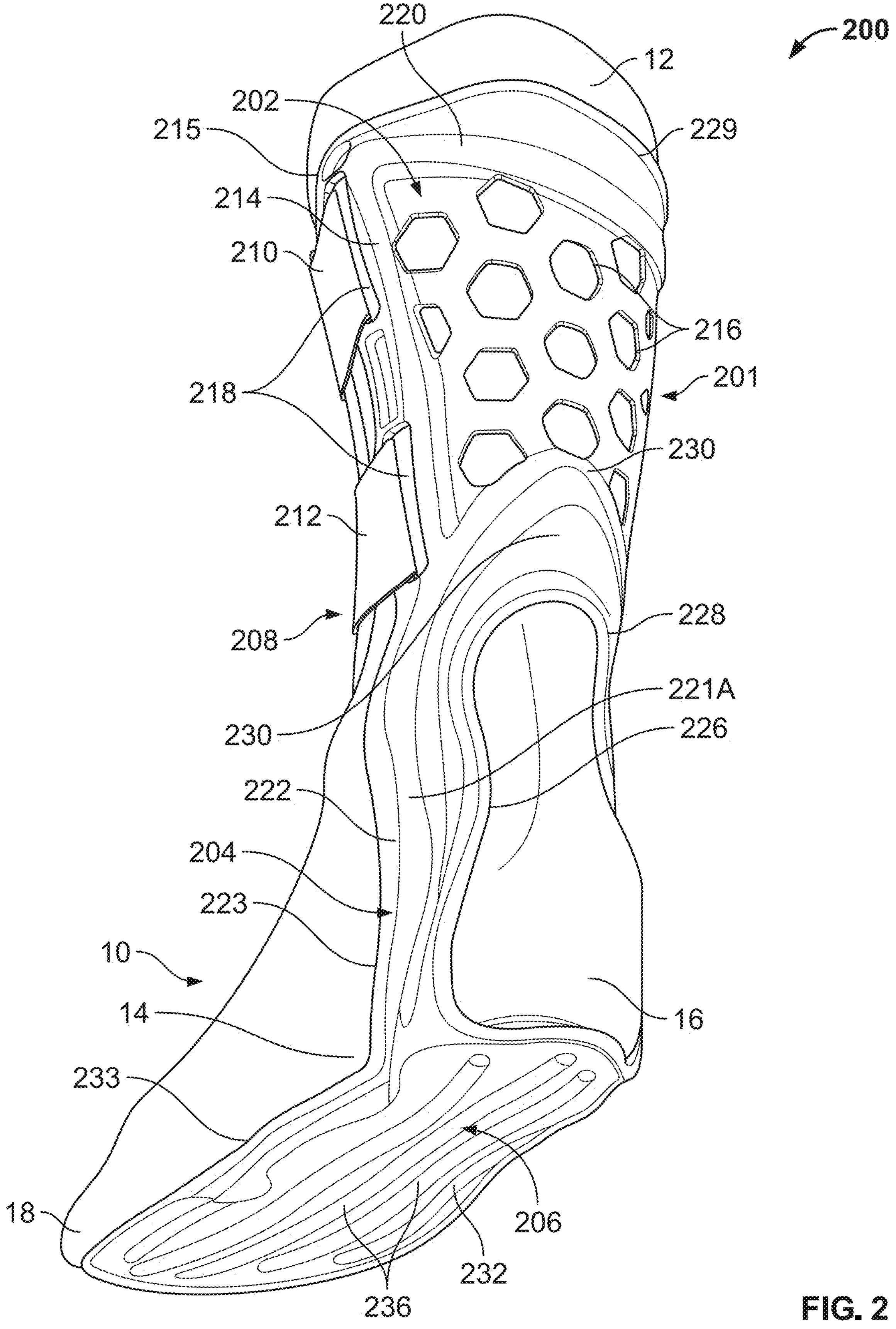
FIG. 2 is a posterior perspective view of an exemplary AFO, according to one embodiment.
Figure 3:
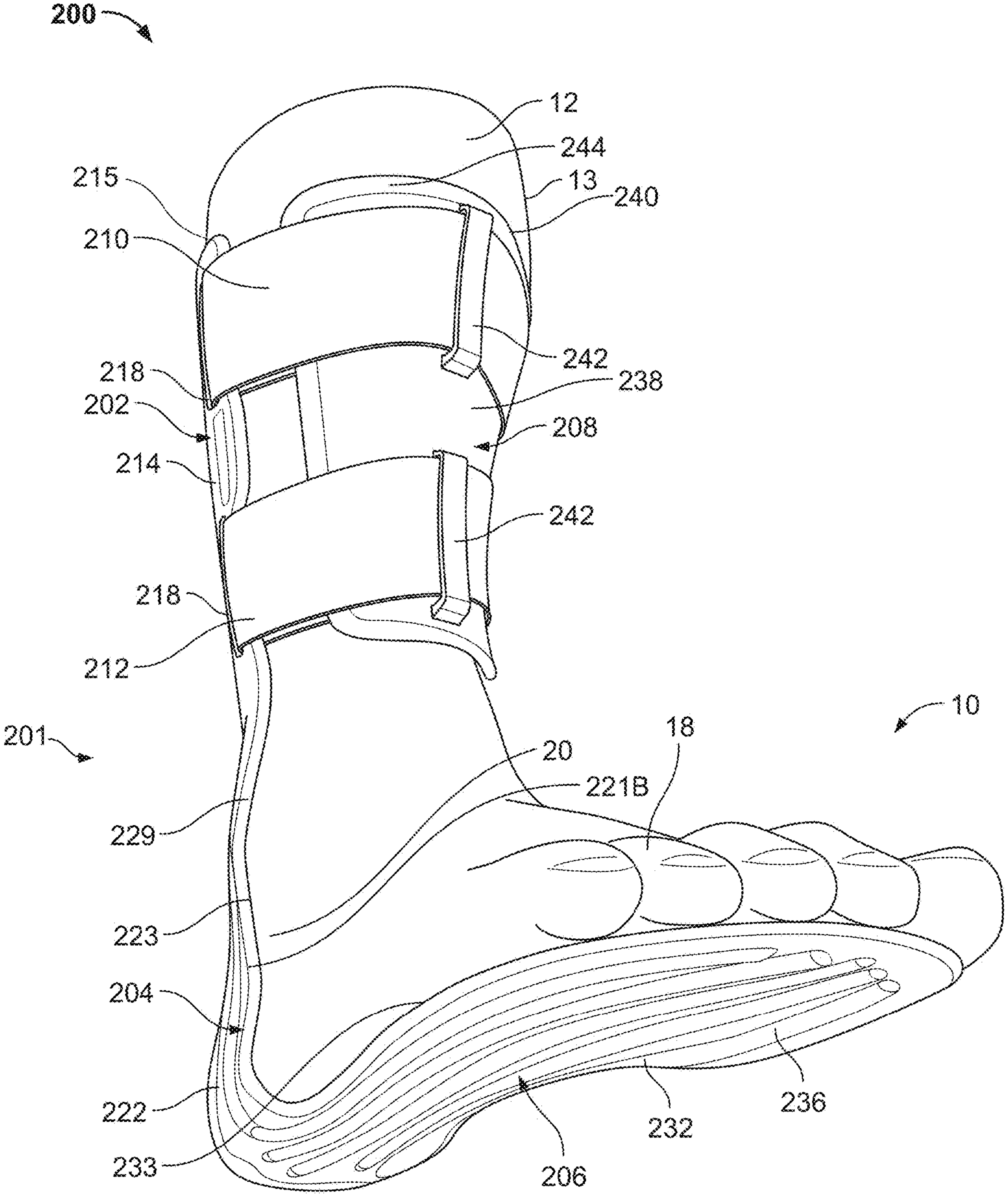
FIG. 3 is an anterior perspective view of the AFO of FIG. 2.
Figure 4:
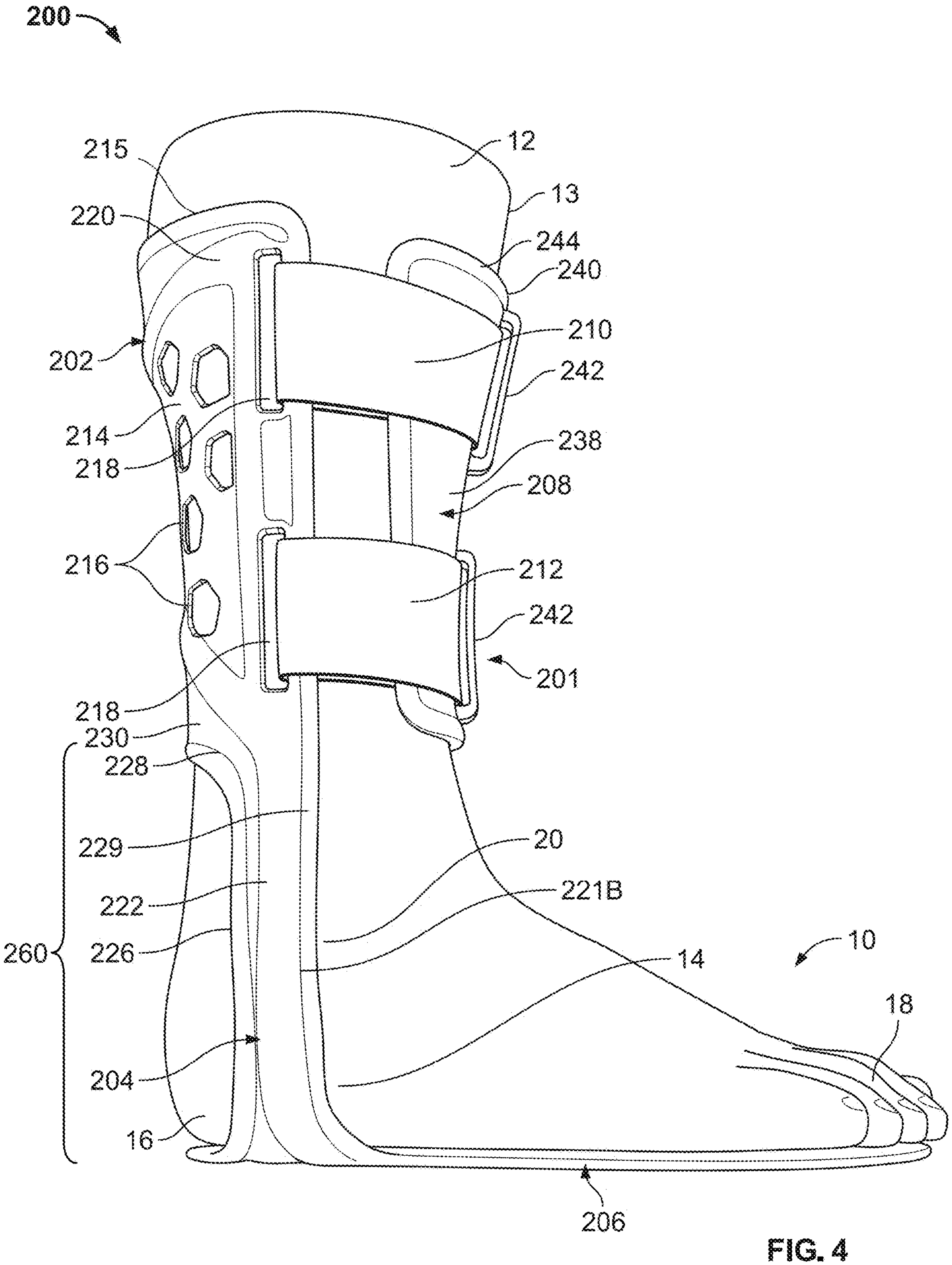
FIG. 4 is a lateral side view of the AFO of FIG. 2.
Figure 5:
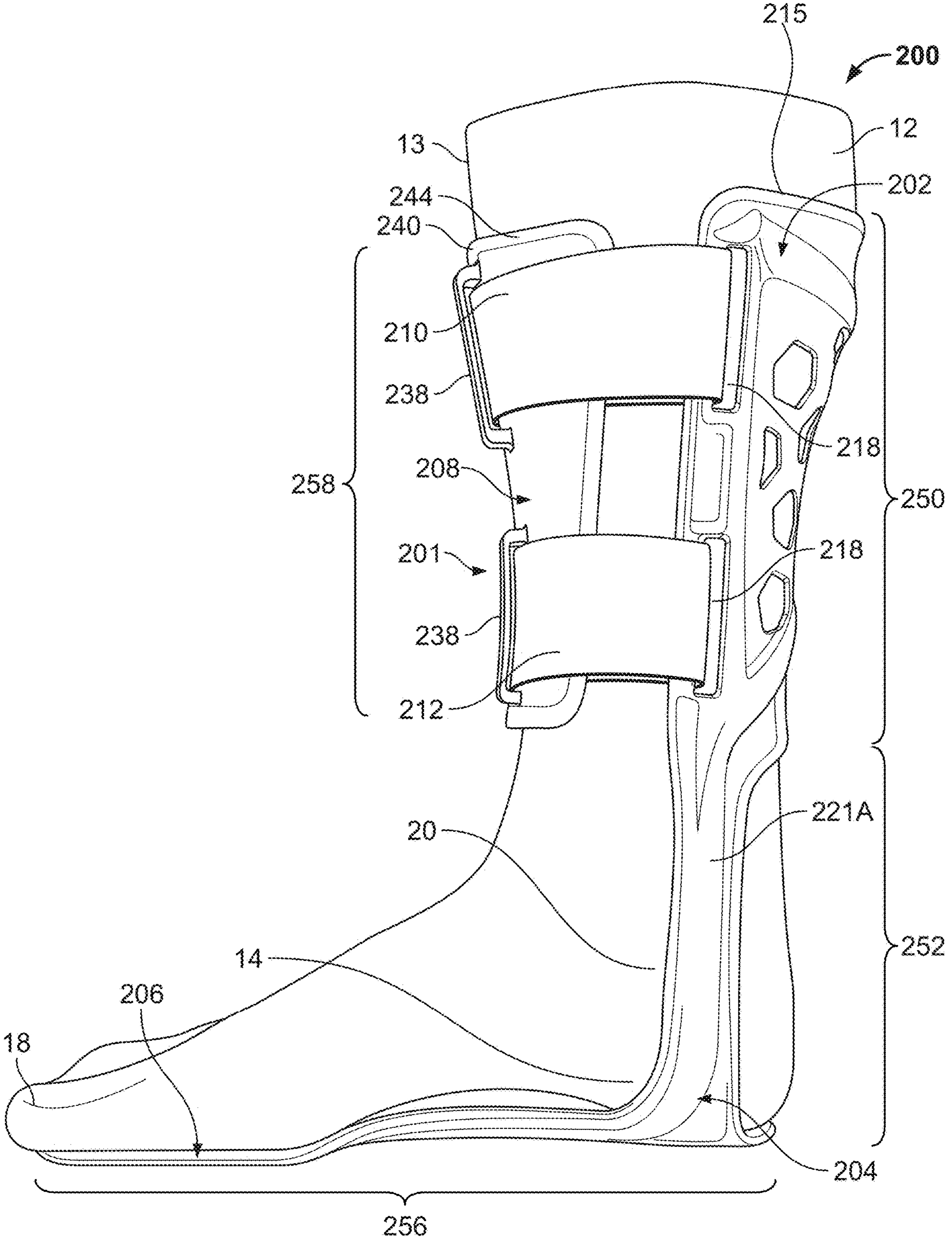
FIG. 5 is a medial side view of the AFO of FIG. 2.
Figure 6:
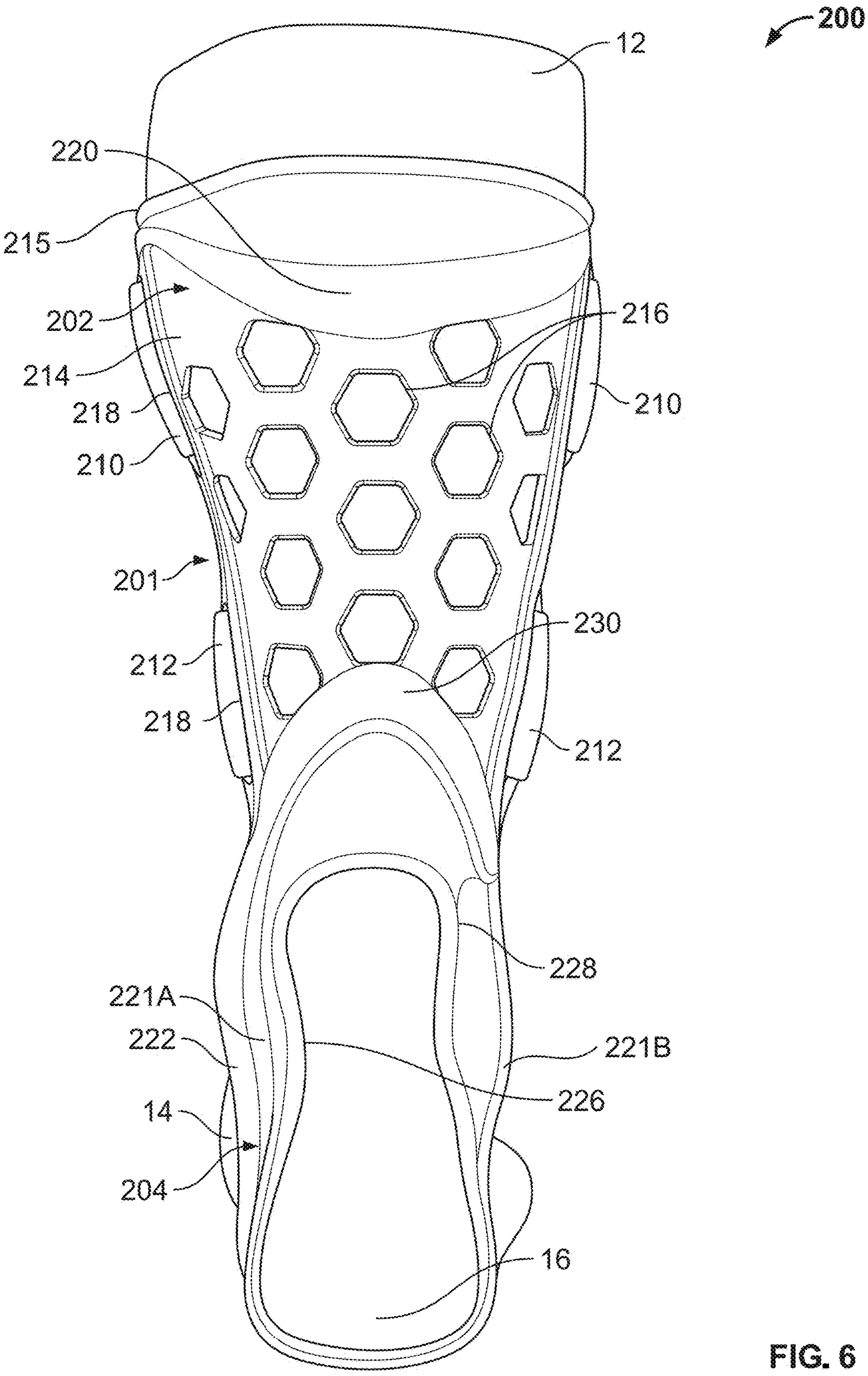
FIG. 6 is a posterior view of the AFO of FIG. 2.
Figure 7:
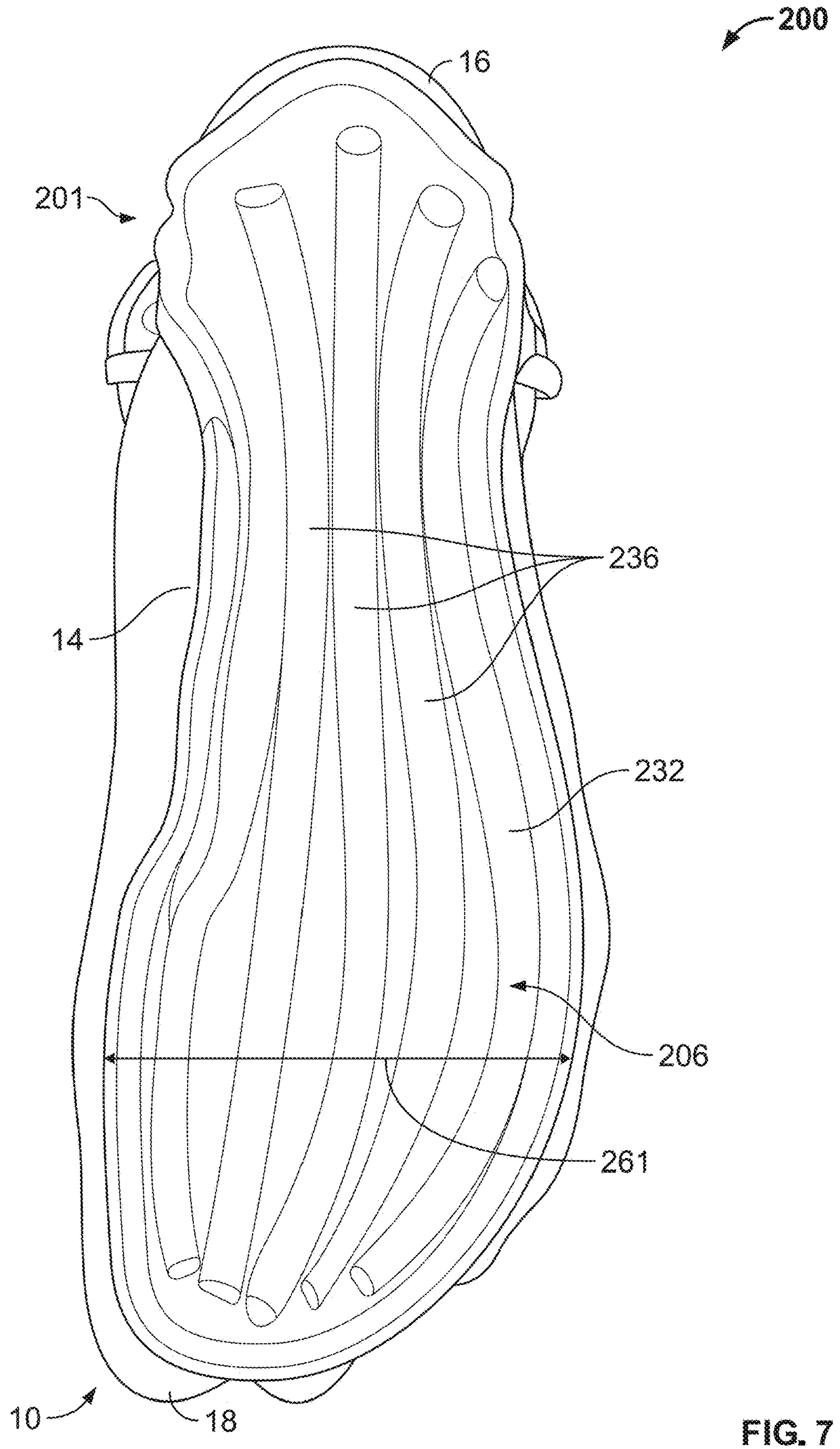
FIG. 7 is a bottom view of the AFO of FIG. 2.
Figure 8:
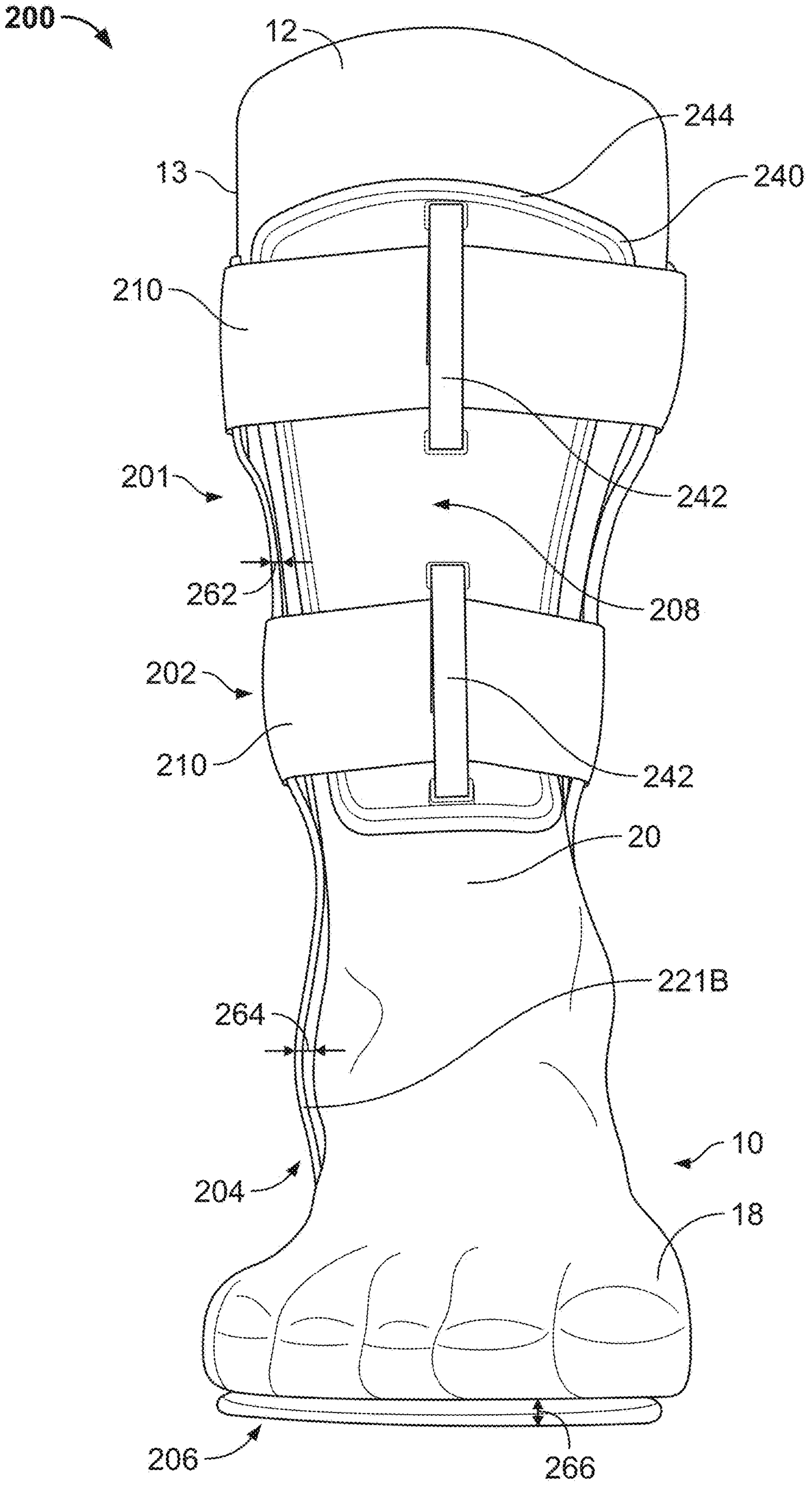
FIG. 8 is an anterior view of the AFO of FIG. 2.
Figure 9:
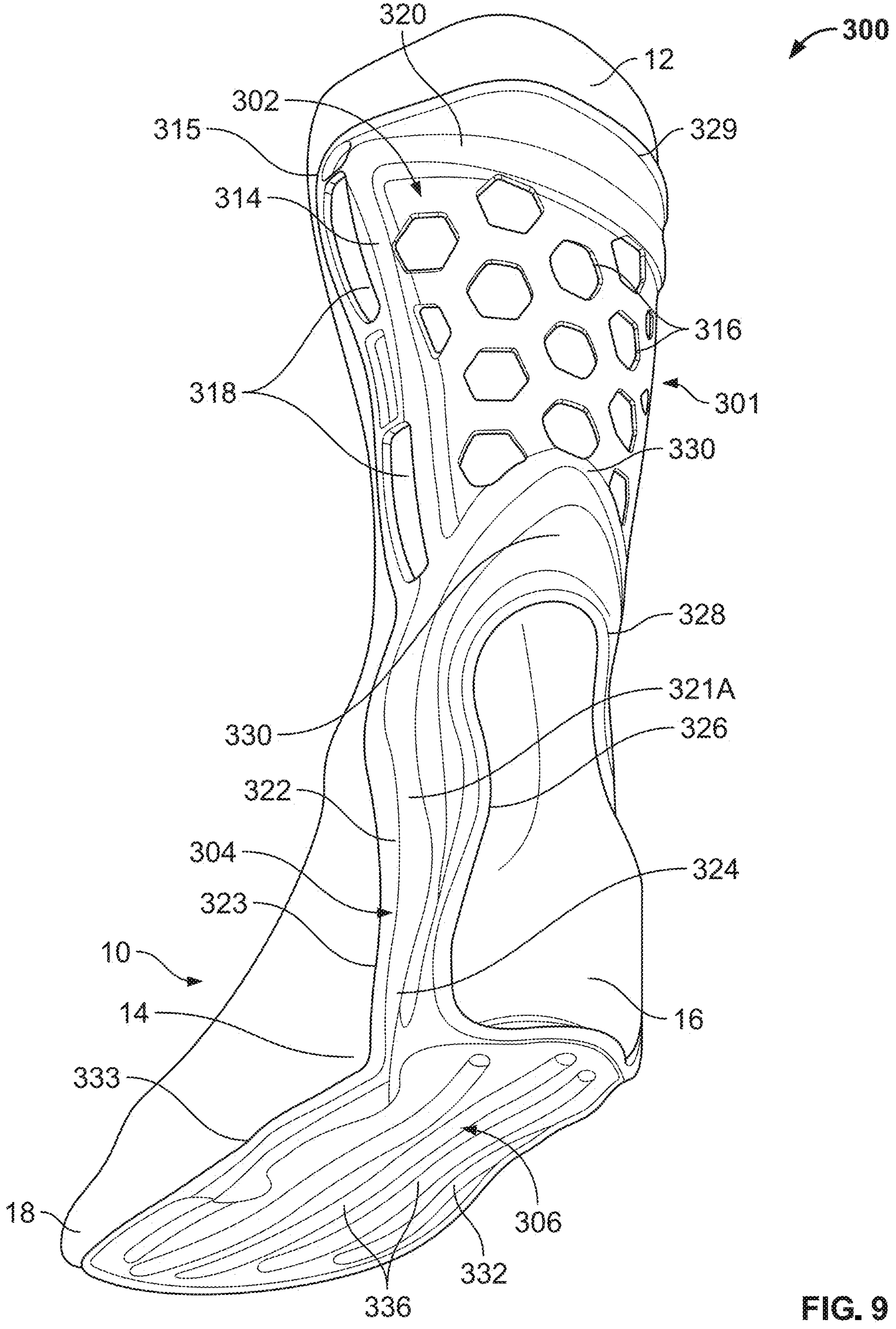
FIG. 9 is a posterior perspective view of an exemplary AFO, according to one embodiment.
Figure 10:
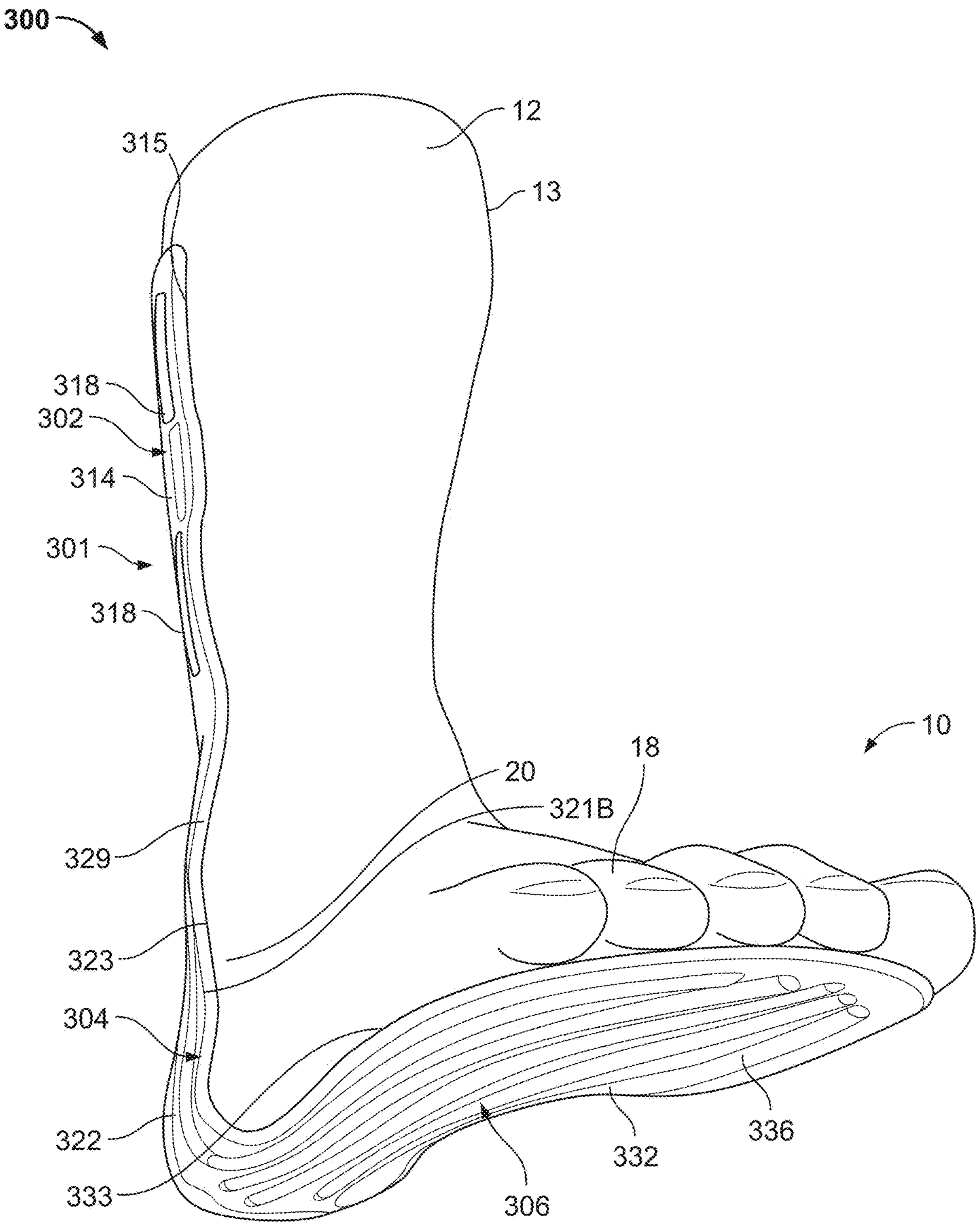
FIG. 10 is an anterior perspective view of the AFO of FIG. 9.
Figure 11:
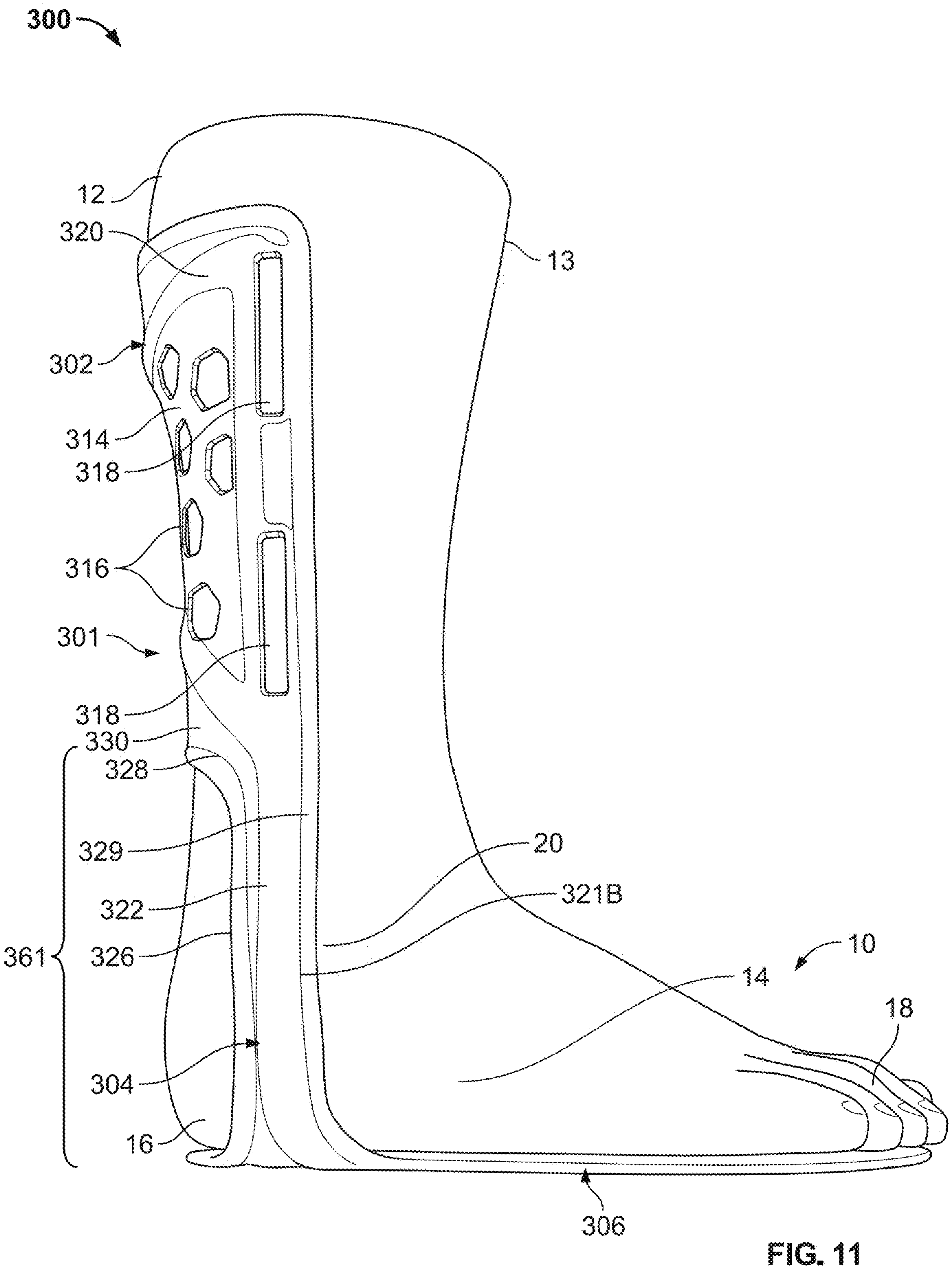
FIG. 11 is a lateral side view of the AFO of FIG. 9.
Figure 12:
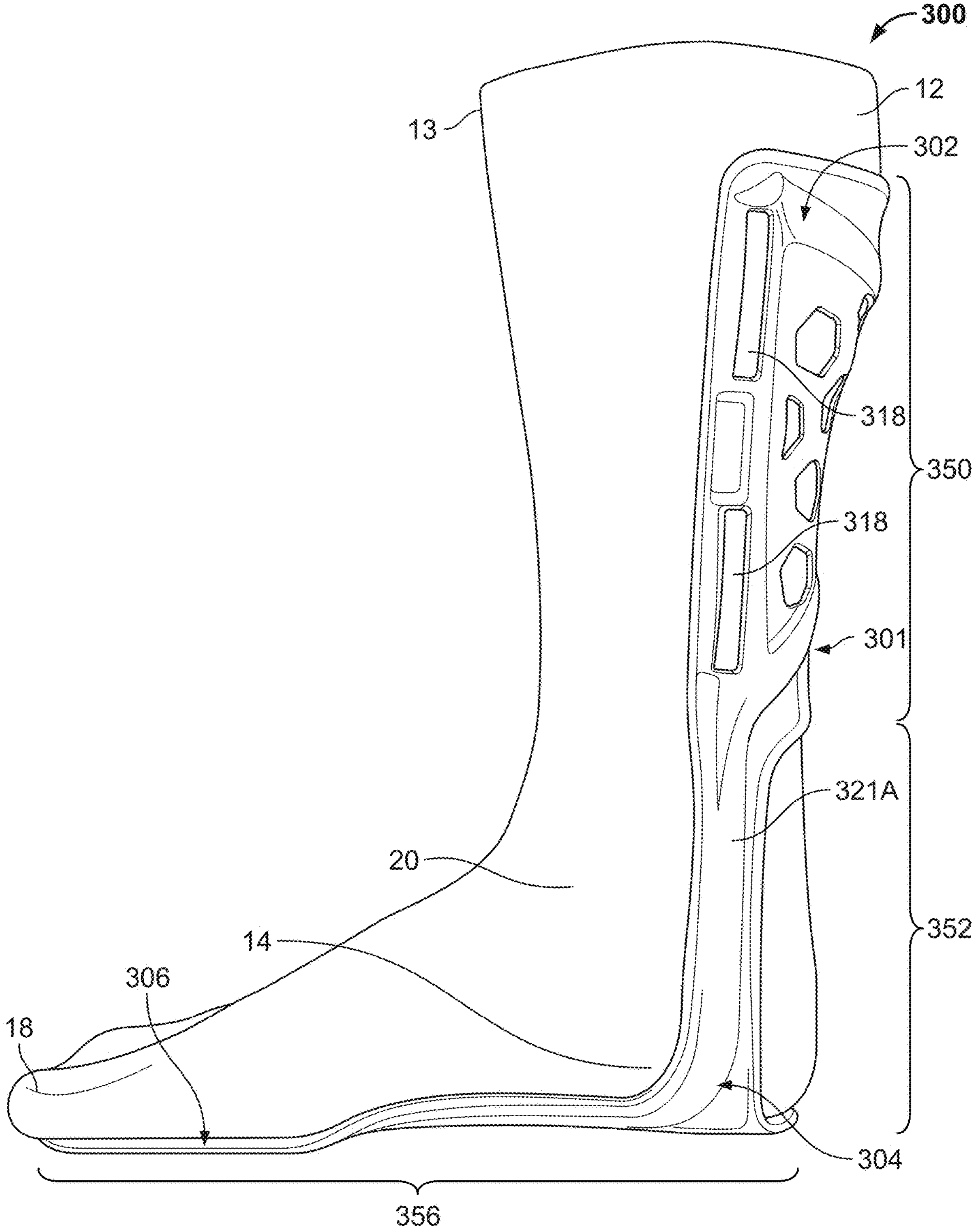
FIG. 12 is a medial view of the AFO of FIG. 9.
Figure 13:
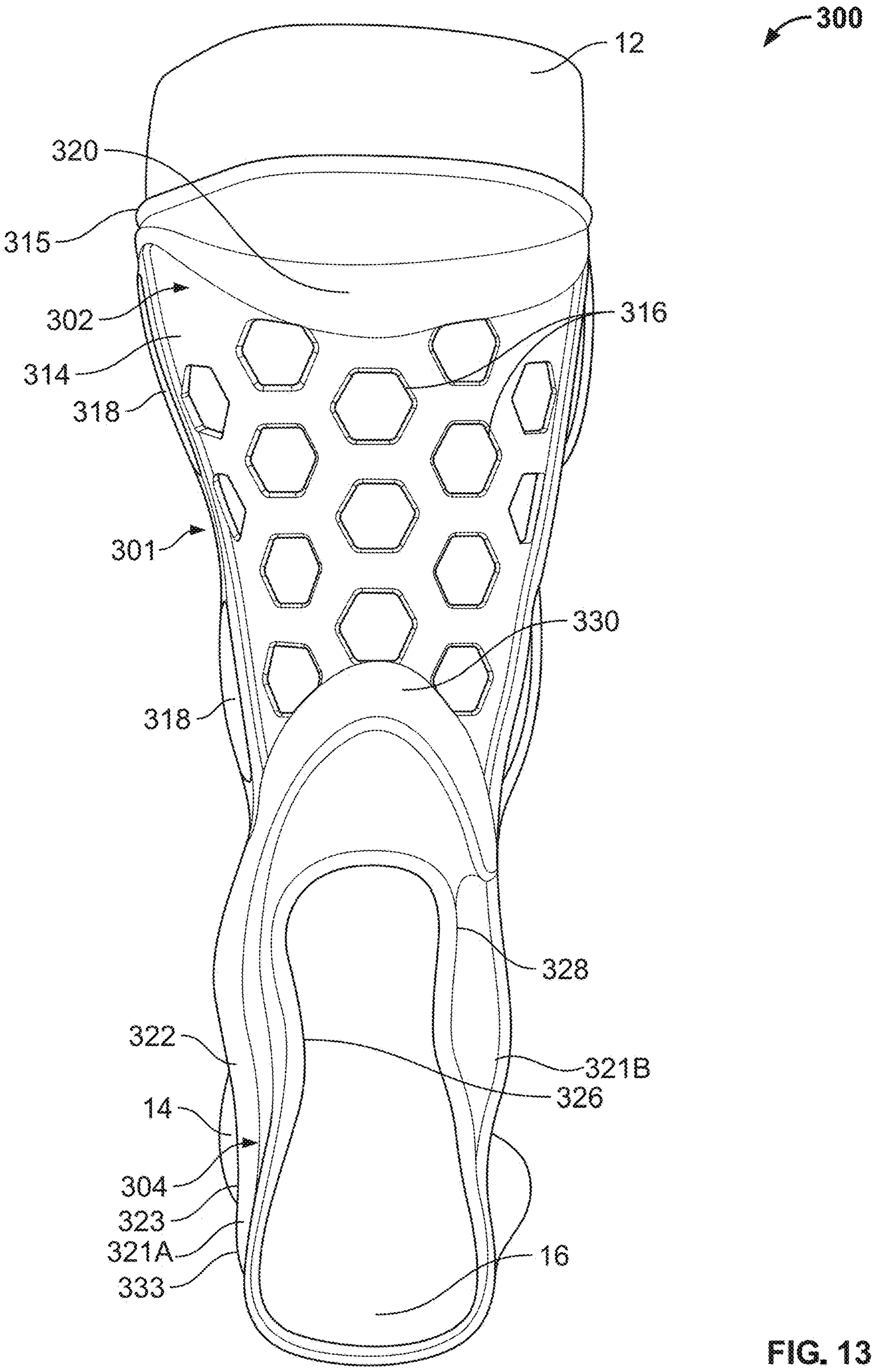
FIG. 13 is an anterior view of the AFO of FIG. 9.
Figure 14:
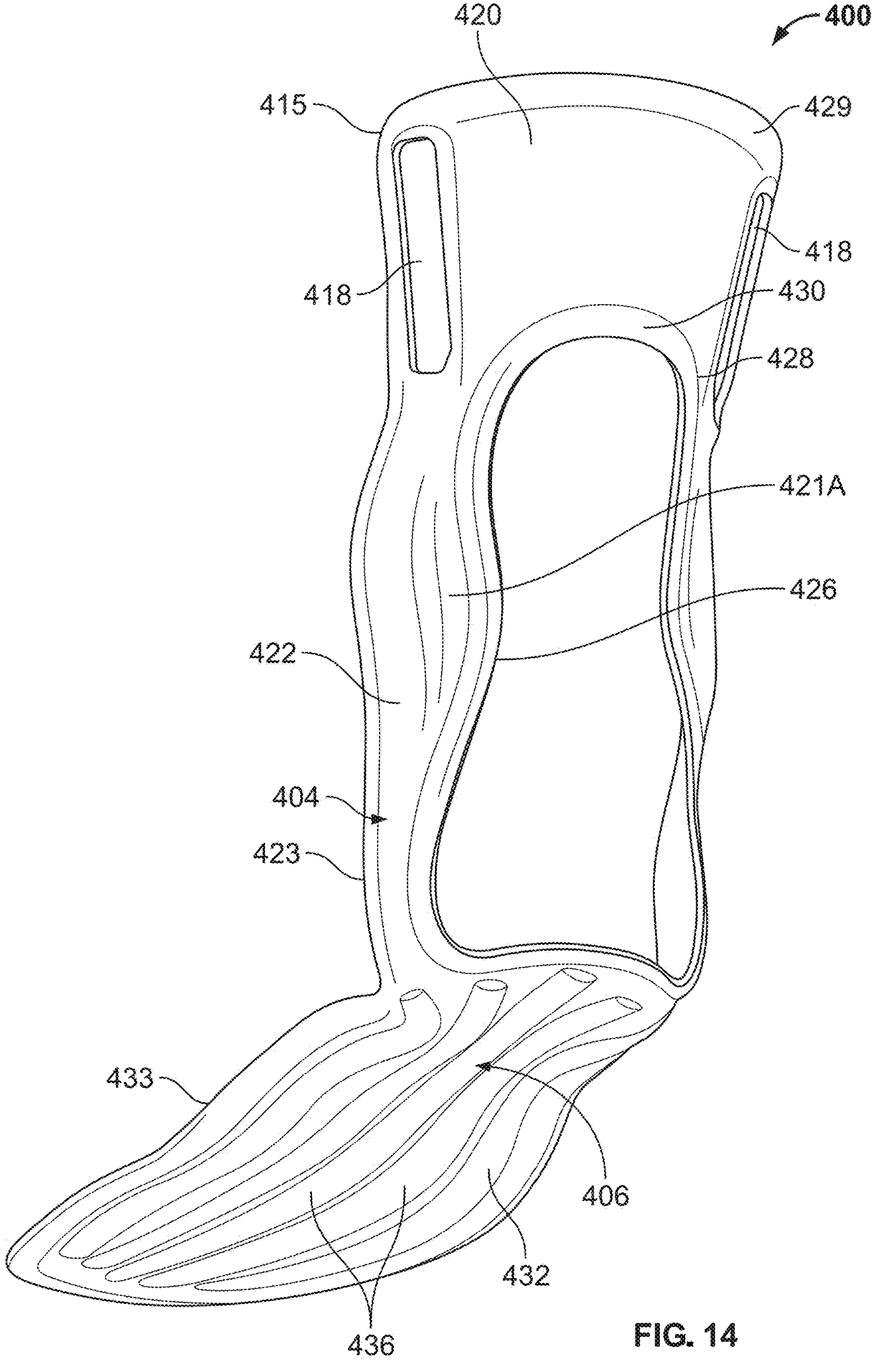
FIG. 14 is a posterior perspective view of an exemplary AFO, according to one embodiment.
Figure 15:
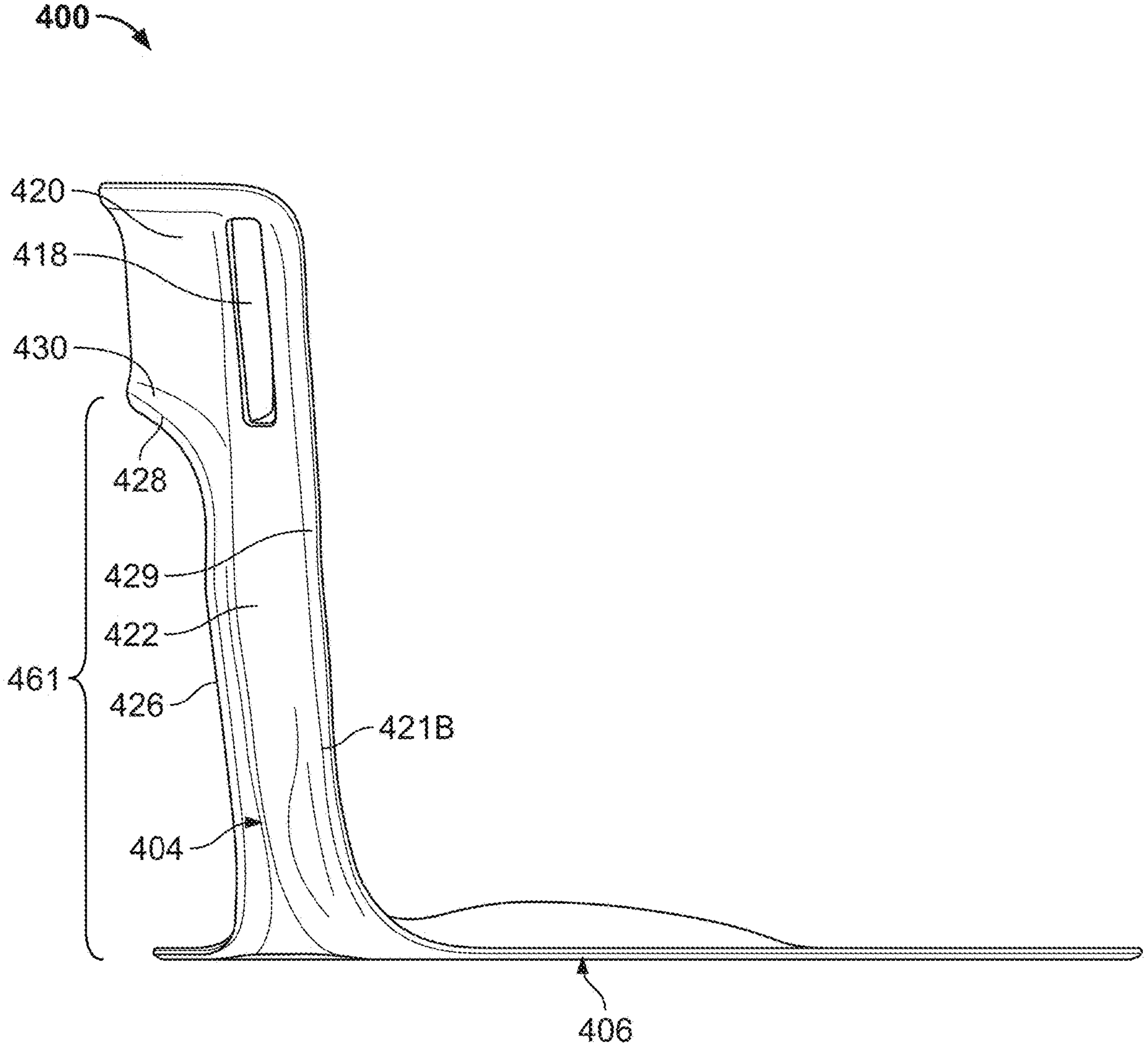
FIG. 15 is a lateral side view of the AFO of FIG. 14.
Figure 16:
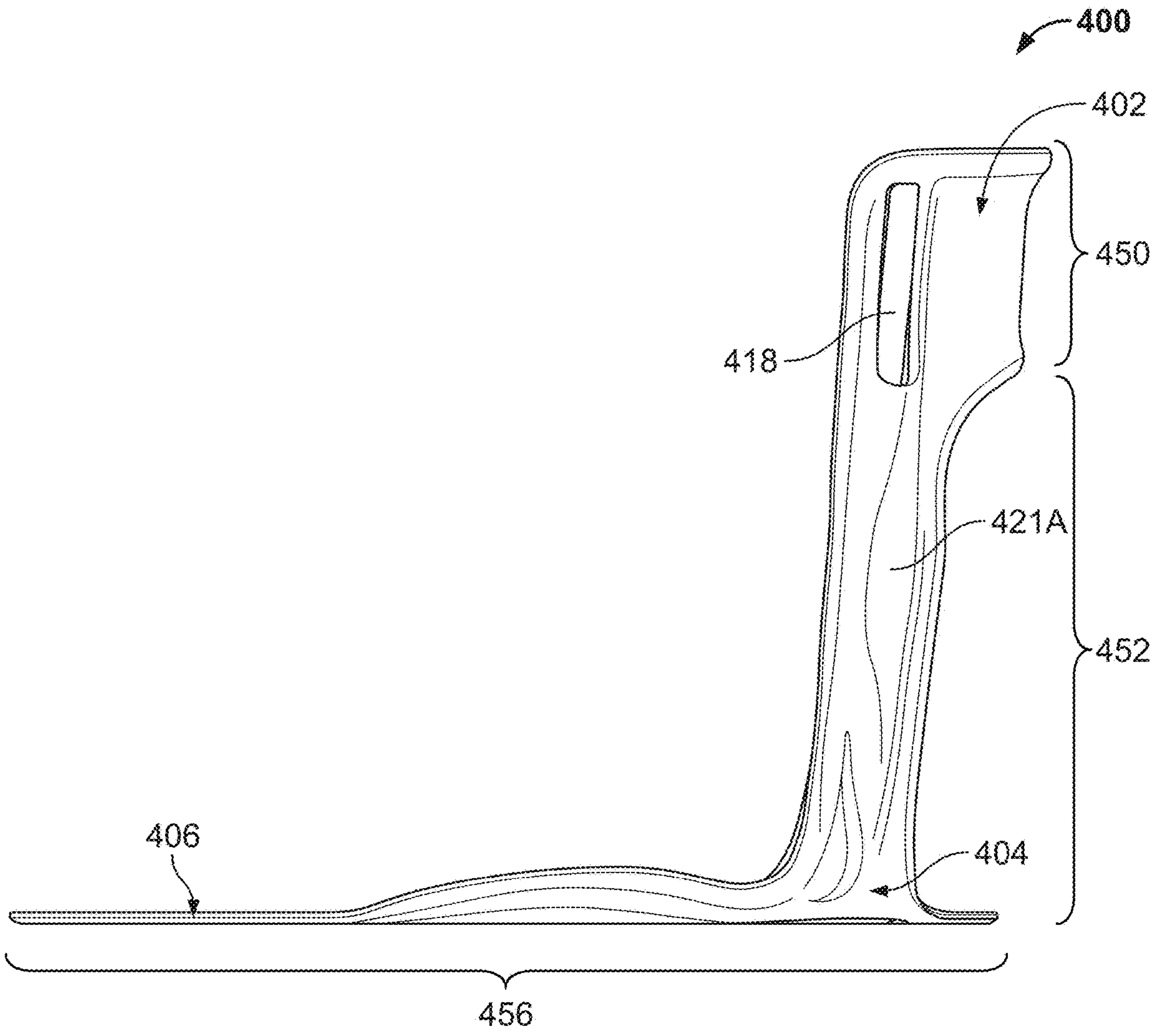
FIG. 16 is a medial side view of the AFO of FIG. 14.
Figure 17:
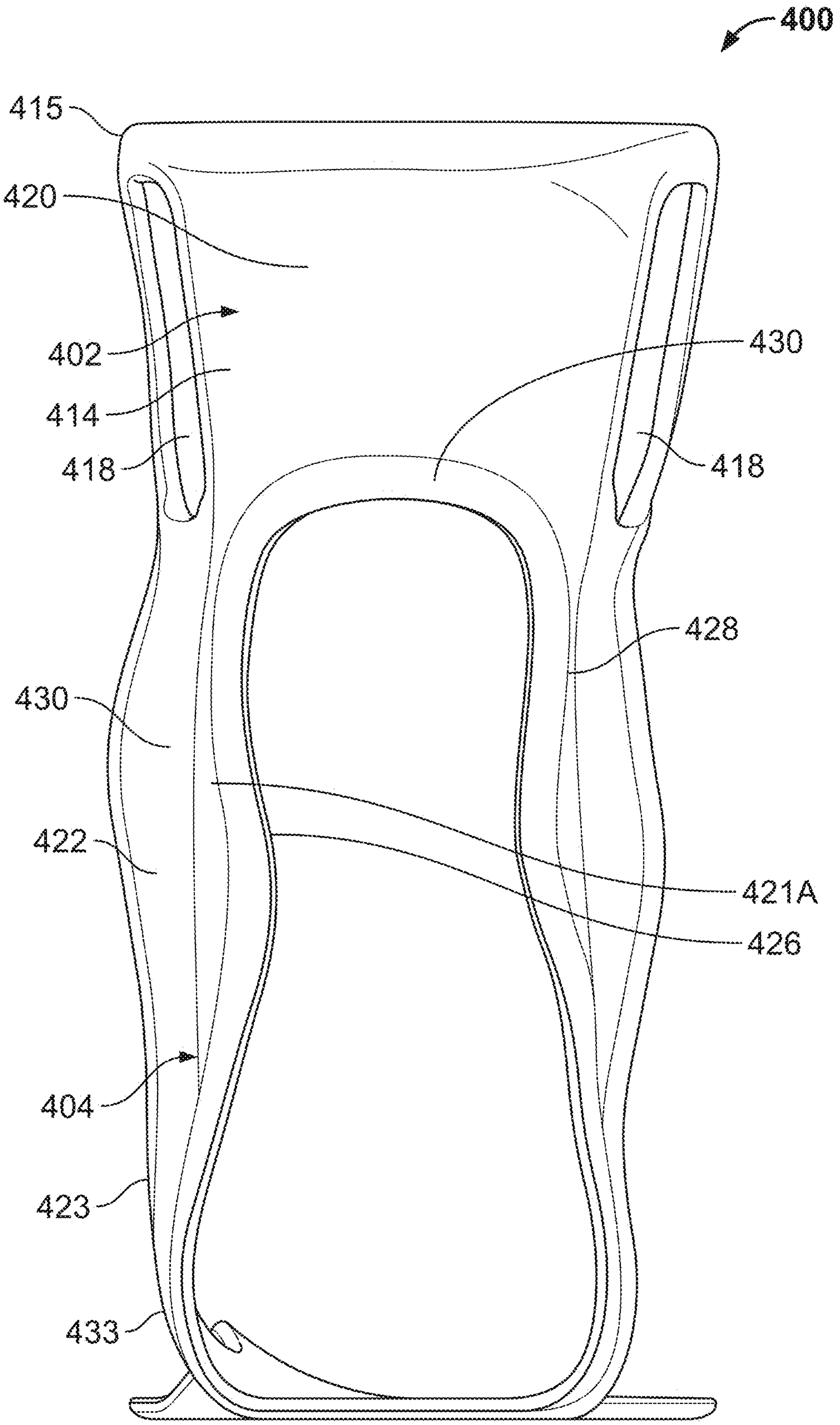
FIG. 17 is a posterior view of the AFO of FIG. 14.
Figure 18:
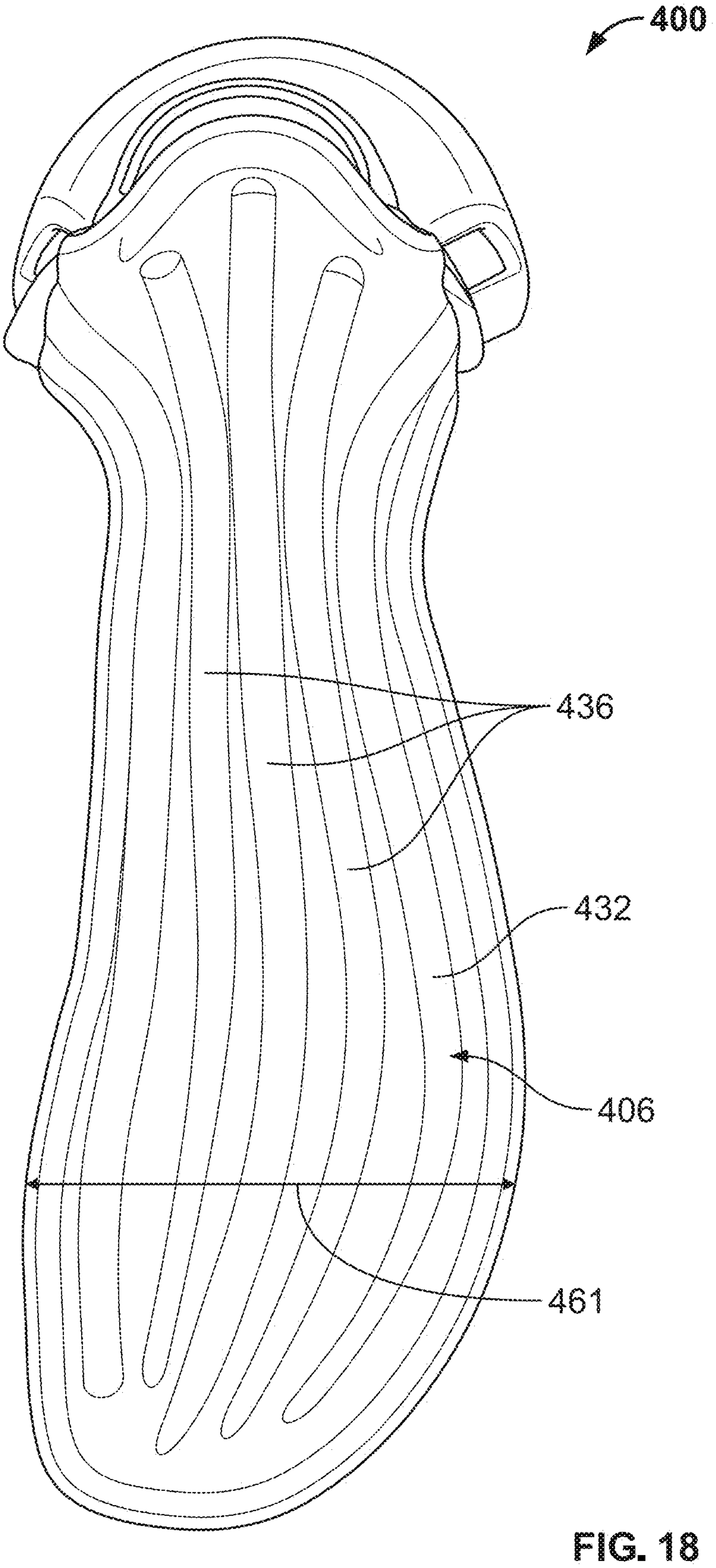
FIG. 18 is a bottom view of the AFO of FIG. 14.
Figure 19:
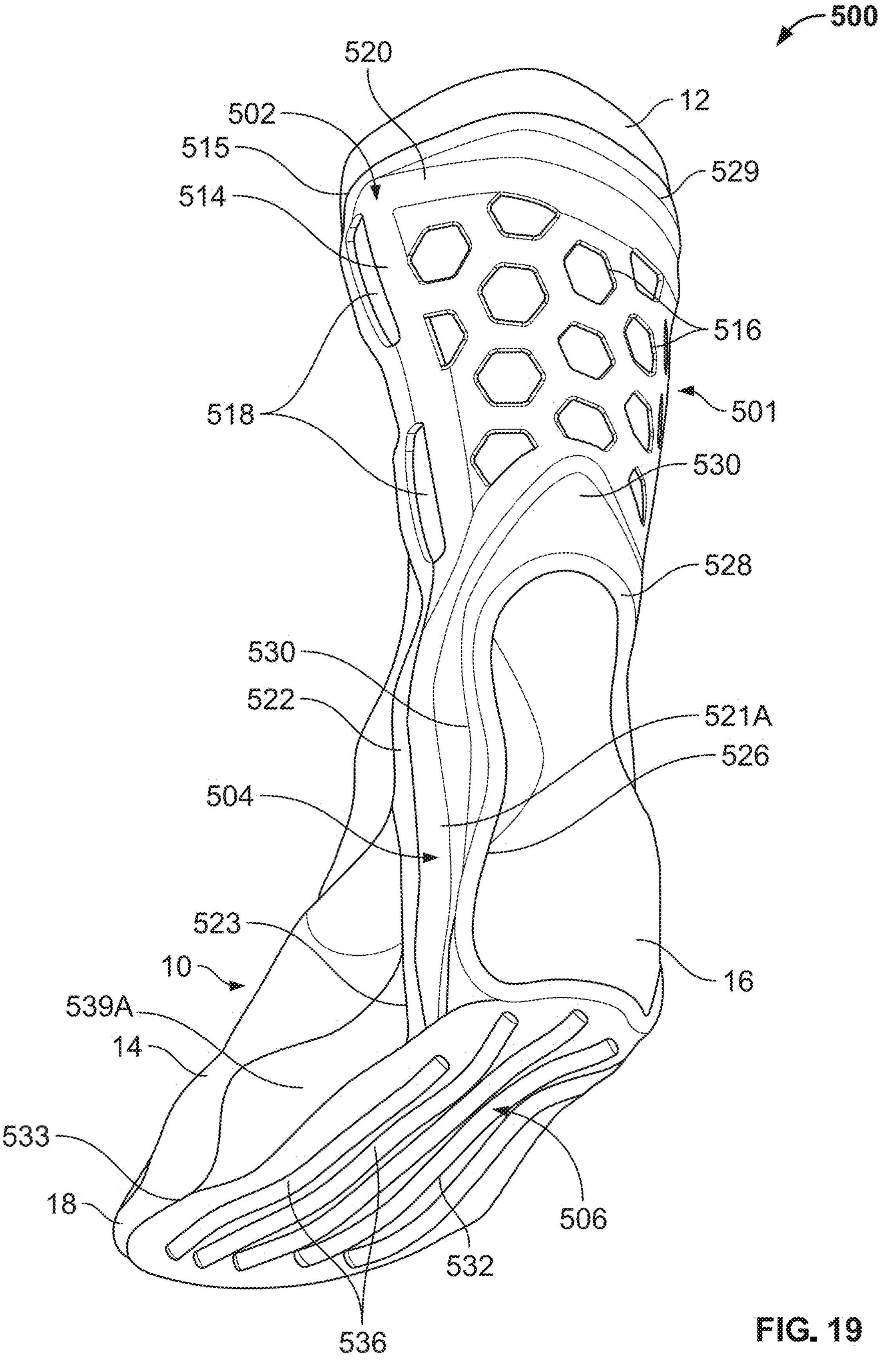
FIG. 19 is a posterior perspective view of an exemplary AFO, according to one embodiment.
Figure 20:
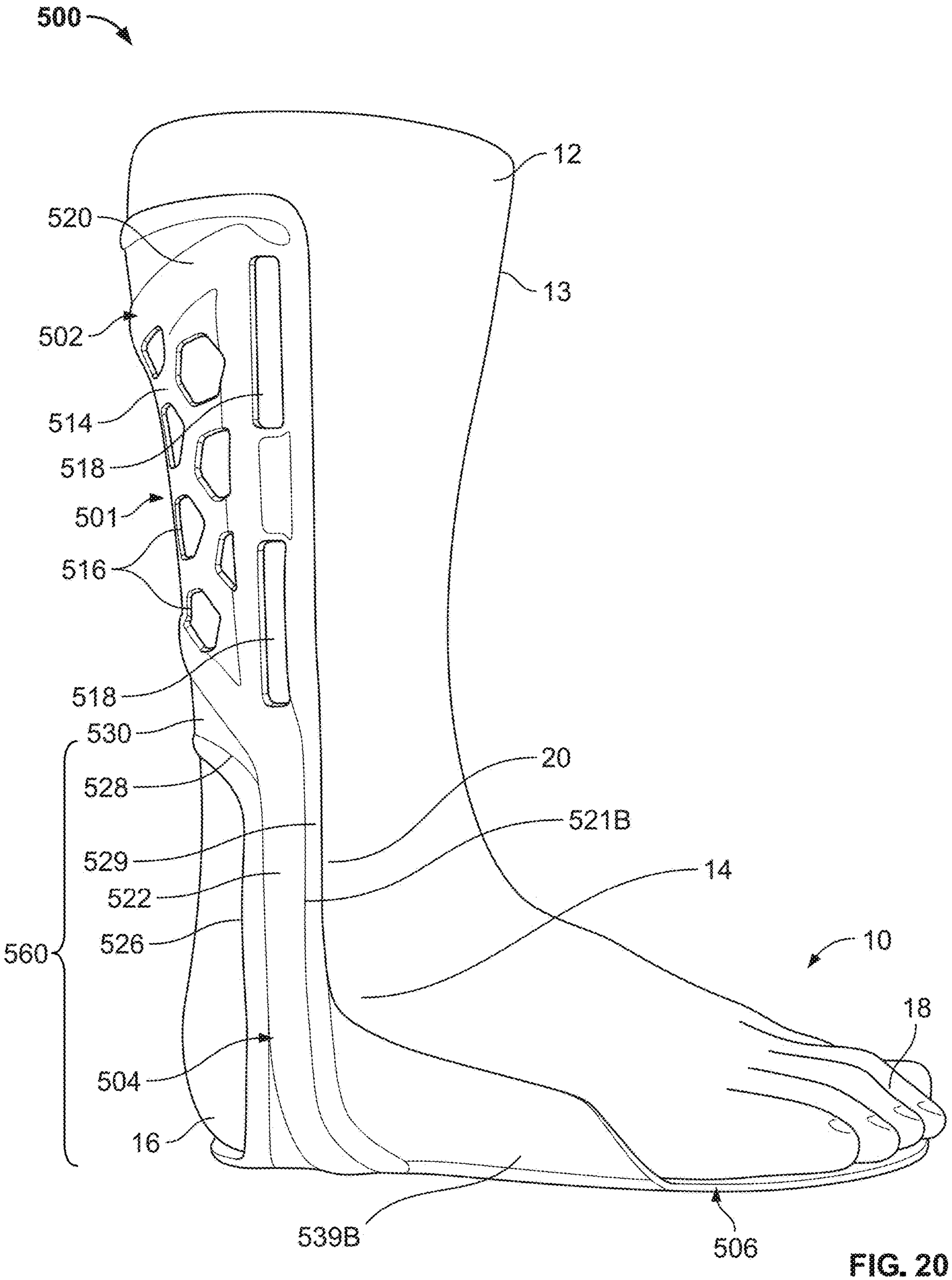
FIG. 20 is a lateral side view of the AFO of FIG. 19.
Figure 21:
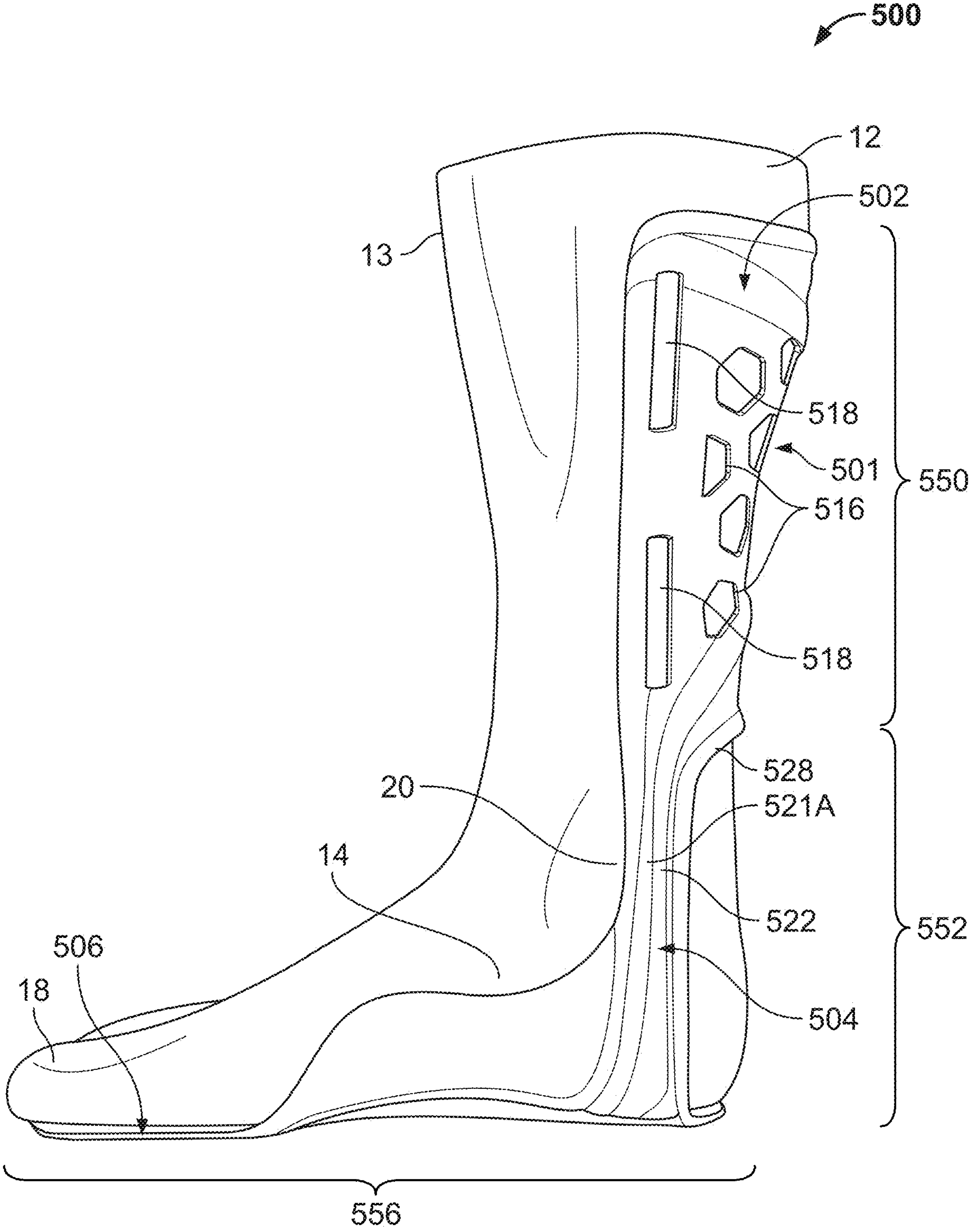
FIG. 21 is a medial side view of the AFO of FIG. 19.
Figure 22:
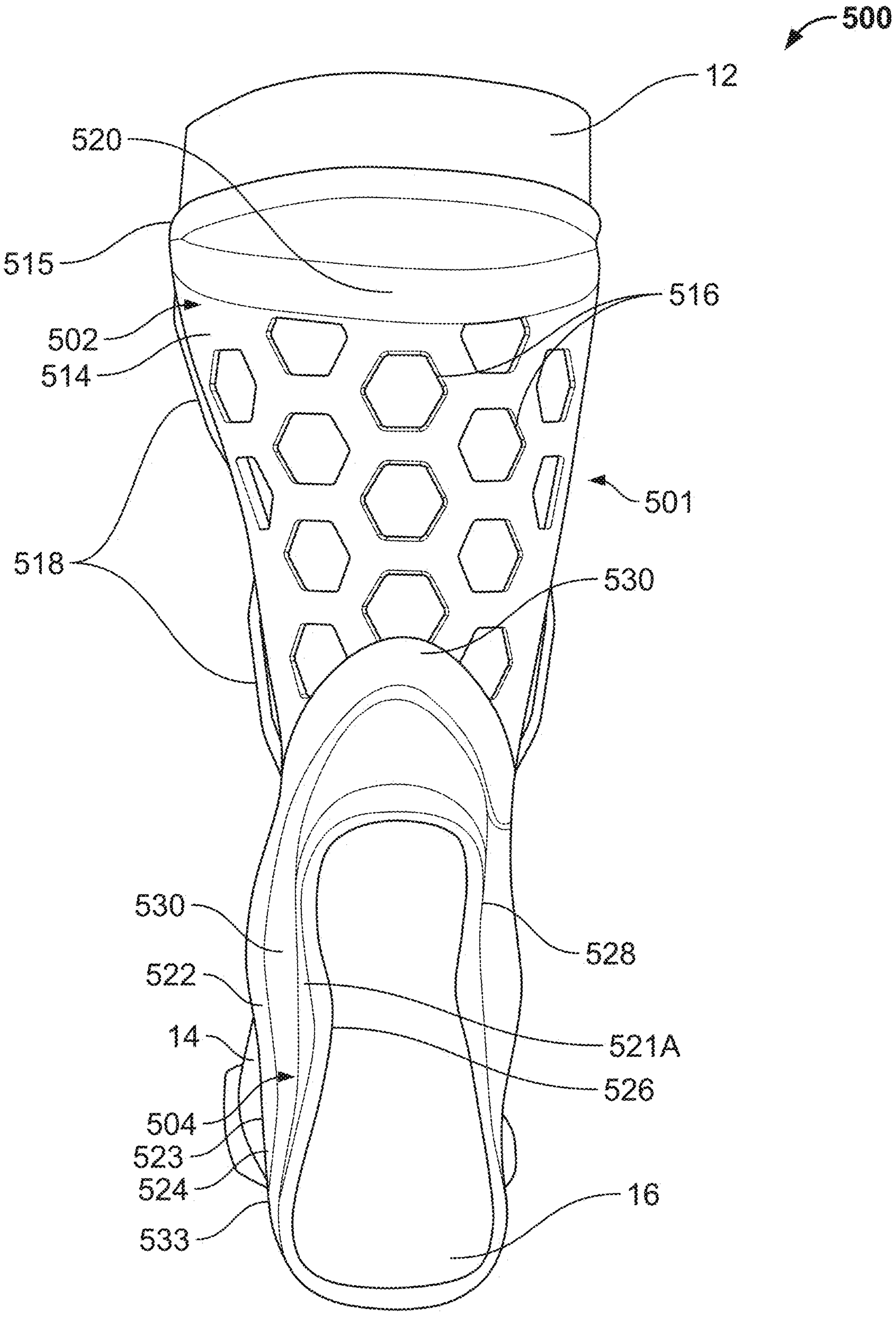
FIG. 22 is a posterior view of the AFO of FIG. 19.
Figure 23:
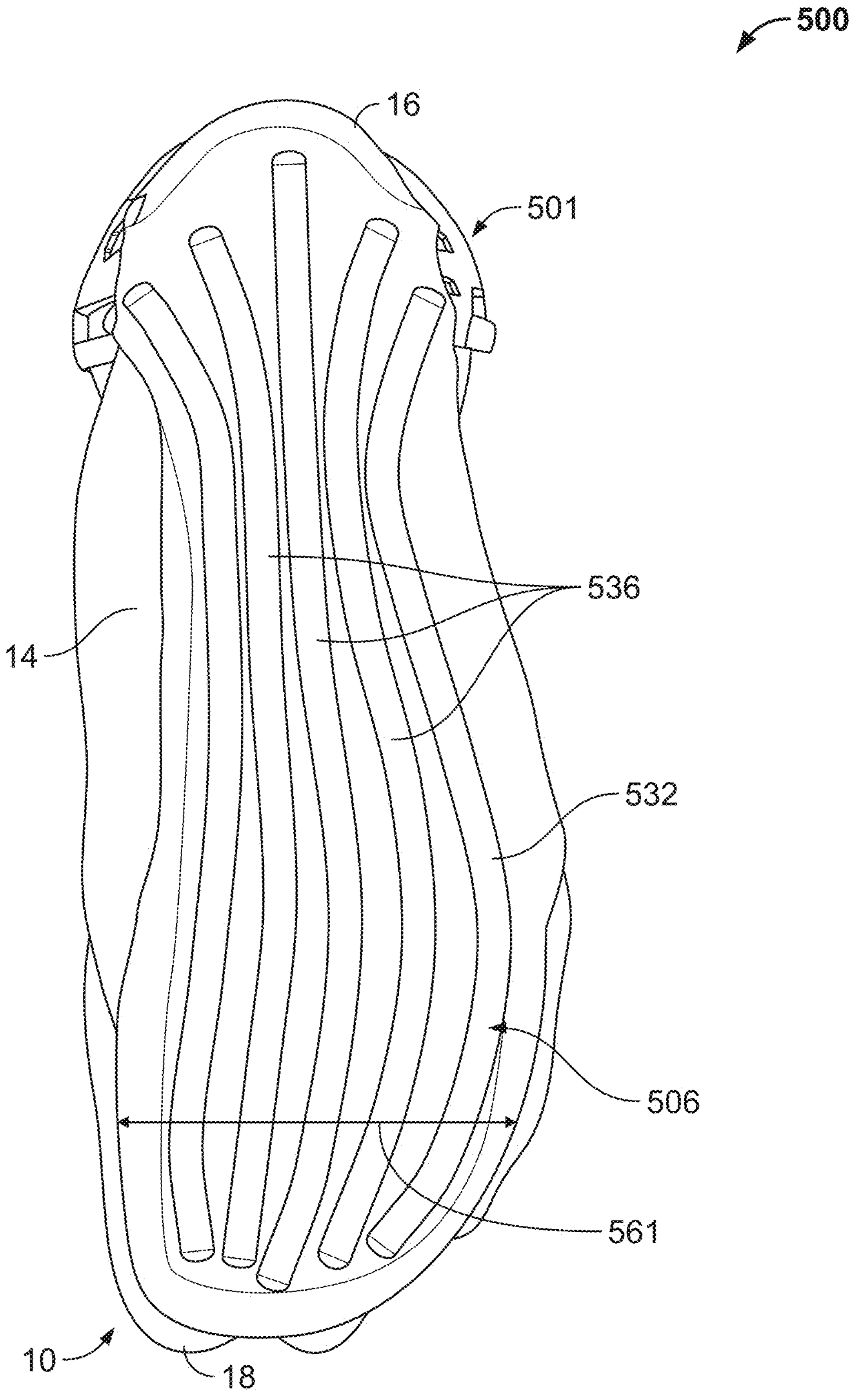
FIG. 23 is a bottom view of the AFO of FIG. 19.
Figure 24:
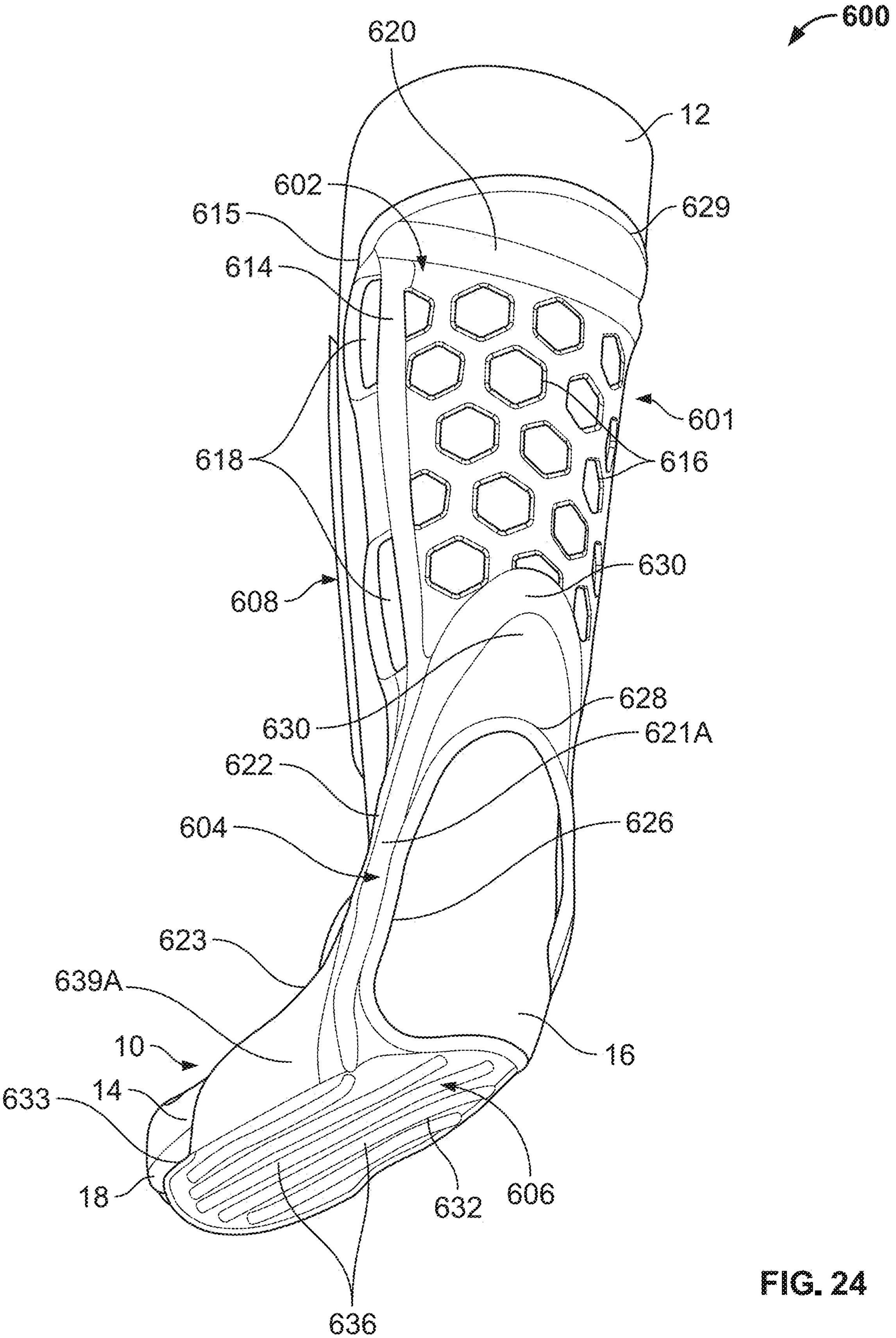
FIG. 24 is a posterior perspective view of an exemplary AFO, according to one embodiment.
Figure 25:
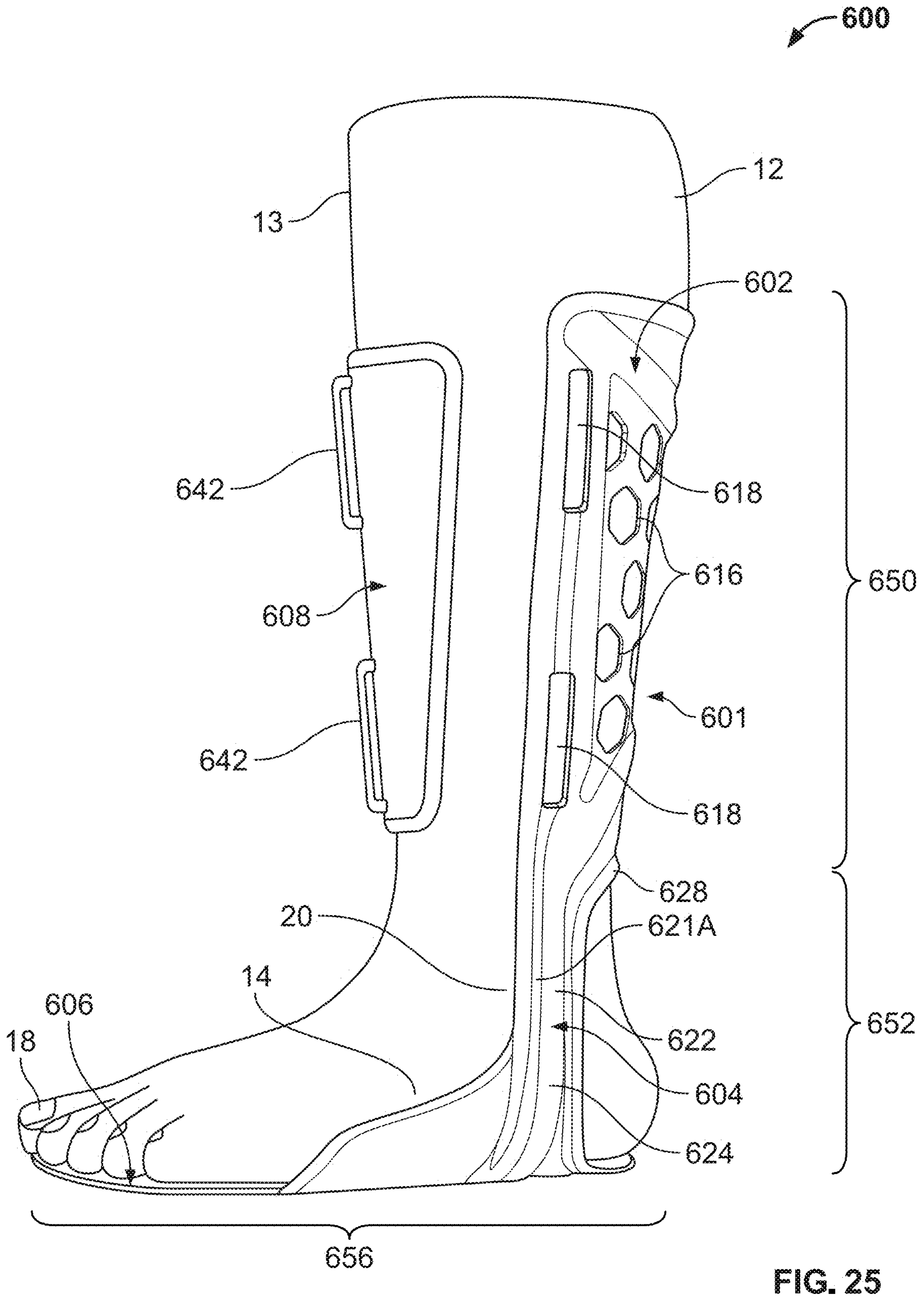
FIG. 25 is a lateral side view of the AFO of FIG. 24.
Figure 26:
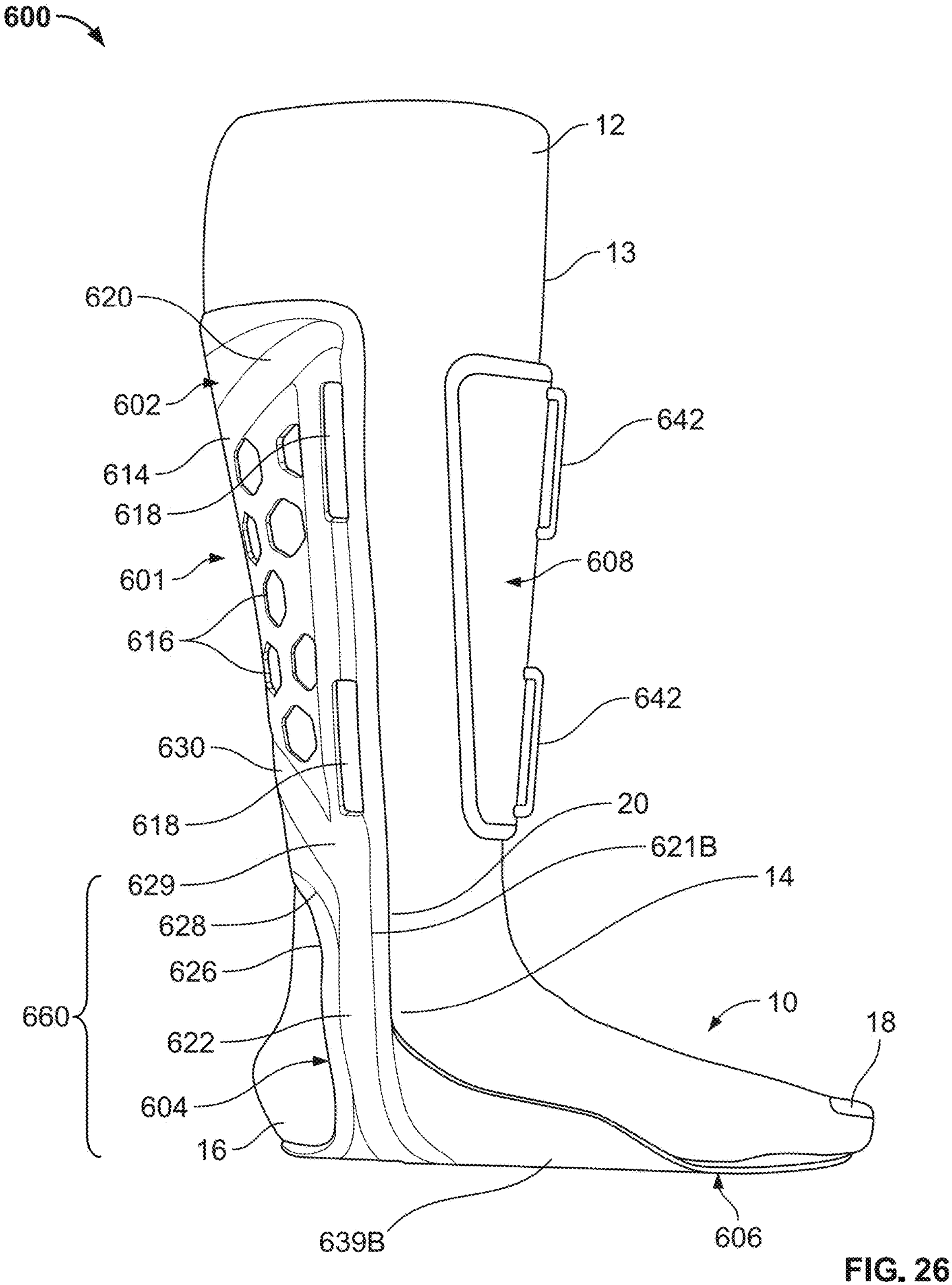
FIG. 26 is a medial side view of the AFO of FIG. 24.
Figure 27:
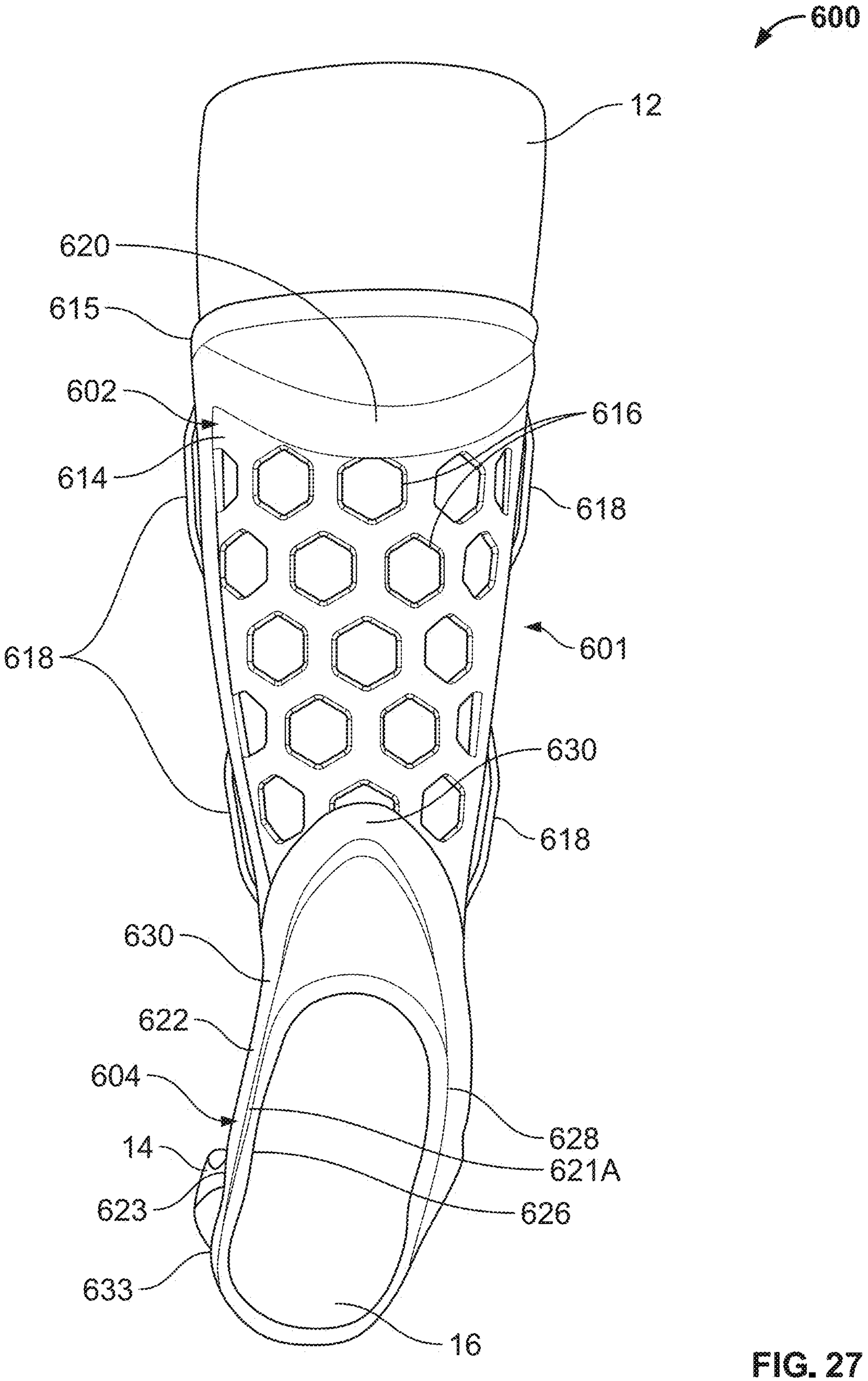
FIG. 27 is a posterior view of the AFO of FIG. 24.
Figure 28:
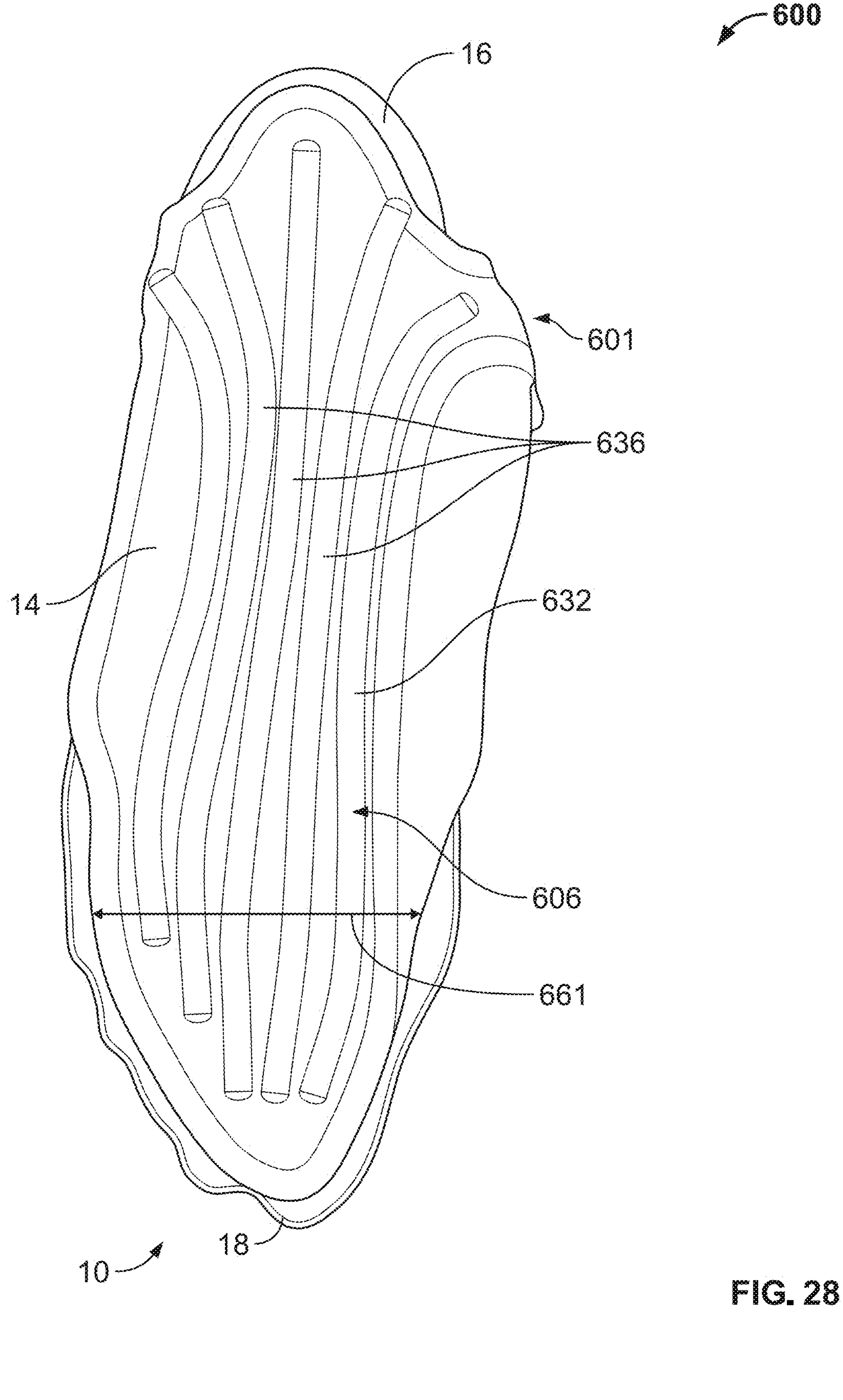
FIG. 28 is a bottom view of the AFO of FIG. 24.
Figure 29:
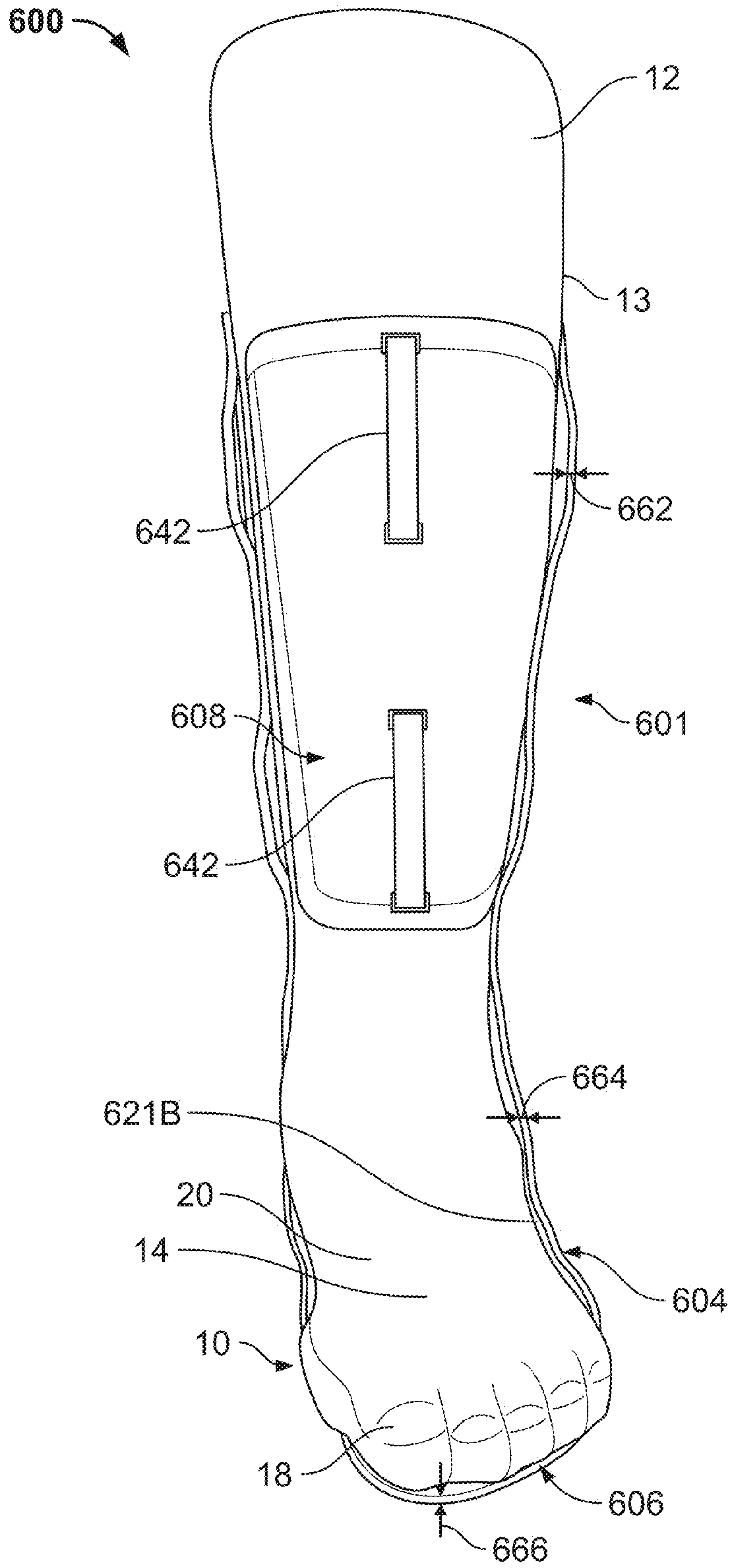
FIG. 29 is an anterior view of the AFO of FIG. 24.
Figure 30:
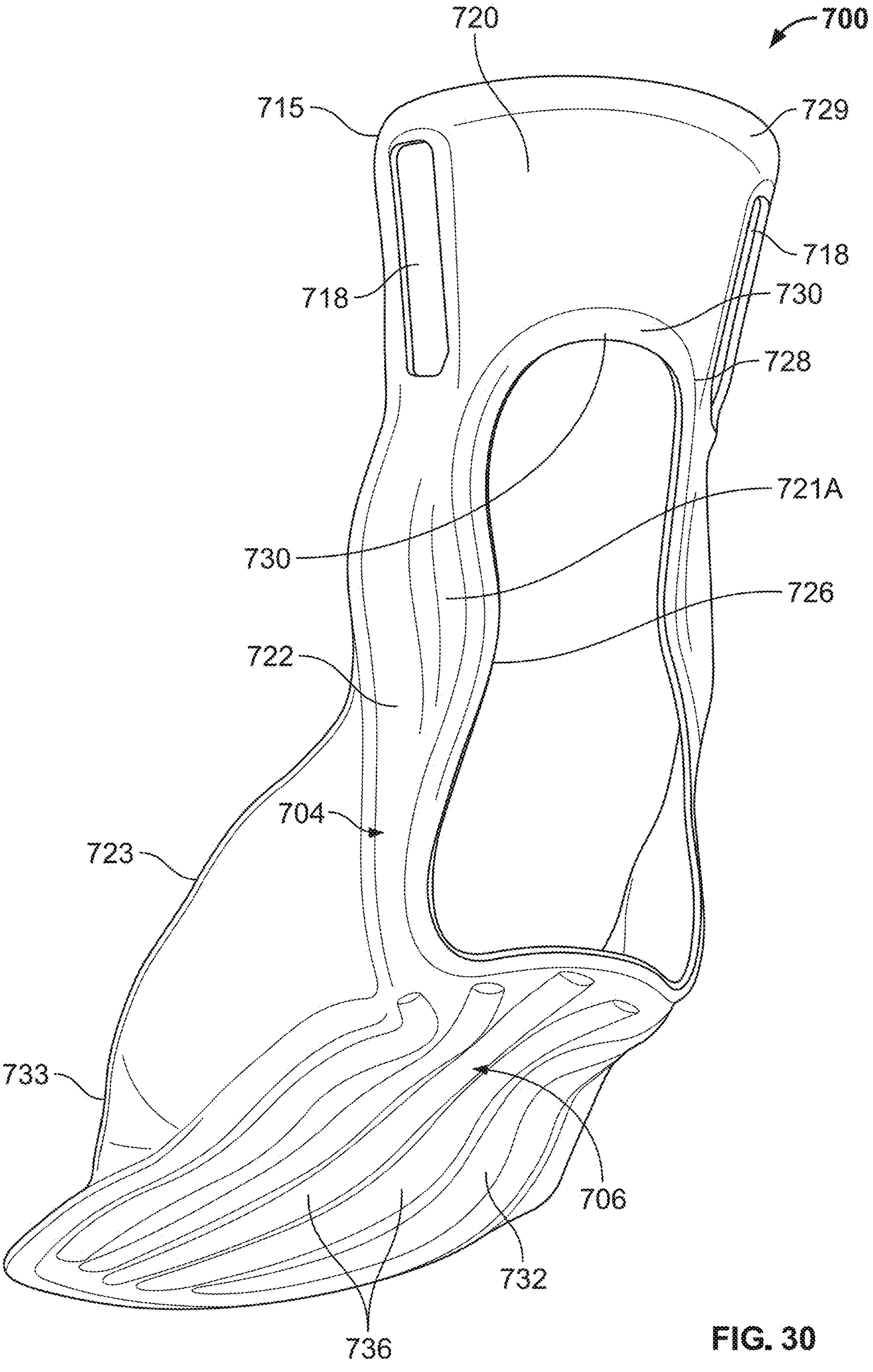
FIG. 30 is a posterior perspective view of an exemplary AFO, according to one embodiment.
Figure 31:
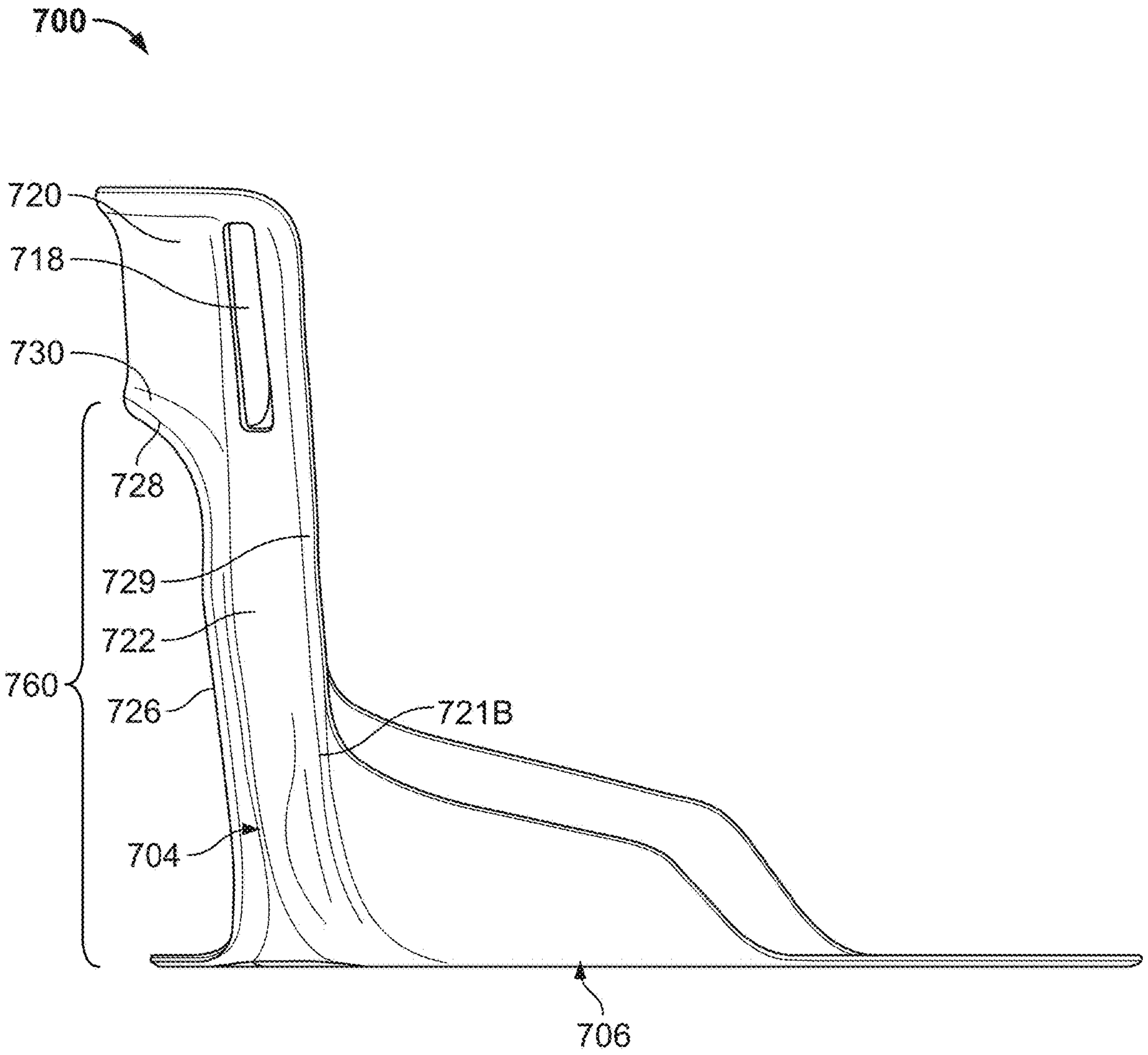
FIG. 31 is a lateral side view of the AFO of FIG. 30.
Figure 32:
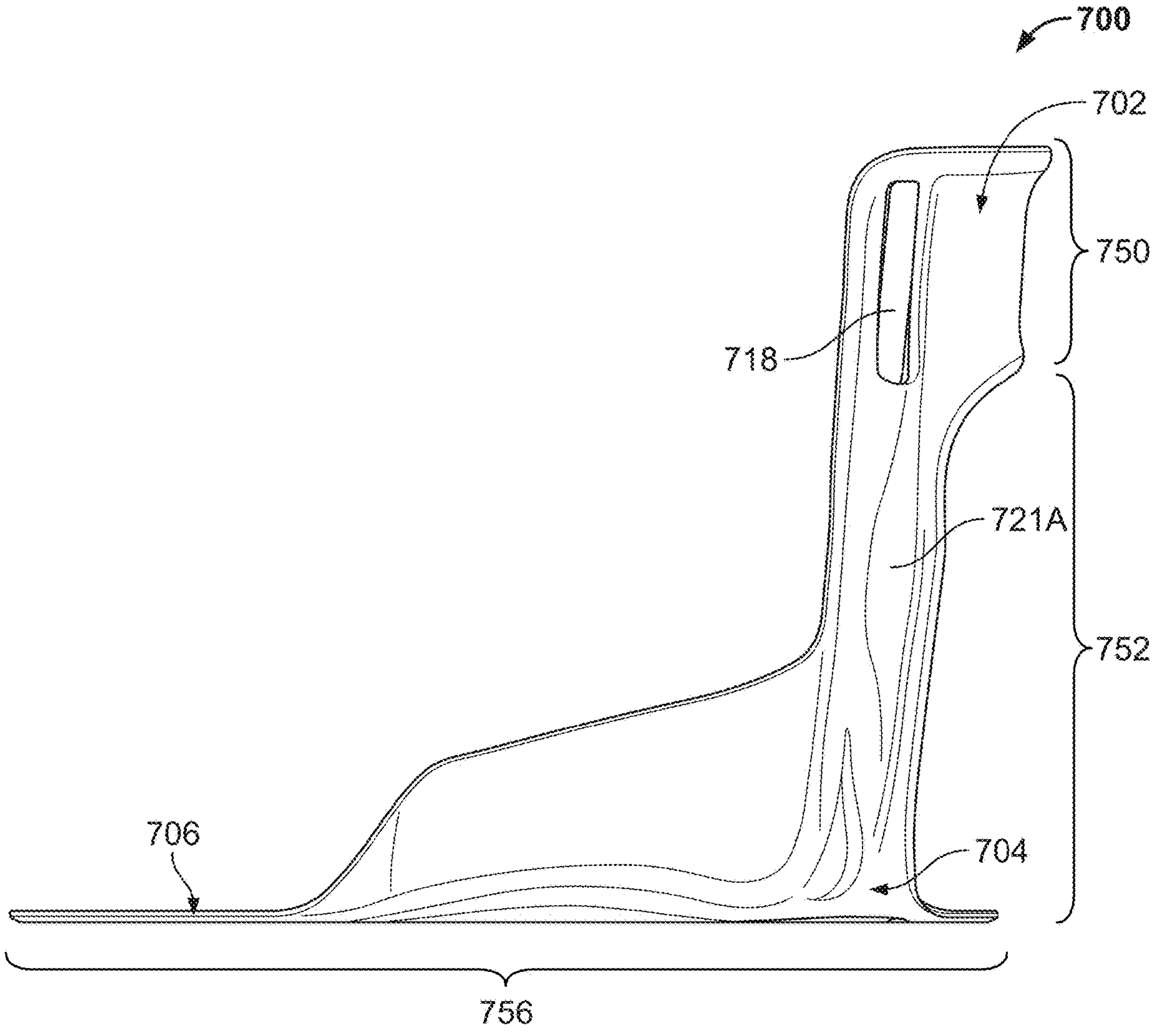
FIG. 32 is a medial side view of the AFO of FIG. 30.
Figure 33:
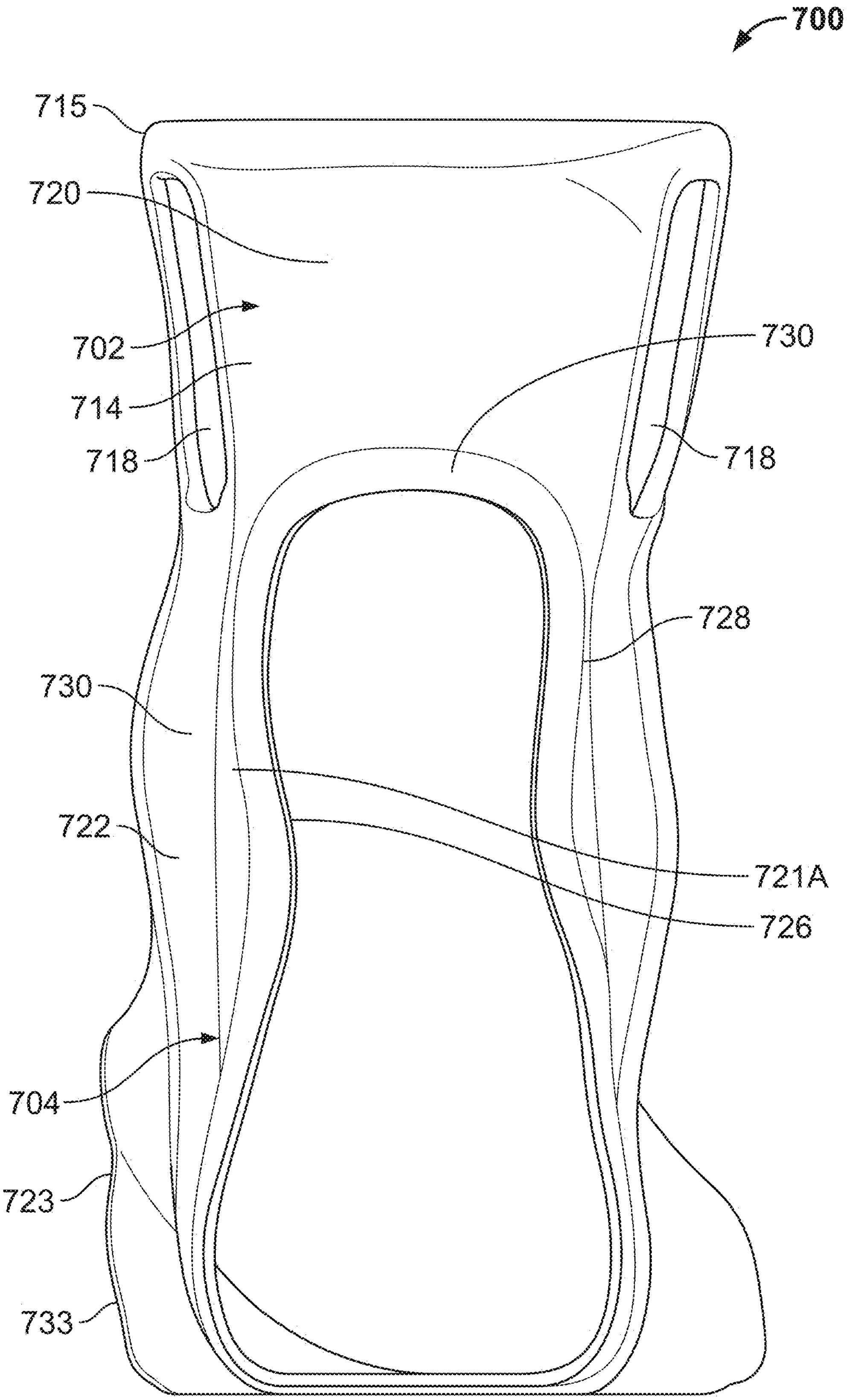
FIG. 33 is a posterior view of the AFO of FIG. 30.
Figure 34:
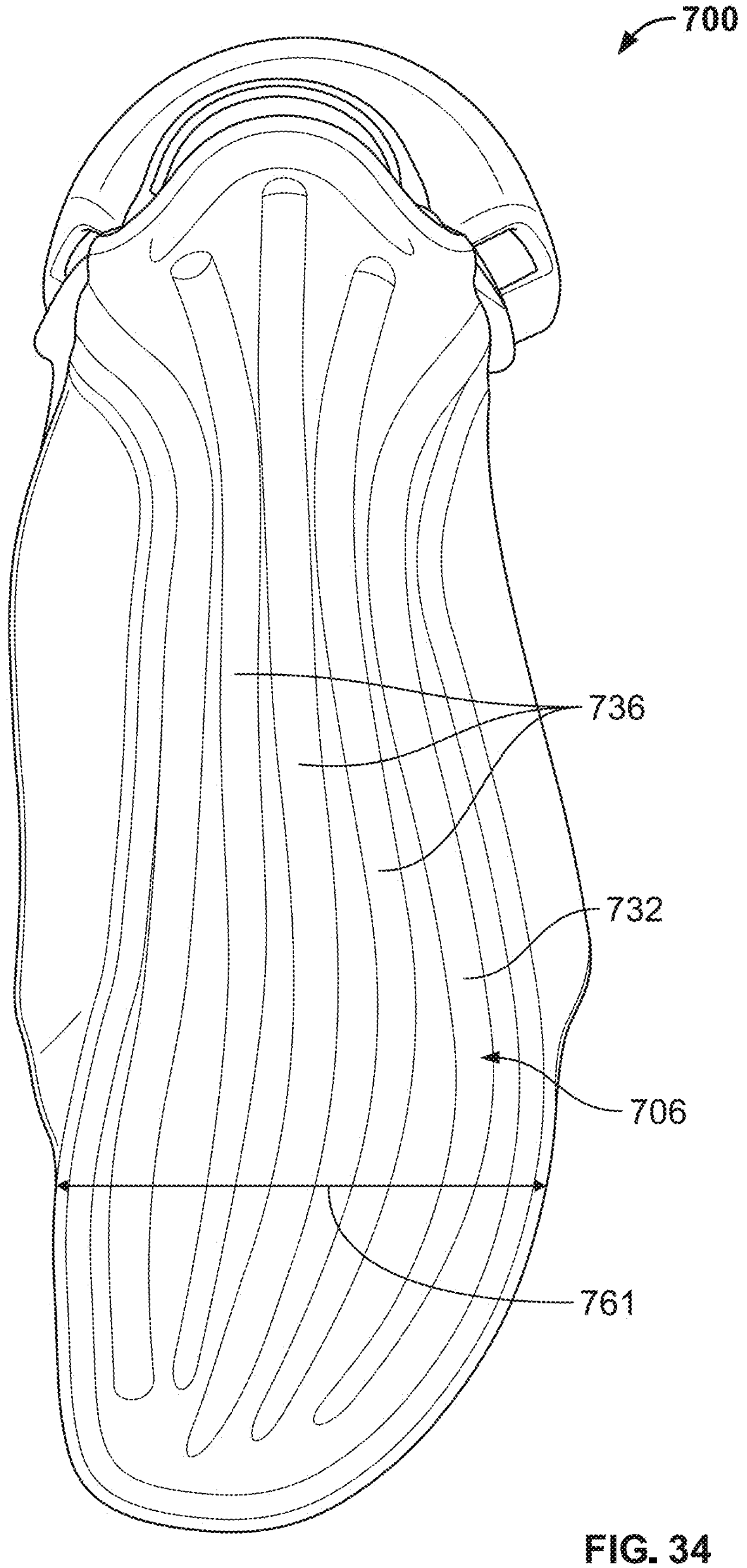
FIG. 34 is a bottom view of the AFO of FIG. 30.
Figure 35:
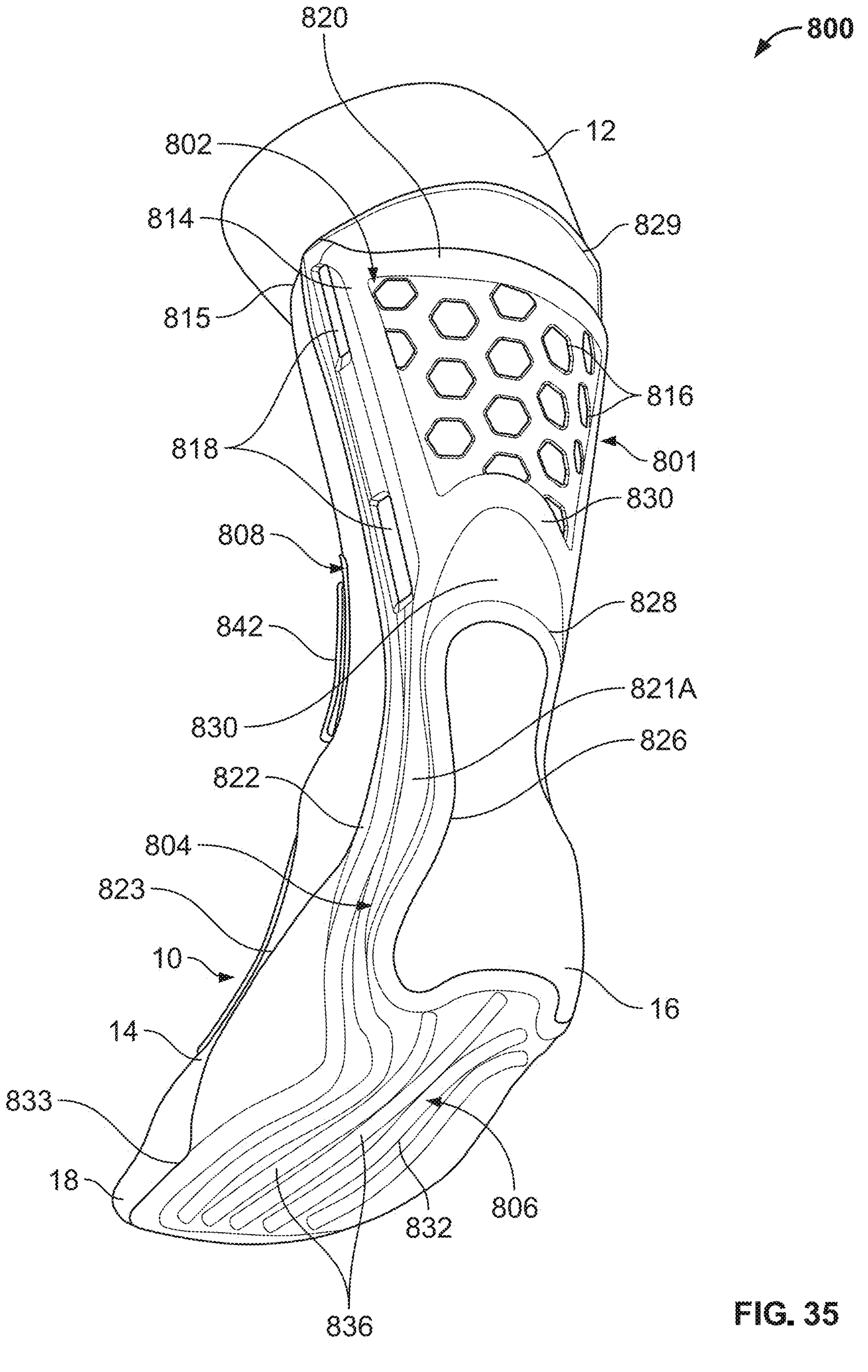
FIG. 35 is a posterior perspective view of an exemplary AFO, according to one embodiment.
Figure 36:
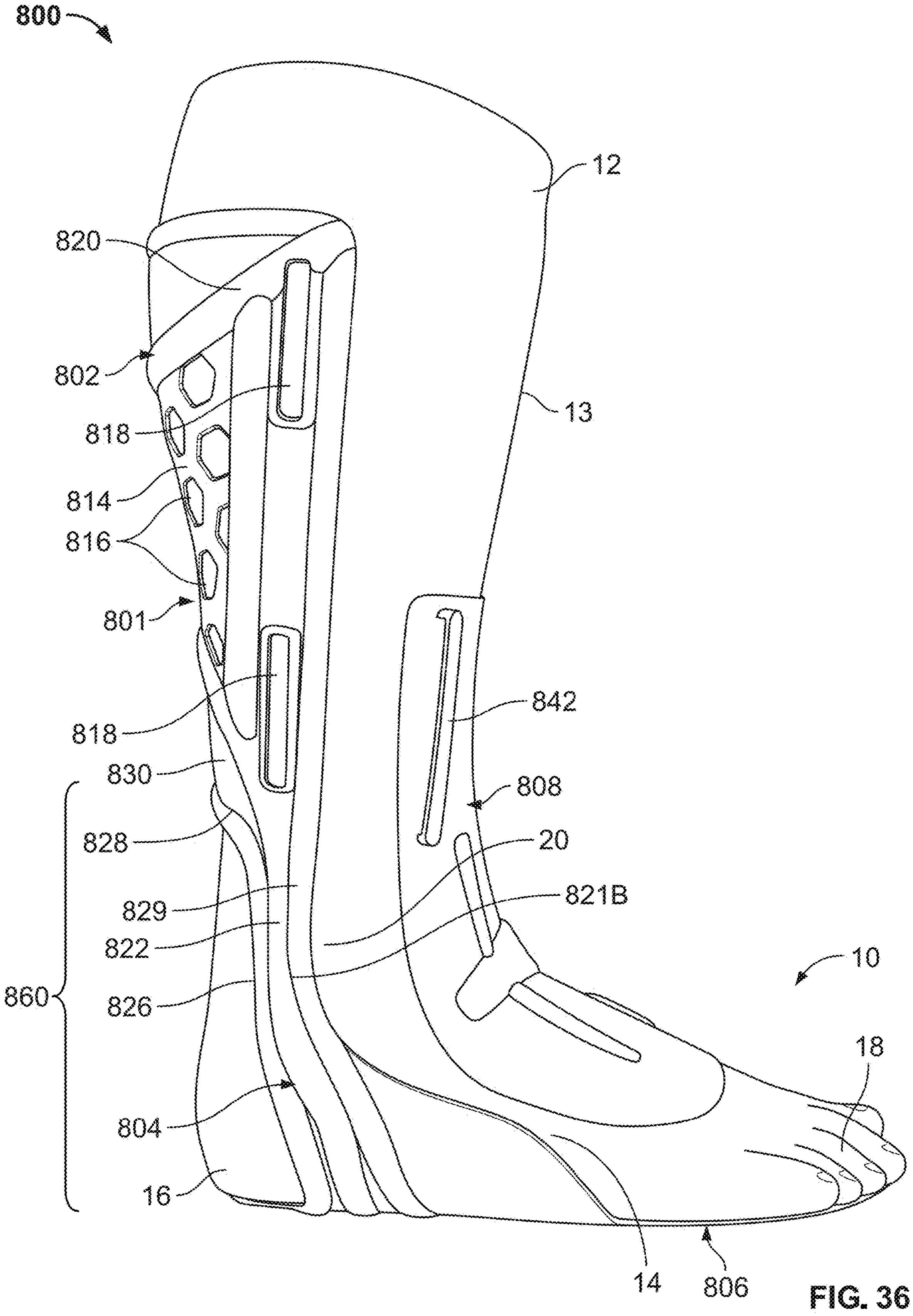
FIG. 36 is a lateral side view of the AFO of FIG. 35.
Figure 37:
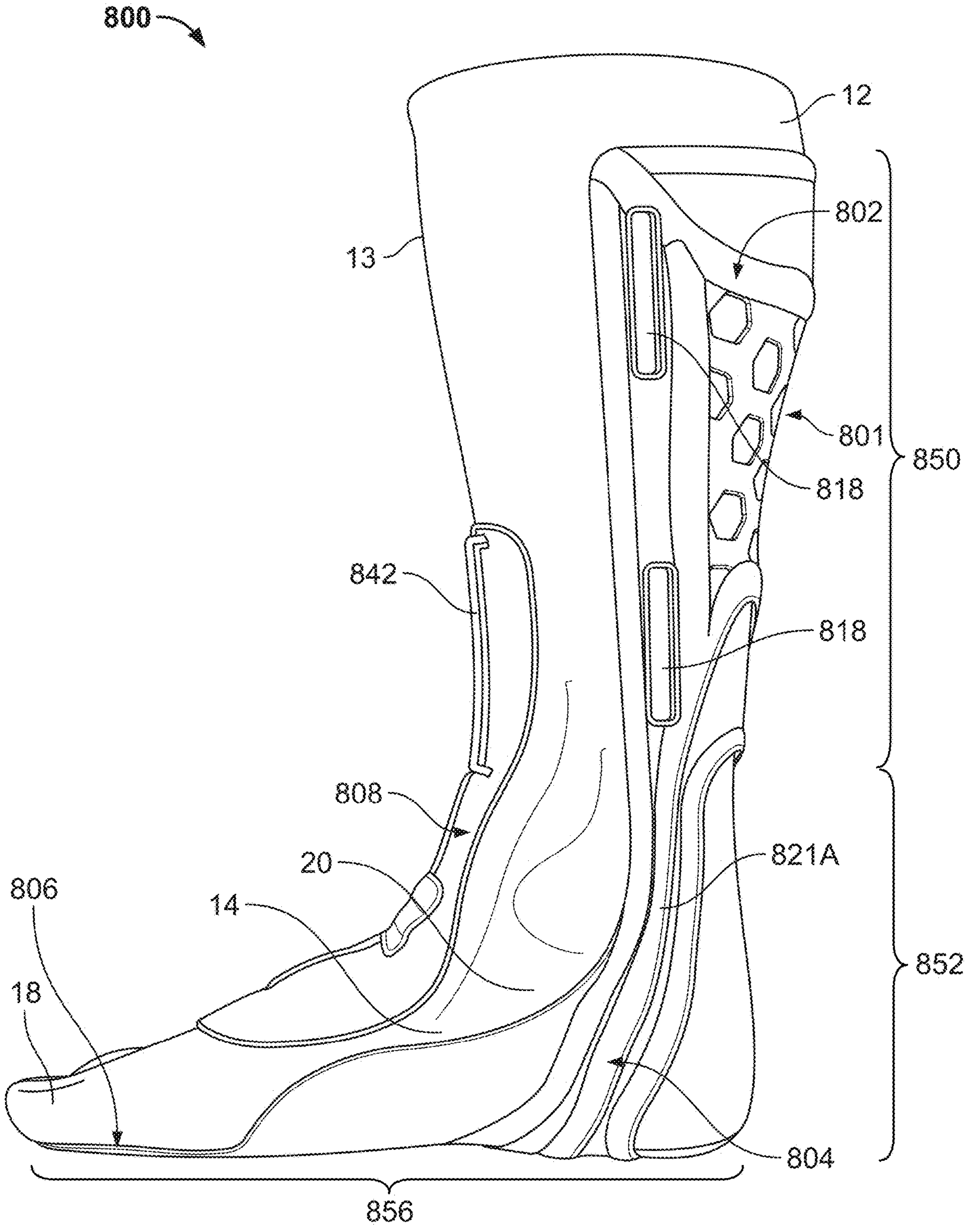
FIG. 37 is a medial side view of the AFO of FIG. 35.
Figure 38:
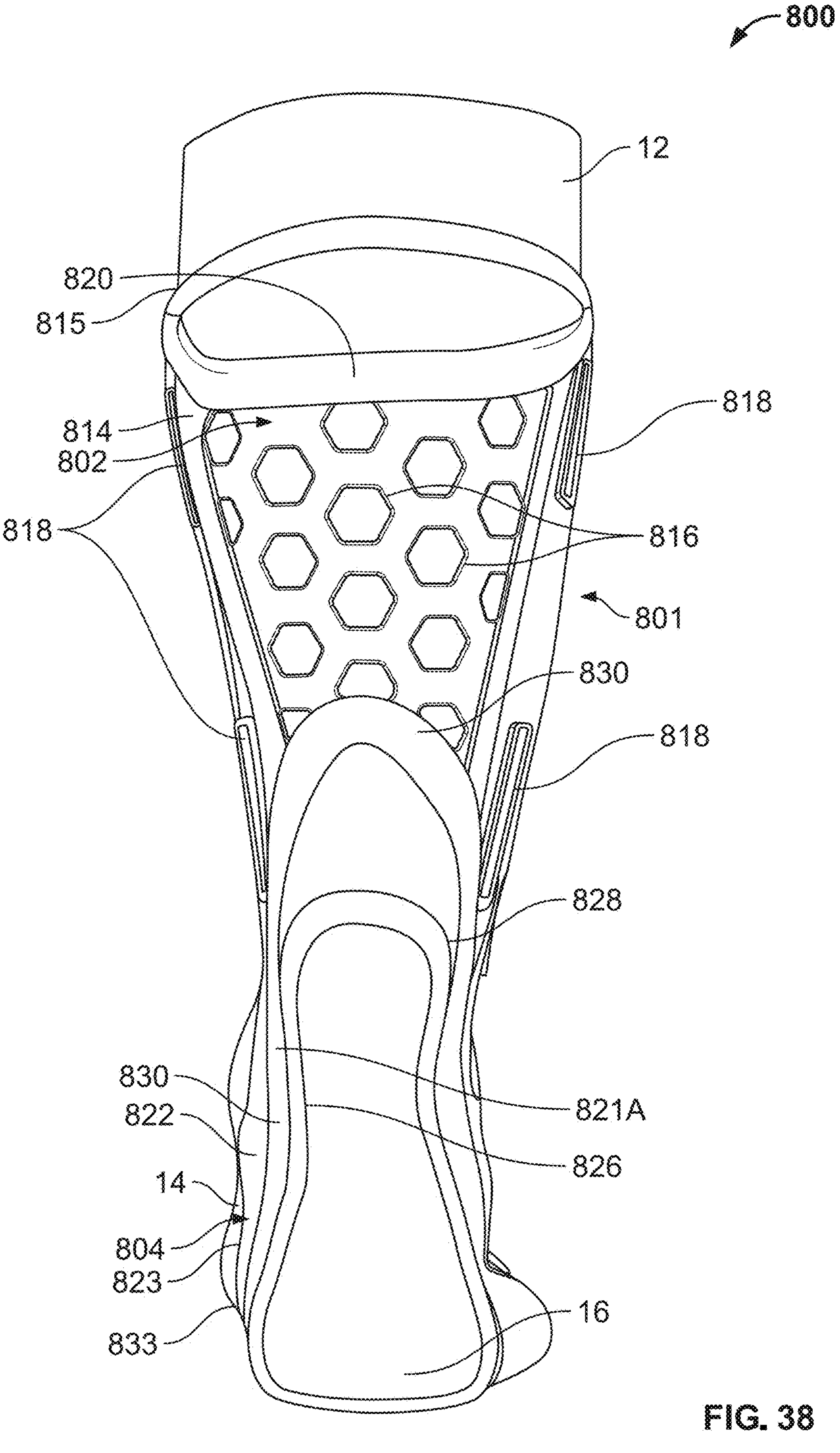
FIG. 38 is a posterior view of the AFO of FIG. 35.

With particular reference to FIG. 1E, one embodiment of a structural band configuration for an AFO is shown positioned in the relation to a lower leg 10 of a patient. Here, the structural band configuration can include one or more structural bands provided in the form of one or more gait-oriented structural bands 140, 142. For instance, the gait-oriented structural bands 140, 142 can extend along the plantar surface of the foot 14, oriented in the direction of gait, to strategically provide flexibility and rigidity during gait (and to facilitate a natural gait pattern).

The gait-oriented structural bands 140, 142 can include peripheral gait-oriented structural bands 140 and a center gait-oriented structural band 142. The center gait-oriented structural band 142 can be oriented along a path of maximum pressure during gait that extends from the patient's Achilles tendon to the center of the midfoot/base of the third metatarsal head, and then curves medially towards the first toc. As the patient walks, the heel can strike the ground before the midfoot and toes, and the corresponding energy/pressure can transfer from the heel to the midfoot to the first and/or second toes. Thus, via the gait-oriented structural bands 140, 142, the footplate can strategically bend during the gait cycle to transmit force and provide spring-back along a natural/patient-specific path of the foot's bending motion.

Further, the gait-oriented structural bands 140, 142 can include an added width to the base width of the AFO of about at least 2.0 mm to 3.0 mm, or about at least 2.5 mm to 3.5 mm, or about at least 3.0 mm to 4.0 mm, or about at least 3.5 mm to 4.5 mm, or about at least 4.0 mm to 5.0 mm, or about at least 4.5 mm to 5.5 mm, or about at least 5.0 mm to 6.0 mm. Further, the gait-oriented structural bands 140, 142 can include an added thickness to the baseline thickness of about at least 1.0 mm to 2.0 mm, or about at least 1.5 mm to 2.5 mm, or about at least 2.0 mm to 3.0 mm, or about at least 2.5 mm to 3.5 mm, or about at least 3.0 mm to 4.0 mm from the outer surface of the footplate.

In some embodiments, the footplate can include between about at least 4 to 7, or about at least 5 to 8, or about at least 6 to 9, or about at least 7 to 10 gait-oriented structural bands 140, 142. In one non-limiting example, the gait-oriented structural bands 140, 142 can be thickened and widened to account for larger shoe sizes. Overall, the gait-oriented structural bands 140, 142 can increase stiffness at the plantar surface of the foot 14 to provide resistance against plantarflexion, without adding increased thickness to the overall profile of the AFO, thereby reducing material weight of the AFO and allowing the foot 14 (and thus footplate) to bend during gait.

According to various embodiments, it will be understood that, as described herein, one or more of the patient-specific AFOs can include any suitable combination, orientation, number, and positioning of the one or more structural bands, among other features.

Referring now to FIGS. 2-8, one embodiment of an exemplary AFO 200 is shown. In this embodiment, the AFO 200 comprises a body 201 designed to selectively engage with a lower leg 10 of a patient (wherein the lower leg 10 includes the calf 12, the shin 13, the foot 14, the heel 16, the toes 18, and the ankle joint 20).

In some embodiments, the body 201 includes an upper support member 202, a lower support member 204, and a footplate 206. The AFO 200 can further comprise an optional anterior plate 208 positioned at an opposite side of the lower leg 10 in relation to the body 201, and which can be attached to the body 201 (and thus secured to the lower leg 10) via one or more attachment members 210, 212. In some embodiments, one or more components of the AFO 200 can substantially conform to the contour of the underlying patient anatomy. For instance, the upper support member 202 can substantially conform to an upper portion of the patient's calf 12. The lower support member 204 can substantially conform to a lower portion of the patient's calf 12 and side portions of the ankle joint 20. In certain embodiments, the footplate 206 can substantially conform to a bottom portion of the patient's foot 14, spanning from about the heel 16 to about the toes 18. In some embodiments, the anterior plate 208 can substantially conform to a portion of the patient's shin 13.

In certain embodiments, one or more of the upper support member 202, lower support member 204, footplate 206, and anterior plate 208 can be integrally formed such that the AFO 200 forms a single apparatus. In the embodiment shown, the upper support member 202, lower support member 204, and footplate 206 form the body 201 while the anterior plate 208 is removably attachable to the body 201 via the one or more attachment members 210, 212. In other embodiments, one or more of the aforementioned components can be removably attached to one another via any suitable means without departing from the principles of this disclosure.

In some embodiments, certain portions of the AFO 200 exhibit a dynamic thickness provided in the form of a baseline thickness at certain portions and an added thickness at certain other portions. The dynamic thickness may increase along regions of the AFO 200 that support or brace portions of patient anatomy (and may thus require additional strength and stability), while the dynamic thickness may remain at a baseline level (or decrease below the baseline level) along regions that facilitate joint and muscle movement. In other embodiments, the dynamic thicknesses of the support or brace portions and the baseline thickness may vary as desired without departing from the principles of this disclosure. In other words, the baseline thickness may be different at different locations on the AFO 200.

In some embodiments, the support or brace portions may similarly include variations in thickness depending on the desired performance of the AFO 200. For instance, the upper support member 202, the lower support member 204, the footplate 206, and/or the anterior plate 208 can comprise varying thicknesses to reinforce portions of the AFO 200 that selectively engage with the calf 12, foot 14, and/or ankle joint 20 (see, e.g., thicknesses 262, 264, 266 of FIG. 8). Exemplary baseline thickness ranges include about at least 1.5 mm to 5.0 mm along the various components of the AFO 200, or about at least 1.5 mm to 3.0 mm, or about at least 2.0 mm to 3.5 mm, or about at least 2.5 mm to 4.0 mm, or about at least 3.0 mm to 4.5 mm, or about at least 3.5 mm to 5.0 mm. In some embodiments, the baseline thicknesses can increase to greater than about at least 5.0 mm, as desired.

In some cases, variable factors (e.g., strut length, strut width, baseline thickness, patient size/weight and activity levels, treatment goals, etc.) can affect the thickness ranges. For example, an active and relatively heavy patient may require a thicker AFO with wider thickness ranges than a sedentary, relatively light patient who may desire a thinner device and wherein using a thinner device would not reduce the effectiveness of the AFO 200. Thus, the baseline thickness and added thickness of the AFO 200 can be varied in strategic areas to improve performance characteristics. Specifically, when the struts are created and positioned in the AFO design process, the size of the patient's medial and lateral malleoli may be considered. In one non-limiting example, the baseline thickness can be about at least 3 mm thick while one or more areas of the lower support member can reach up to at least 8 mm thick.

In some embodiments, the portions of increased thicknesses can be provided in the form of one or more structural bands (e.g., structural bands 220, 228, 229, 230, 236, 244) positioned along one or more of the upper support member 202, lower support member 204, footplate 206, and/or anterior plate 208. The one or more structural bands can further enhance the performance of the overall AFO 200 and can be designed and/or distributed along the AFO according to patient-specific considerations.

In some cases, the one or more structural bands can be hollow or partially hollow while in other embodiments, the one or more structural bands can be solid (e.g., non-hollow portions of increased material thickness). For instance, in some embodiments, the thickness variations of the structural bands and distributions of the structural bands can be determined according to 3D scans of the patient anatomy while in other embodiments, the thickness variations can be pre-selected based on injury type, treatment plan, and other use cases. Further, one or more structural bands can be designed to facilitate and improve energy transfer throughout the AFO 200 while in use.

In some embodiments, the upper support member 202 includes an overall shape that can substantially conform to the shape of at least a portion of a patient's calf 12, such that an outer surface 214 generally faces away from the patient and an inner surface 215 selectively engages with the calf 12. The outer surface 214 may comprise a durable material that can be designed to withstand long-term functionality, retain structural integrity, and protect and support the calf 12 even after prolonged use. In other embodiments, only certain portions of outer surface 214 may comprise a durable material without departing from the principles of this disclosure. The outer surface 214 can thus be constructed from materials such as, but not limited to, thermoplastics (e.g., polypropylene, polyethylene, other elastomers), carbon fiber, fiberglass, aluminum, stainless steel, kevlar, nylon, acrylic resins, or any other suitable materials or combinations thereof. The inner surface 215 can cover or partially cover the posterior, medial, and/or lateral portions of the calf 12 to provide a cushioning effect, reduce irritation, and enhance patient comfort. In some cases, the inner surface 215 can be provided with a soft inner material such as, but not limited to, foam (e.g., plastazote, aliplast), neoprene, ethylene vinyl acetate (EVA), gel inserts, leather/synthetic leather, felt, poron, fabric, or any other suitable materials or combinations thereof. Soft materials can be positioned or concentrated at high-pressure areas on the inner surface 215 that may be adjacent to bony patient anatomy regions.

In some embodiments, the upper support member 202 includes a plurality of through-holes extending between the outer surface 214 and the inner surface 215, provided in the form of one or more attachment openings 218. The one or more attachment openings 218 can be positioned at about the medial and lateral edges of the upper support member 202. In some embodiments, the one or more attachment openings 218 can be provided in the form of eyelets (e.g. punched eyelets, webbed eyelets, etc.), D-Rings, slots, or any other suitable structure or combination of structures thereof.

In some embodiments, the one or more attachment openings 218 can be integrally formed with the upper support member 202 while in other embodiments, the one or more attachment openings 218 can be provided as a separate component attached to the upper support member 202. The one or more attachment openings 218 receive the one or more attachment members 210, 212 such that the one or more attachment members 210, 212 can be wrapped around portions of the lower leg 10. This can adjustably secure the upper support member 202 to the lower leg 10.

Similarly, the one or more attachment members 210, 212 can adjustably secure the anterior plate 208 to the shin 13 via one or more attachment slots 242 such that a position of the anterior plate 208 relative to the body 201 is dynamically fixed. In this way, arrangement of and compression by the one or more attachment members 210 can improve pressure distribution on the lower leg 10 and localize bend to the ankle joint 20.

Further, the one or more attachment members 210, 212 can provide additional flexibility to adjust the compressive effect (or "fit") of the AFO 200, thereby adapting to changes in swelling and/or lifestyle of the patient. The one or more attachment members 210, 212 can be provided in the form of straps, laces, VELCRO®, hooks, or any other suitable attachment mechanisms or combinations thereof.

For instance, the one or more attachment members 210, 212 can comprise a superior attachment member 210 attached to the upper support member 202 and positioned around about an upper portion of the patient's shin 13, and an inferior attachment member 212 attached to the upper support member 202 and positioned around about a lower portion of the patient's shin 13. The superior attachment member 210 can be designed to secure the AFO 200 against the underlying gastrocnemius muscle of the shin 13, and the inferior attachment member 212 can be designed to secure the AFO 200 to above the malleolus of the ankle joint 20. In this way, a combination of the superior and inferior attachment members 210, 212 can improve pressure distribution on the lower leg 10 and localize bend to lower support member 204 engaging the ankle area, thereby increasing patient comfort while wearing the AFO 200.

Although the embodiment shown depicts the one or more attachment members 210, 212 wrapping around the patient's shin 13 and connecting the anterior plate 208 with the upper support member 202, other embodiments can involve alternative positioning for the one or more attachment members 210, 212 based on patient-specific needs. For example, the inferior attachment member 212 can be attached to the footplate 206 and positioned around about the patient's foot 14 while the superior attachment member 210 can remain positioned around about a portion of the patient's shin 13.

In some embodiments, the upper support member 202 can include an additional plurality of through-hole openings extending between the outer surface 214 and the inner surface 215, provided in the form of open cell structures, or one or more ventilation holes 216. In some embodiments, the one or more ventilation holes 216 can be positioned in areas of lower stress where minimal forces are transmitted, while in other embodiments, the one or more ventilation holes 216 can be positioned at about higher pressure/bony areas to reduce chafing (e.g., the malleolus). The one or more ventilation holes 216 can improve breathability for and circulation in the lower leg 10 and reduce the overall weight of the AFO 200, thereby providing a low profile alternative to conventional AFOs and enhancing overall patient comfort. Additionally, the one or more ventilation holes 216 can be bound (e.g., superiorly, inferiorly, medially, and/or laterally) by one or more structural bands, such as the structural bands described with reference to FIGS. 1A-E. For instance, the one or more structural bands that bound the one or more ventilation holes 216 can include medial and lateral edge structural bands 221A, 221B (see, e.g., FIG. 1A) and/or upper and lower crossing structural bands 220, 230 (see, e.g., FIG. 1D).

Further, the one or more ventilation holes 216 can be formed from a unit cell with a radius of about at least 10.0 mm to 15 mm, or about at least 12.0 mm to 17.0 mm, or about at least 15.0 mm to 18.0 mm, or about at least 17.0 mm to 22.0 mm, or about at least 20.0 mm to 25.0 mm, or about at least 22.0 mm to 27.0 mm, or about at least 25.0 mm to 30.0 mm. Each unit cell may be set apart by at least about 5.0 mm to 7.0 mm, or about at least 6.0 mm to 8.0 mm, or about at least 7.0 mm to 9.0 mm, or about at least 8.0 mm to 10.0 mm, or about at least 9.0 mm to 11.0 mm, or about at least 10.0 mm to 12.0 mm, thereby conferring balanced stiffness and breathability to the body 201 of the AFO 200. According to some embodiments, the unit cell of the one or more ventilation holes 216 can include a shape that is substantially circular, elliptical, pentagonal, hexagonal, octagonal, or any other suitable shape. Thus, the number, sizing, positioning, spacing, and shape of the one or more ventilation holes 216 can be determined according to patient-specific considerations, and the one or more ventilation holes 216 can form a patient-specific pattern or distribution along the body 201.

In some embodiments, the upper support member 202 includes a length 250 (see, e.g., FIG. 5) that can vary depending on the size and expected activity levels of the patient, severity of the lower leg injury, and comfort. In some cases, the length 250 can extend between about the foot 14 or ankle joint 20 to about the mid-calf 12 range while in other cases, the length 250 can be increased or decreased to address patient-specific concerns. Generally, the length 250 selected can provide desirable support, control, and stability to the lower leg 10 by beneficially distributing forces during gait or other weight-bearing activities. In one non-limiting example, a shorter length 250 can be beneficial in cases of chronic ankle injuries, wherein dynamic bracing may be desirable (see, e.g., FIGS. 14 to 18).

Further, the upper support member 202 can be provided with a dynamic thickness 262 (see, e.g., FIG. 8) that includes a varyingly distributed added thickness to the baseline thickness of the AFO 200 such that the outer surface 214 can at least partially include one or more structural bands. For instance, the one or more structural bands can include medial and lateral edge structural bands 221A, 221B (see, e.g., FIGS. 1A, 1B), inner and outer perimeter structural bands 228, 229 (see, e.g., FIG. 1C), and/or upper and lower crossing structural bands 220, 230 (see, e.g., FIG. 1D).

In some cases, each of the edge structural bands 110, 112 can extend from a top portion of the upper support member 202, down a length of the lower support member 204 on the medial and lateral sides of the ankle joint 20, and to proximal the toc portion of the footplate 206. In some cases, the outer perimeter structural band 229 can extend along the overall perimeter of the AFO 200 (including portions of the upper support member 202, lower support member 204, and footplate 206), and the inner perimeter structural band 228 can extend along a perimeter of one or more structural features positioned on the body 201 (e.g., posterior opening 226). In some cases, the upper crossing structural band 220 can extend across about a top portion of the upper support member 202, and the lower crossing structural band 230 can extend around about a lower portion of the upper support member 202 and/or upper portion of the lower support member 204.

In some embodiments, the lower support member 204 includes an overall shape that can substantially conform to the shape of at least a portion of the patient's ankle joint 20, while connecting the upper support member 202 with the footplate 206. As shown, an outer surface 222 generally faces away from the patient and an inner surface 223 selectively engages with the ankle joint 20. The outer surface 222 can comprise a durable material (e.g., nylon, etc.) to protect and support the ankle, similar to the material of the outer surface 214. In other embodiments, only certain portions of outer surface 222 may comprise a durable material without departing from the principles of this disclosure. The inner surface 223 can cover or partially cover the posterior, medial, and/or lateral portions of the ankle joint 20. In some cases, the inner surface 223 can be provided with a soft inner material, similar to the inner surface 215. Soft materials can be positioned or concentrated around about high-pressure areas on the inner surface 223 that may be adjacent to bony patient anatomy regions.

In some embodiments, the lower support member 204 can be designed to bend and flex about the ankle joint 20 in a patient-specific manner. For instance, the upper support member 202 (in combination with the anterior plate 208) stabilizes the upper portion of the lower leg 10, thereby driving bending forces at the lower support member 204. In this way, as the patient undergoes the gait cycle, ground force reaction can be elicited while inversion, eversion, dorsiflexion, plantarflexion, and/or horizontal rotation of the ankle-foot complex can be controlled. In some embodiments, the AFO 200 can reduce the force required during gait by the patient (e.g., "offloading") to plantarflex and/or dorsiflex the ankle joint 20, wherein the force required can depend on patient-specific factors such as height, weight, and/or pathology to be treated. In particular, the AFO 200 can offload forces during gait by about at least 0% to 20%, or about at least 10% to 30%, or about at least 20% to 40%, or about at least 30% to 50%, or about at least 40% to 60%, or about at least 50% to 70%, or about at least 60% to 80%, or about at least 70% to 90%, or about at least 80% to 100%. In some cases, the AFO 200 can offload forces during gait by about 20% to 50%, or about 20% to 80%.

In some embodiments, the lower support member 204 can be rigidly formed or connected with the upper support member 202 and the footplate 206 such that reduced ankle movement occurs, thereby providing improved coverage along about a posterior portion of the lower leg 10. In other embodiments, the lower support member 204 can be integrally formed with the body 201 such that the upper support member 202 gradually transitions into the lower support member 204, which gradually transitions into the footplate 206. In particular, the lower support member 204 can be arranged within the AFO 200 to avoid engaging with bony prominences (e.g., medial and lateral portions of the ankle joint 20, the malleolus, etc.) and provide lift away from the lower leg 10.

In some embodiments, the lower support member 204 can be provided in the form of one or more struts positioned at about the medial and lateral sides of the ankle joint 20. The one or more struts can be designed to provide durability and flexibility to replicate a natural gait pattern (e.g., "bend" and "spring back"). Further, the one or more struts can be designed to withstand cyclic loading for long-term use and may flex according to factors such as size, shape, material, and orientation. For example, the one or more struts may be lofted from the malleolus portion of the ankle joint 20 in order to increase comfort and decrease possible impingement points.

In certain embodiments, mesh relaxation with minimal surface optimization may be used to decrease curvature and stress concentrations. The one or more struts generally follow the shape of the lower calf 12/ankle joint 20, thereby allowing a relatively comfortable fit within a shoe. The one or more struts may be positioned with varying angulation, such as at about at least 10.0 to 20.0 degrees, or about at least 15.0 to 25.0 degrees, or about at least 20.0 to 30.0 degrees, or about at least 25.0 to 35.0 degrees, or about at least 30.0 to 40.0 degrees from vertical. In some embodiments, the one or more struts can include one or more structural bands (e.g., medial edge structural band 221A, lateral edge structural band 221B) designed to support repeated bending motions.

In some embodiments, the one or more structural bands can allow the one or more struts to flex and bend, thereby propelling the patient forward during gait. In an embodiment, the lower support member 204 can include two struts each having three structural thickness bands, provided in the form of edge thickness bands designed to prevent crack propagation at the edges of the AFO 200 and a center thickness band designed to provide strength during gait. The one or more struts can be shaped to support gait and bend according to a patient-specific gait pattern.

In some embodiments, the lower support member 204 can be provided in the form of a hinged connection extending between the upper support member 202 and the footplate 206 while in other embodiments, the lower support member 204 can function as a hinge between the upper support member 202 and the footplate 206. Thus, the lower support member 204 can improve plantarflexion and dorsiflexion of a patient's foot 14 by providing controlled spring action about a patient's ankle joint 20. In certain embodiments, the lower support member 204 can be adjustable via an alignment adjustment hex or plantarflexion/dorsiflexion adjustment channels, wherein loosening and tightening of the alignment adjustment hex and/or adjustment channels may alter the range of movement as treatment progresses.

In some embodiments, the lower support member 204 includes a length 252 (see, e.g., FIG. 5) that can vary depending on the size and expected activity levels of the patient, severity of the lower leg injury, and comfort. In some cases, the length 252 can extend from about the middle to lower portion of the calf 12 to the foot 14 while in other cases, the length 252 can be increased or decreased to address patient-specific concerns.

In some cases, the lower support member 204 can be arranged such that the body 201 includes a through-hole provided in the form of a posterior opening 226. The posterior opening 226 can be positioned in a region substantially between the transition from the upper support member 202 and the lower support member 204. The posterior opening 226 can allow the patient's heel 16 to at least partially protrude from the body 201, which may enhance overall patient comfort (e.g., improve breathability and reduce heat retention) while allowing the AFO 200 to feel relatively lightweight. In certain embodiments, sizing (e.g., length, weight, shape) of the posterior opening 226 can be designed according to patient-specific considerations.

In certain embodiments, the posterior opening 226 can include a generally triangular or elliptical shape. Further, the posterior opening 226 can include a length 260 that can be increased relative to length 252 in cases where some movement of the ankle joint 20 is desirable, or decreased relative to the length 252 of the lower support member 204 in cases where immobilization of the ankle joint 20 is desirable (see, e.g., FIGS. 4 and 5). Further, in some embodiments, the posterior opening 226 can include an increased edge thickness provided in the form of inner perimeter structural bands 228.

Additionally, the lower support member 204 can be provided with a dynamic thickness 264 (see, e.g., FIG. 8) that includes a varyingly distributed added thickness to the baseline thickness of the AFO 200 such that the outer surface 222 can at least partially include one or more structural bands that extend between the upper support member 202 and the lower support member 204 to the footplate 206. For instance, similar to the discussion with reference to the upper support member 202, the one or more structural bands can include medial and lateral edge structural bands 221A, 221B (see, e.g., FIGS. 1A, 1B), inner and outer perimeter structural bands 228, 229 (see, e.g., FIG. 1C), and/or lower crossing structural bands 230 (see, e.g., FIG. 1D).

In some embodiments, the footplate 206 includes an overall shape that substantially conforms to the shape of at least a portion of the patient's foot 14, such that an outer surface 232 generally faces away from the patient and an inner surface 233 selectively engages with the plantar surface of the foot 14. The outer surface 232 can comprise a durable material to protect and support the foot 14, similar to the material of the outer surface 214, such that the footplate 206 is relatively rigid. In other embodiments, only certain portions of outer surface 232 may comprise a durable material without departing from the principles of this disclosure. The inner surface 233 can cover or partially cover the plantar surface of the foot 14. In some cases, the inner surface 233 can be provided with a soft inner material, similar to the inner surface 215.

In some embodiments, the footplate 206 in combination with the lower support member 204 can enable toe 18 clearance as the foot 14 swings while walking, provide stability for the foot 14 and ankle joint 20, maintain neutral alignment and circumferential control of the foot 14, and/or smoothen knee to ankle motion while walking. In particular, the footplate 206 can be designed to restrict plantarflexion about the ankle joint. Accordingly, in some cases, the footplate 206 can be substantially flat while in other cases, the footplate 206 can follow the contour of a patient's footprint based on a 3D scan of the lower leg. Further, in some embodiments, the footplate 206 can include one or more raised walls at the heel-side, forming a heel cup designed to engage with the patient's heel 16. In some cases, the footplate 206 can include one or more raised walls designed to extend along the medial side of the foot 14 to provide additional arch support (see, e.g., raised walls 539A of FIGS. 19 to 23). In other cases, the footplate 206 can include one or more raised walls designed to extend along the lateral side of the foot 14.

In some embodiments, the footplate 206 includes a length 256 extending from about the heel 16 to about the toes 18

(see, e.g., FIG. 5) that can vary depending on the size and expected activity levels of the patient, severity of the lower leg injury, and comfort. In some cases, the length 256 can extend between the heel 16 to the toes 18 while in other cases, the length 256 can be increased or decreased to address patient-specific concerns. For example, the length 256 can be inset from the heel-side and toe-side edges of the foot by about at least 0.0 mm (e.g., no inset) to 3.0 mm, or about at least 1.0 mm to 4.0 mm, or about at least 2.0 mm to 5.0 mm, or about at least 3.0 mm to 6.0 mm, or about at least 4.0 mm to 7.0 mm, or about at least 5.0 mm to 8.0 mm, or about at least 6.0 mm to 9.0 mm, or about at least 7.0 mm to 10.0 mm, or about at least 8.0 mm to 11.0 mm, or about at least 9.0 mm to 12.0 mm, or about at least 10 mm to 13 mm, or about at least 11.0 mm to 14.0 mm, or about at least 12.0 mm to 15.0 mm to fit comfortably within a shoe, thereby optimizing foot coverage while allowing a patient to comfortably wear a shoe over the AFO 200.

Further, the footplate 206 includes a length 261 extending from about the medial side of the foot 14 to the lateral side of the foot 14 (see, e.g., FIG. 7), and which can be similarly inset as length 256. Thus, the footplate 206 can selectively engage with a majority of the patient's footprint, thereby promoting a more balanced weight distribution and providing a solid foundation for improved gait mechanics. Additionally, the footplate 206 can include a relatively low profile design such that a patient need not wear larger shoes to accommodate the AFO 200.

In some cases, the footplate 206 can be provided with a dynamic thickness 266 (see, e.g., FIG. 8) that includes a varyingly distributed added thickness to the baseline thickness of the AFO 200 such that the outer surface 232 can at least partially include one or more structural bands that extend along the length 256 of the footplate 206 (on the outer surface 232) and/or portions of the lower support member 204, extending in the orientation of gait. For instance, the one or more structural bands can include medial and lateral edge structural bands 221A, 221B (see, e.g., FIGS. 1A, 1B) and/or gait-oriented structural bands 236 (see, e.g., FIG. 1E). In this way, the footplate 206 can comprise varying thicknesses to substantially match certain portions of the patient's foot 14, thereby balancing the weight distribution of the AFO 200 between the footplate 206 and the upper support member 202. In certain embodiments, increased material thickness can be oriented towards the inner surface 233 such that the material can "push up" against the plantar surface of the foot 14. In this way, the footplate 206 can be designed to at least partially counterbalance arch collapse experienced by the patient. Overall, the gait-oriented structural bands 236 can strategically increase stiffness/rigidity in the footplate 206 to provide resistance against plantarflexion, without adding increased thickness to the overall profile of the foot 14. This may reduce material weight of the AFO 200 and enable at least some flexibility, thereby allowing the footplate 206 to bend during gait.

In some embodiments, the anterior plate 208 includes an overall shape that can substantially conform to the shape of at least an anterior portion of the patient's lower leg 10 (e.g., the shin 13), such that an outer surface 238 generally faces away from the patient and an inner surface 240 selectively engages with the shin 13. The outer surface 238 can comprise a durable material to protect and support the shin 13 or ankle joint 20, similar to the outer surface 214. In other embodiments, only certain portions of outer surface 238 may comprise a durable material without departing from the principles of this disclosure. The inner surface 240 can be provided with a soft inner material to enhance patient comfort, similar to the inner surface 215.

Further, the anterior plate 208 can provide additional stability to the lower leg 10 when the AFO 200 is in use. If included, the dimensions, shape, and positioning of the anterior plate 208 on the underlying patient anatomy can vary depending on the size and expected activity levels of the patient and injury type. In some embodiments, the anterior plate 208 can be positioned at about the shin-area of the patient to allow movement and bend about the ankle joint. The one or more attachment members 210, 212 can be used to secure the anterior plate 208 to the patient via one or more attachment slots 242 positioned on the anterior plate 208. In other embodiments, the anterior plate 208 can be positioned at the anterior portion of the ankle joint 20 to restrict bend and movement (e.g., dorsiflexion) about the ankle joint.

Figure 39:
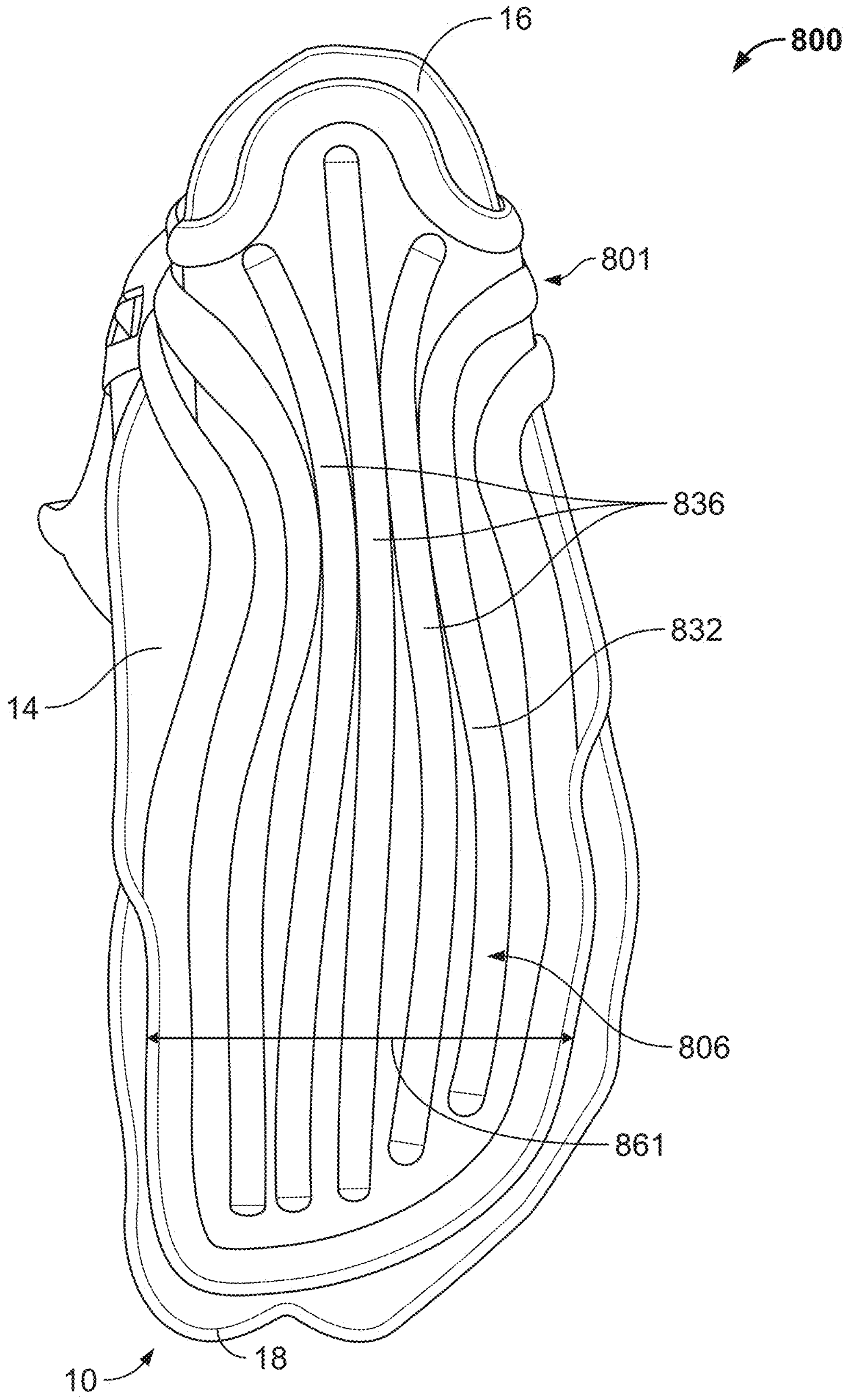
FIG. 39 is a bottom view of the AFO of FIG. 35.
Figure 40:
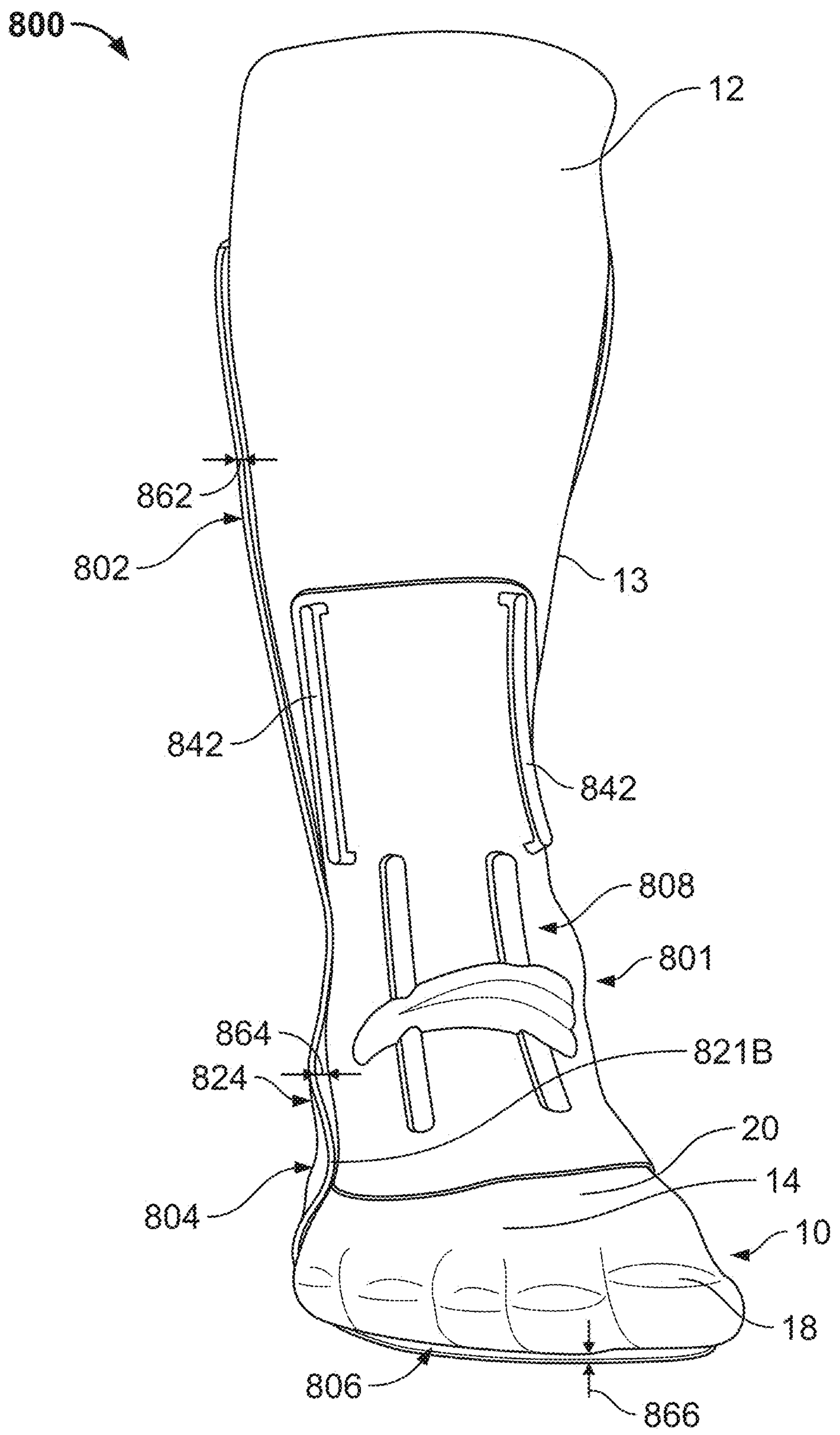
FIG. 40 is an anterior view of the AFO of FIG. 35.
Figure 41:
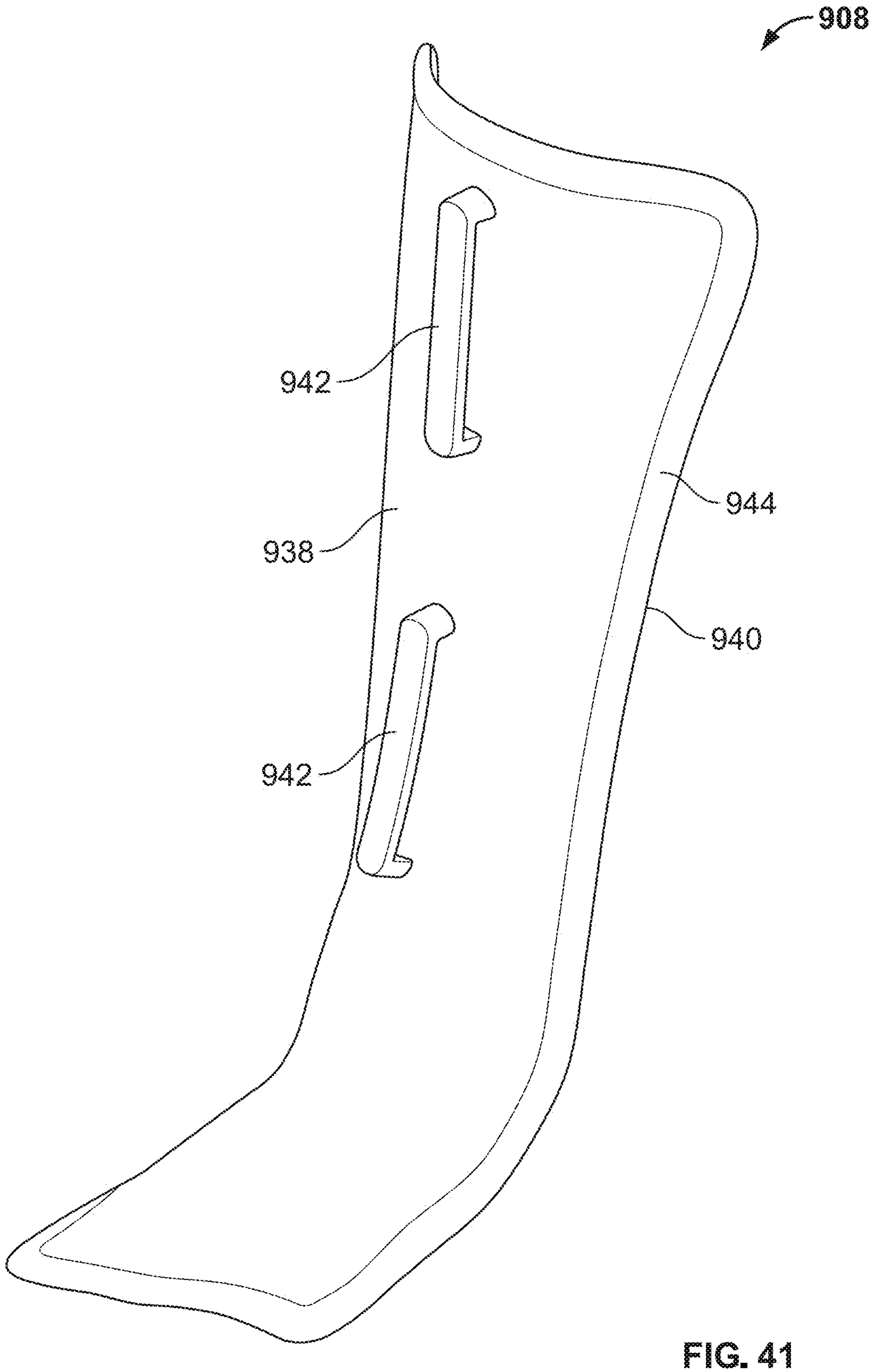
FIG. 41 is an anterior perspective view of an exemplary anterior plate, according to one embodiment.

In alternative embodiments, the size of the anterior plate 208 can be increased to cover a larger surface area of the lower leg 10, similar to a walking boot (see, e.g., FIGS. 39 to 41). For instance, the anterior plate 208 can include a length 258 that that can vary depending on the size and expected activity levels of the patient, severity of the lower leg injury, and comfort. Further, the anterior plate 208 can be provided with a dynamic thickness (not shown) that includes a varyingly distributed added thickness to the baseline thickness of the AFO 200 such that the outer surface 238 can at least partially include one or more structural bands that extend around a perimeter of the anterior plate 208. For instance, the one or more structural bands can include outer perimeter structural bands 244, similar to the outer perimeter bands 229 of the upper support member 202 (see, e.g., FIG. 1C).

In one non-limiting example, the AFO 200 can be beneficial to treat lower leg issues such as (but not limited to) foot drop via a low profile, low bulk alternative to other ankle-foot orthotics. However, although the embodiment shown with reference to FIGS. 2-8 includes certain components and features, the principles of this disclosure may extend to AFOs having different or altered components, features, shapes, and/or dimensions. Depending on patient-specific needs and patient anatomy type, various alternate embodiments are contemplated herein, such as, but not limited to, additional AFOs with different dimensions (e.g., thicknesses), arrangements of structural bands, placement (or omission) of certain components (e.g., upper support member, lower support member, footplate, anterior plate, attachment members), and pattern and sizing of ventilation holes in accordance with the principles of this disclosure. Depending on the length of the upper and lower support members, baseline thickness, and thickness variations imparted by the one or more structural bands, the AFOs can provide varying amounts of energy storing and energy return during gate. For instance, a smaller/shorter AFO can generate less energy return than a larger/longer AFO. Accordingly, additional exemplary embodiments of the AFO are discussed herein.

FIGS. 9-13 show another exemplary AFO 300. Similar to the AFO 200 of FIGS. 2-8, this embodiment includes a body 301 designed to substantially conformally engage with the lower leg 10 of a patient. The body 301 includes an upper support member 302, a lower support member 304, and a footplate 306.

In some embodiments, the upper support member 302 can substantially conform to and selectively engage with a portion of the patient's calf 12. The upper support member 302 includes an outer surface 314 that generally faces away from the patient and an inner surface 315 that selectively engages with the calf 12.

In some embodiments, the upper support member 302 includes a plurality of through-holes extending between the outer surface 314 and the inner surface 315, provided in the form of one or more attachment openings 318. In some cases, the one or more attachment openings 318 can receive the one or more attachment members (not shown) such that the one or more attachment members can be wrapped around portions of the lower leg 10 to adjustably secure the upper support member 302 to the lower leg 10. In some embodiments, the upper support member 302 can include an additional plurality of through-hole openings extending between the outer surface 314 and the inner surface 315, provided in the form one or more ventilation holes 316.

In some embodiments, the upper support member 302 includes a length 350 that can vary depending on patient-specific and pathology-specific considerations. Further, the upper support member 302 can be provided with a dynamic thickness (not shown) that includes a varyingly distributed added thickness to the baseline thickness of the AFO 300 such that the outer surface 314 can at least partially include one or more structural bands as described herein.

In some embodiments, the lower support member 304 can substantially conform to and selectively engage with a portion of the patient's ankle joint 20. Further, the lower support member 304 includes an outer surface 322 that generally faces away from the patient and an inner surface 323 that selectively engages with the ankle joint 20.

In some cases, the lower support member 304 can be arranged such that the body 301 includes a through-hole provided in the form of a posterior opening 326, the posterior opening having a length 360 that can be increased or decreased relative to length 352. In some embodiments, the posterior opening 326 can include an increased edge thickness provided in the form of inner perimeter structural bands 328.

In some embodiments, the lower support member 304 includes a length 352 that can vary depending on patient-specific and pathology-specific considerations. Additionally, the lower support member 304 can be provided with a dynamic thickness (not shown) that includes a varyingly distributed added thickness to the baseline thickness of the AFO 300 such that the outer surface 322 can at least partially include one or more structural bands (as described herein) that extend between the upper support member 302 and the lower support member 304 to the footplate 306.

In some embodiments, the footplate 306 can substantially conform to and selectively engage with a bottom portion of the patient's foot 14 (spanning from about the heel 16 to about the toes 18). Further, the footplate 306 includes an outer surface 332 that generally faces away from the patient and an inner surface 333 that selectively engages with the plantar surface of the foot 14.

In some embodiments, the footplate 306 includes lengths 356, 361 that can vary depending on patient-specific and pathology-specific considerations. In some cases, the footplate 306 can be provided with a dynamic thickness (not shown) that includes a varyingly distributed added thickness to the baseline thickness of the AFO 300 such that the outer surface 332 can at least partially include one or more structural bands (as described herein) that extend along the length 356 of the footplate 306 (on the outer surface 232) and/or portions of the lower support member 304, extending in the orientation of gait.

In some embodiments, the upper support member 302, lower support member 304, and/or the footplate 306 of the AFO 300 can include one or more structural bands, such as gait-oriented structural bands 336, medial and lateral edge structural bands 321A-B, inner and outer perimeter structural bands 328, 329, and upper and lower crossing structural bands 320, 330.

In one non-limiting example, it may be desirable for a patient to use this embodiment of the AFO 300 in light to moderately severe cases of foot drop, wherein the patient retains the ability to move the foot side to side.

FIGS. 14-18 show another exemplary AFO 400. Similar to the AFO 300 of FIGS. 9-13, this embodiment includes a body 401 designed to substantially conformally engage with the lower leg 10 of a patient. The body 401 includes an upper support member 402, a lower support member 404, and a footplate 406.

In some embodiments, the upper support member 402 can substantially conform to and selectively engage with a portion of the patient's calf 12. The upper support member 402 includes an outer surface 414 that generally faces away from the patient and an inner surface 415 that selectively engages with the calf 12.

In some embodiments, the upper support member 402 includes a plurality of through-holes extending between the outer surface 414 and the inner surface 415, provided in the form of one or more attachment openings 418. In some cases, the one or more attachment openings 418 can receive the one or more attachment members (not shown) such that the one or more attachment members can be wrapped around portions of the lower leg 10 to adjustably secure the upper support member 402 to the lower leg 10. In some embodiments, the upper support member 402 can include an additional plurality of through-hole openings extending between the outer surface 414 and the inner surface 415, provided in the form one or more ventilation holes (not shown).

In some embodiments, the upper support member 402 includes a length 450 that can vary depending on patient-specific and pathology-specific considerations. In particular, a length of the upper support member 402 can be reduced compared to AFO 300. Further, the upper support member 402 can be provided with a dynamic thickness (not shown) that includes a varyingly distributed added thickness to the baseline thickness of the AFO 400 such that the outer surface 414 can at least partially include one or more structural bands as described herein.

In some embodiments, the lower support member 404 can substantially conform to and selectively engage with a portion of the patient's ankle joint 20. Further, the lower support member 404 includes an outer surface 422 that generally faces away from the patient and an inner surface 423 that selectively engages with the ankle joint 20.

In some cases, the lower support member 404 can be arranged such that the body 401 includes a through-hole provided in the form of a posterior opening 426, the posterior opening having a length 460 that can be increased or decreased relative to length 452. In some embodiments, the posterior opening 426 can include an increased edge thickness provided in the form of inner perimeter structural bands 428.

In some embodiments, the lower support member 404 includes a length 452 that can vary depending on patient-specific and pathology-specific considerations. Additionally, the lower support member 404 can be provided with a dynamic thickness (not shown) that includes a varyingly distributed added thickness to the baseline thickness of the AFO 400 such that the outer surface 422 can at least partially include one or more structural bands (as described herein) that extend between the upper support member 402 and the lower support member 404 to the footplate 406.

In some embodiments, the footplate 406 can substantially conform to and selectively engage with a bottom portion of the patient's foot 14 (spanning from about the heel 16 to about the toes 18). Further, the footplate 406 includes an outer surface 432 that generally faces away from the patient and an inner surface 433 that selectively engages with the plantar surface of the foot 14.

In some embodiments, the footplate 406 includes lengths 456, 461 that can vary depending on patient-specific and pathology-specific considerations. In some cases, the footplate 406 can be provided with a dynamic thickness (not shown) that includes a varyingly distributed added thickness to the baseline thickness of the AFO 400 such that the outer surface 432 can at least partially include one or more structural bands (as described herein) that extend along the length 456 of the footplate 406 (on the outer surface 232) and/or portions of the lower support member 404, extending in the orientation of gait.

In some embodiments, the upper support member 402, lower support member 404, and/or the footplate 406 of the AFO 400 can include one or more structural bands, such as gait-oriented structural bands 436, medial and lateral edge structural bands 421A-B, inner and outer perimeter structural bands 428, 429, and upper and lower crossing structural bands 420, 430.

FIGS. 19-23 show another exemplary AFO 500. Similar to the AFO 300 of FIGS. 1-7, this embodiment includes a body 501 designed to substantially conformally engage with the lower leg 10 of a patient. The body 501 includes an upper support member 502, a lower support member 504, and an "extended" footplate 506.

In some embodiments, the upper support member 502 can substantially conform to and selectively engage with a portion of the patient's calf 12. The upper support member 502 includes an outer surface 514 that generally faces away from the patient and an inner surface 515 that selectively engages with the calf 12.

In some embodiments, the upper support member 502 includes a plurality of through-holes extending between the outer surface 514 and the inner surface 515, provided in the form of one or more attachment openings 518. In some cases, the one or more attachment openings 518 can receive the one or more attachment members (not shown) such that the one or more attachment members can be wrapped around portions of the lower leg 10 to adjustably secure the upper support member 502 to the lower leg 10. In some embodiments, the upper support member 502 can include an additional plurality of through-hole openings extending between the outer surface 514 and the inner surface 515, provided in the form one or more ventilation holes 516.

In some embodiments, the upper support member 502 includes a length 550 that can vary depending on patient-specific and pathology-specific considerations. Further, the upper support member 502 can be provided with a dynamic thickness (not shown) that includes a varyingly distributed added thickness to the baseline thickness of the AFO 500 such that the outer surface 514 can at least partially include one or more structural bands as described herein.

In some embodiments, the lower support member 504 can substantially conform to and selectively engage with a portion of the patient's ankle joint 20. Further, the lower support member 504 includes an outer surface 522 that generally faces away from the patient and an inner surface 523 that selectively engages with the ankle joint 20.

In some cases, the lower support member 504 can be arranged such that the body 501 includes a through-hole provided in the form of a posterior opening 526, the posterior opening having a length 560 that can be increased or decreased relative to length 552. In some embodiments, the posterior opening 526 can include an increased edge thickness provided in the form of inner perimeter structural bands 528.

In some embodiments, the lower support member 504 includes a length 552 that can vary depending on patient-specific and pathology-specific considerations. Additionally, the lower support member 504 can be provided with a dynamic thickness (not shown) that includes a varyingly distributed added thickness to the baseline thickness of the AFO 500 such that the outer surface 522 can at least partially include one or more structural bands (as described herein) that extend between the upper support member 502 and the lower support member 504 to the footplate 506.

In some embodiments, the footplate 506 can substantially conform to and selectively engage with a bottom portion of the patient's foot 14 (spanning from about the heel 16 to about the toes 18). Further, the footplate 506 includes an outer surface 532 that generally faces away from the patient and an inner surface 533 that selectively engages with the plantar surface of the foot 14.

In this embodiment, the footplate 506 can include one or more raised walls provided in the form of a medial raised wall 539A and a lateral raised wall 539B, each extending vertically to provide additional coverage on the medial and lateral sides of the foot/midfoot while to further stabilizing the ankle-foot complex. In this way, a desired level of ground force reaction can be achieved to support gait biomechanics of gait while allowing the AFO 500 to remain relatively low profile.

In some embodiments, the footplate 506 includes lengths 556, 561 that can vary depending on patient-specific and pathology-specific considerations. In some cases, the footplate 506 can be provided with a dynamic thickness (not shown) that includes a varyingly distributed added thickness to the baseline thickness of the AFO 500 such that the outer surface 532 can at least partially include one or more structural bands (as described herein) that extend along the length 556 of the footplate 506 (on the outer surface 532) and/or portions of the lower support member 504, extending in the orientation of gait.

In some embodiments, the upper support member 502, lower support member 504, and/or the footplate 506 of the AFO 500 can include one or more structural bands, such as gait-oriented structural bands 536, medial and lateral edge structural bands 521A-B, inner and outer perimeter structural bands 528, 529, and upper and lower crossing structural bands 520, 530.

In one non-limiting example, it may be desirable for a patient to use this embodiment of the AFO 500 for more severe cases of foot drop, ankle arthritis, or ankle sprains (e.g., high ankle sprains, chronic ankle sprains, acute ankle sprains), wherein side to side foot movement is restricted but the patient can still experience relatively normal/natural gait. Further, pressure at the heel area can be reduced. In another non-limiting example, it may be preferable for a patient to use this embodiment of the AFO 500 as an alternative to ankle fusion surgery.

FIGS. 24-29 show another exemplary AFO 600. Similar to the AFO 500 of FIGS. 19-23, this embodiment includes a body 601 designed to substantially conformally engage with the lower leg 10 of a patient. The body 601 includes an upper support member 602, a lower support member 604, and an "extended" footplate 606. In some embodiments, AFO 600 can further include an anterior plate 608.

In some embodiments, the upper support member 602 can substantially conform to and selectively engage with a portion of the patient's calf 12. The upper support member 602 includes an outer surface 614 that generally faces away from the patient and an inner surface 615 that selectively engages with the calf 12.

In some embodiments, the upper support member 602 includes a plurality of through-holes extending between the outer surface 614 and the inner surface 615, provided in the form of one or more attachment openings 618. In some cases, the one or more attachment openings 618 can receive the one or more attachment members (not shown) such that the one or more attachment members can be wrapped around portions of the lower leg 10 to adjustably secure the upper support member 602 to the lower leg 10. In some embodiments, the upper support member 602 can include an additional plurality of through-hole openings extending between the outer surface 614 and the inner surface 615, provided in the form one or more ventilation holes 616.

In some embodiments, the upper support member 602 includes a length 650 that can vary depending on patient-specific and pathology-specific considerations. Further, the upper support member 602 can be provided with a dynamic thickness 662 that includes a varyingly distributed added thickness to the baseline thickness of the AFO 600 such that the outer surface 614 can at least partially include one or more structural bands as described herein.

In some embodiments, the lower support member 604 can substantially conform to and selectively engage with a portion of the patient's ankle joint 20. Further, the lower support member 604 includes an outer surface 622 that generally faces away from the patient and an inner surface 623 that selectively engages with the ankle joint 20.

In some cases, the lower support member 604 can be arranged such that the body 601 includes a through-hole provided in the form of a posterior opening 626, the posterior opening having a length 660 that can be increased or decreased relative to length 652. In some embodiments, the posterior opening 626 can include an increased edge thickness provided in the form of inner perimeter structural bands 628.

In some embodiments, the lower support member 604 includes a length 652 that can vary depending on patient-specific and pathology-specific considerations. Additionally, the lower support member 604 can be provided with a dynamic thickness 664 that includes a varyingly distributed added thickness to the baseline thickness of the AFO 600 such that the outer surface 622 can at least partially include one or more structural bands (as described herein) that extend between the upper support member 602 and the lower support member 604 to the footplate 606.

In some embodiments, the footplate 606 can substantially conform to and selectively engage with a bottom portion of the patient's foot 14 (spanning from about the heel 16 to about the toes 18). Further, the footplate 606 includes an outer surface 632 that generally faces away from the patient and an inner surface 633 that selectively engages with the plantar surface of the foot 14.

In this embodiment, the footplate 606 can include one or more raised walls provided in the form of a medial raised wall 639A and a lateral raised wall 639B, each extending vertically to support additional portions of the foot/midfoot, and additional material thickness/spacing can be concentrated at portions of the footplate 606 engaging with the patient's foot arch. The amount of material thickness and spacing can be determined via 3D-scanning the patient in a semi-weight bearing position.

In some embodiments, the footplate 606 includes lengths 656, 661 that can vary depending on patient-specific and pathology-specific considerations. In some cases, the footplate 606 can be provided with a dynamic thickness 666 that includes a varyingly distributed added thickness to the baseline thickness of the AFO 600 such that the outer surface 632 can at least partially include one or more structural bands (as described herein) that extend along the length 656 of the footplate 606 (on the outer surface 632) and/or portions of the lower support member 604, extending in the orientation of gait.

In some embodiments, the anterior plate 608 can substantially conform to and selectively engage with an anterior portion of the patient's lower leg 10 to restrict dorsiflexion. The anterior plate 608 includes an outer surface 638 that generally faces away from the patient and an inner surface 640 that selectively engages with the shin 13. In some embodiments, the one or more attachment members can be used to secure the anterior plate 608 to the patient via one or more attachment slots 642 positioned on the anterior plate 608.

In some embodiments, the upper support member 602, lower support member 604, and/or the footplate 606 of the AFO 600 can include one or more structural bands, such as gait-oriented structural bands 636, medial and lateral edge structural bands 621A-B, inner and outer perimeter structural bands 628, 629, and upper and lower crossing structural bands 620, 630.

In one non-limiting example, it may be desirable for a patient to use this embodiment of the AFO 600 for severe cases of foot drop or PTTD/PTTI, wherein side to side foot movement is restricted and pressure at the ankle is reduced. This may relieve and prevent further arch collapse.

FIGS. 30-34 show another exemplary AFO 700. Similar to the AFO 500 of FIGS. 1-7, this embodiment includes a body 701 designed to substantially conformally engage with the lower leg 10 of a patient. The body 701 includes an upper support member 702, a lower support member 704, and an "extended" footplate 706.

In some embodiments, the upper support member 702 can substantially conform to and selectively engage with a portion of the patient's calf 12. The upper support member 702 includes an outer surface 714 that generally faces away from the patient and an inner surface 715 that selectively engages with the calf 12.

In some embodiments, the upper support member 702 includes a plurality of through-holes extending between the outer surface 714 and the inner surface 715, provided in the form of one or more attachment openings 718. In some cases, the one or more attachment openings 718 can receive the one or more attachment members (not shown) such that the one or more attachment members can be wrapped around portions of the lower leg 10 to adjustably secure the upper support member 702 to the lower leg 10. In some embodiments, the upper support member 702 can include an additional plurality of through-hole openings extending between the outer surface 714 and the inner surface 715, provided in the form one or more ventilation holes (not shown).

In some embodiments, the upper support member 702 includes a length 750 that can vary depending on patient-specific and pathology-specific considerations. In particular, a length of the upper support member 702 can be reduced compared to AFO 500. Further, the upper support member 702 can be provided with a dynamic thickness (not shown) that includes a varyingly distributed added thickness to the baseline thickness of the AFO 700 such that the outer surface 714 can at least partially include one or more structural bands as described herein.

In some embodiments, the lower support member 704 can substantially conform to and selectively engage with a portion of the patient's ankle joint 20. Further, the lower support member 704 includes an outer surface 722 that generally faces away from the patient and an inner surface 723 that selectively engages with the ankle joint 20.

In some cases, the lower support member 704 can be arranged such that the body 701 includes a through-hole provided in the form of a posterior opening 726, the posterior opening having a length 760 that can be increased or decreased relative to length 752. In some embodiments, the posterior opening 726 can include an increased edge thickness provided in the form of inner perimeter structural bands 728.

In some embodiments, the lower support member 704 includes a length 752 that can vary depending on patient-specific and pathology-specific considerations. Additionally, the lower support member 704 can be provided with a dynamic thickness (not shown) that includes a varyingly distributed added thickness to the baseline thickness of the AFO 700 such that the outer surface 722 can at least partially include one or more structural bands (as described herein) that extend between the upper support member 702 and the lower support member 704 to the footplate 706.

In some embodiments, the footplate 706 can substantially conform to and selectively engage with a bottom portion of the patient's foot 14 (spanning from about the heel 16 to about the toes 18). Further, the footplate 706 includes an outer surface 732 that generally faces away from the patient and an inner surface 733 that selectively engages with the plantar surface of the foot 14. In this embodiment, the footplate 706 can include one or more raised walls provided in the form of a medial raised wall 739A and a lateral raised wall 739B, each extending vertically to cover additional portions of the foot/midfoot while allowing the AFO 700 to remain relatively low profile.

In some embodiments, the footplate 706 includes lengths 756, 761 that can vary depending on patient-specific and pathology-specific considerations. In some cases, the footplate 706 can be provided with a dynamic thickness (not shown) that includes a varyingly distributed added thickness to the baseline thickness of the AFO 700 such that the outer surface 732 can at least partially include one or more structural bands (as described herein) that extend along the length 756 of the footplate 706 (on the outer surface 732) and/or portions of the lower support member 704, extending in the orientation of gait.

In some embodiments, the upper support member 702, lower support member 704, and/or the footplate 706 of the AFO 700 can include one or more structural bands, such as gait-oriented structural bands 736, medial and lateral edge structural bands 721A-B, inner and outer perimeter structural bands 728, 729, and upper and lower crossing structural bands 720, 730.

Thus, in one non-limiting example, AFO 700 can provide dynamic bracing and increased stability to the ankle joint by moderately limiting ankle motion and side to side foot movement.

FIGS. 35-40 show another exemplary AFO 800. Similar to the AFO 200 of FIGS. 2-8, this embodiment includes a body 801 designed to substantially conformally engage with the lower leg 10 of a patient. The body 801 includes an upper support member 802, a lower support member 804, and a footplate 806. In some embodiments, AFO 800 can further include an anterior plate 808.

In some embodiments, the upper support member 802 can substantially conform to and selectively engage with a portion of the patient's calf 12. The upper support member 802 includes an outer surface 814 that generally faces away from the patient and an inner surface 815 that selectively engages with the calf 12.

In some embodiments, the upper support member 802 includes a plurality of through-holes extending between the outer surface 814 and the inner surface 815, provided in the form of one or more attachment openings 818. In some cases, the one or more attachment openings 818 can receive the one or more attachment members (not shown) such that the one or more attachment members can be wrapped around portions of the lower leg 10 to adjustably secure the upper support member 802 to the lower leg 10. In some embodiments, the upper support member 802 can include an additional plurality of through-hole openings extending between the outer surface 814 and the inner surface 815, provided in the form one or more ventilation holes 816.

In some embodiments, the upper support member 802 includes a length 850 that can vary depending on patient-specific and pathology-specific considerations. Further, the upper support member 802 can be provided with a dynamic thickness 862 that includes a varyingly distributed added thickness to the baseline thickness of the AFO 800 such that the outer surface 814 can at least partially include one or more structural bands as described herein.

In some embodiments, the lower support member 804 can substantially conform to and selectively engage with a portion of the patient's ankle joint 20. Further, the lower support member 804 includes an outer surface 822 that generally faces away from the patient and an inner surface 823 that selectively engages with the ankle joint 20.

In some cases, the lower support member 804 can be arranged such that the body 801 includes a through-hole provided in the form of a posterior opening 826, the posterior opening having a length 860 that can be increased or decreased relative to length 852. In some embodiments, the posterior opening 826 can include an increased edge thickness provided in the form of inner perimeter structural bands 828.

In some embodiments, the lower support member 804 includes a length 852 that can vary depending on patient-specific and pathology-specific considerations. Additionally, the lower support member 804 can be provided with a dynamic thickness 864 that includes a varyingly distributed added thickness to the baseline thickness of the AFO 800 such that the outer surface 822 can at least partially include one or more structural bands (as described herein) that extend between the upper support member 802 and the lower support member 804 to the footplate 806.

In some embodiments, the footplate 806 can substantially conform to and selectively engage with a bottom portion of the patient's foot 14 (spanning from about the heel 16 to about the toes 18). Further, the footplate 806 includes an outer surface 832 that generally faces away from the patient and an inner surface 833 that selectively engages with the plantar surface of the foot 14.

In this embodiment, the footplate 806 can include one or more raised walls provided in the form of a medial raised wall 839A and a lateral raised wall 839B, each extending vertically to support additional portions of the foot/midfoot, and additional material thickness/spacing can be concentrated at portions of the footplate 606 engaging with the patient's foot arch.

In some embodiments, the footplate 806 includes lengths 856, 861 that can vary depending on patient-specific and pathology-specific considerations. In some cases, the footplate 806 can be provided with a dynamic thickness 866 that includes a varyingly distributed added thickness to the baseline thickness of the AFO 800 such that the outer surface 832 can at least partially include one or more structural bands (as described herein) that extend along the length 856 of the footplate 806 (on the outer surface 832) and/or portions of the lower support member 804, extending in the orientation of gait.

In some embodiments, the anterior plate 808 can substantially conform to and selectively engage with an anterior portion of the patient's lower leg 10 to restrict dorsiflexion. The anterior plate 808 includes an outer surface 838 that generally faces away from the patient and an inner surface 840 that selectively engages with the shin 13. In some embodiments, the one or more attachment members can be used to secure the anterior plate 808 to the patient via one or more attachment slots 842 positioned on the anterior plate 808.

Figure 42:
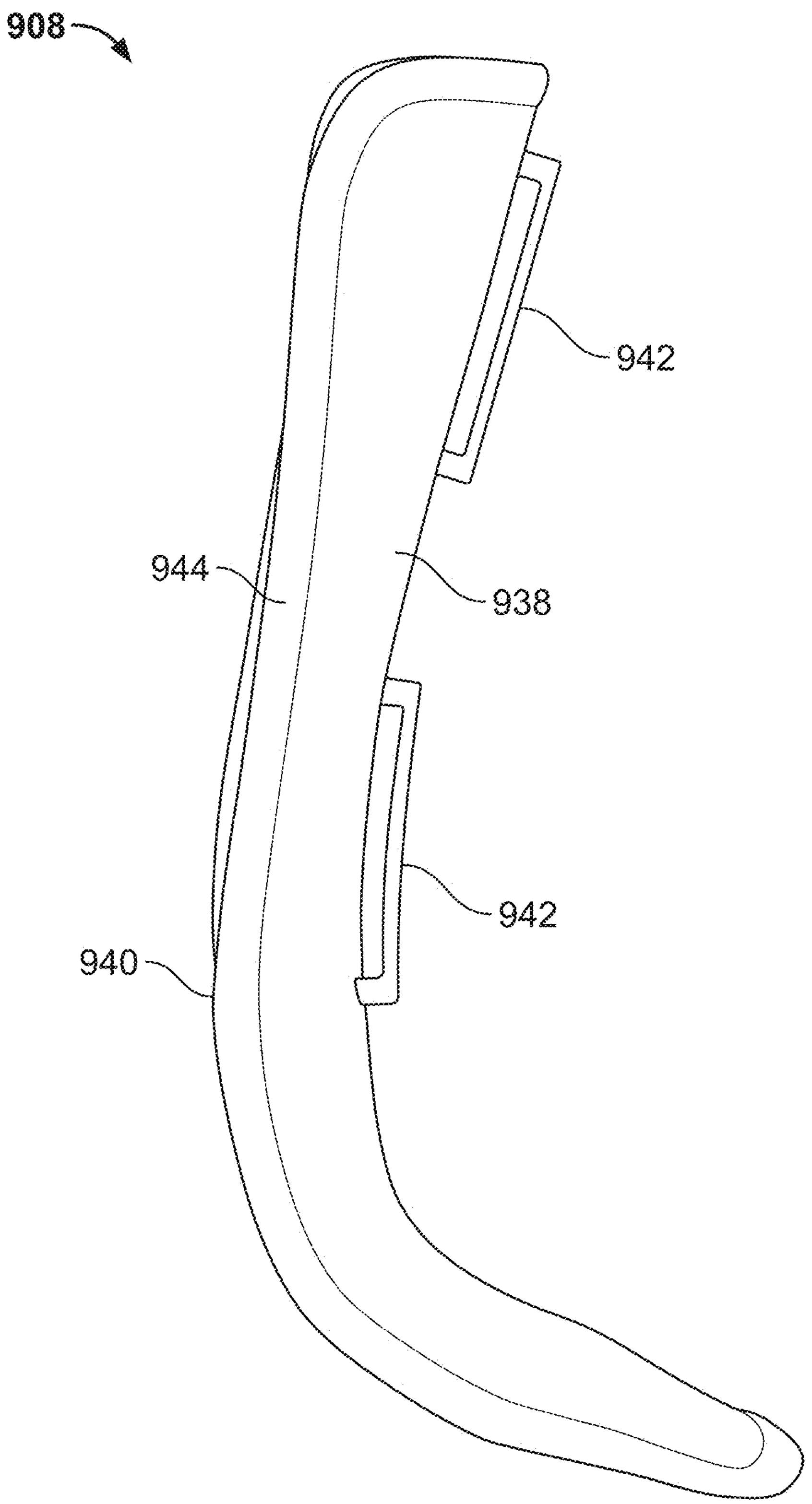
FIG. 42 is a lateral side view of the anterior plate of FIG. 41.
Figure 43:
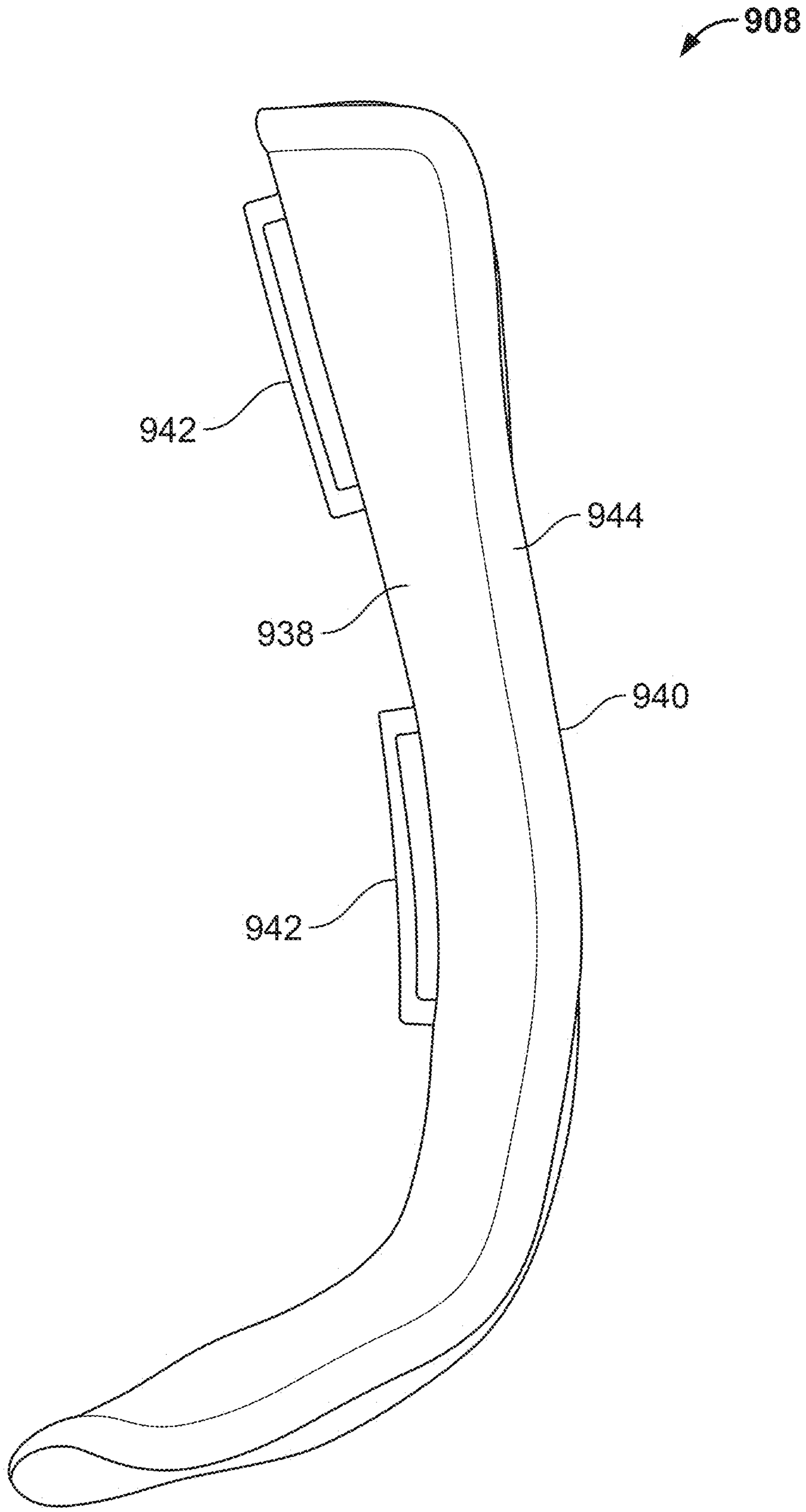
FIG. 43 is a medial side view of the anterior plate of FIG. 41.

In the embodiment shown, the anterior plate 808 includes a relatively shorter length as compared to the body 801. In other embodiments, the anterior plate can include a relatively longer length. For instance, with additional reference to FIGS. 41 to 43, a different embodiment of an anterior plate 908 can be used in place of anterior plate 808, wherein the anterior plate 908 can provide increased coverage to anterior portions of the lower leg 10. Like anterior plate 808, anterior plate 908 includes an outer surface 938 that generally faces away from the patient and an inner surface 940 that selectively engages with the shin 13. Anterior plate 908 may further include an optional structural band 944 disposed around a perimeter of the anterior plate to provide stiffness, if desired. In some embodiments, the one or more attachment members can be used to secure the anterior plate 908 to the patient via one or more attachment slots 942 positioned on the anterior plate.

In some embodiments, the upper support member 802, lower support member 804, and/or the footplate 806 of the AFO 800 can include one or more structural bands, such as gait-oriented structural bands 836, medial and lateral edge structural bands 821A-B, inner and outer perimeter structural bands 828, 829, and upper and lower crossing structural bands 820, 830.

In one non-limiting example, it may be desirable for a patient to use this embodiment of the AFO 800 in cases of post-operative treatment after ankle surgery or any other condition in which ankle immobilization is desired. In particular, the increased baseline thickness for the body, added thickness variations via the one or more structural bands, and positioning of the anterior plate 808 may improve immobilization of the ankle joint 20 while the patient recovers from ankle surgery or other ankle injury. In this way, the AFO 800 can serve as a relatively low profile alternative to a bulky walking boot. In another non-limiting example, as a patient heals from ankle surgery or other severe ankle injury, it may be desirable to remove the anterior plate 808 or alter its placement to a different area on the lower leg 10 to allow improved dorsiflexion about the ankle joint 20. In this way, the AFO 800 can provide a dynamic brace for the ankle as it heals, thereby improving recovery time.

According to some embodiments, one or more components of the AFO (e.g., AFOs 200, 300, 400, 500, 600, 700, 800, or any other suitable AFO) can be produced or manufactured based on 3D-imaging techniques to treat a lower leg condition of the patient. In some cases, the one or more components of the AFO can be designed according to patient-specific and/or pathology-specific considerations.

Some non-limiting examples of conditions that may be treated using an AFO include but are not limited to, drop foot, ankle arthritis, posterior tibial tendon dysfunction (PTTD) or inefficiency, Achilles repair or Achilles tendonitis, post-operation immobilization, and ankle sprain or other ankle ligament injuries. In some non-limiting examples, such as PTTD, an AFO designed and produced in accordance with the principles of this disclosure may be designed to fit a patient deformity, which may prevent further arch collapse and unload the joints in the patient's ankle and foot through gait, thereby reducing pain.

In other non-limiting examples, an AFO designed and produced in accordance with the principles of this disclosure may be used to treat Achilles conditions where the AFO reduces forces felt by the injured tendon. In Achilles treatments, it may be necessary to scan a patient's anatomy at a "neutral" ankle angle. Current treatment methods may include using a wedge to position the patient's foot at varying angles of plantarflexion to unload the Achilles prior to orienting the patient's anatomy at a neutral ankle angle. An AFO designed in accordance with the principles of this disclosure may increase a patient's activity level in a safe way, giving the patient confidence in their recovery process.

In yet another example, an AFO designed in accordance with the principles of this disclosure can be used for post-operative immobilization. In that case, an existing treatment plan of a splinting, bracing, and/or casting process may first involve a post-op splint designed to protect the wound sites for approximately two weeks, and then transition to a cast or walking boot for approximately an additional 4-8 weeks. Here, the patient may be able to transition to a patient-specific AFO with the 3D scan strategically taken sometime earlier in the process, and possibly even a scan taken of the contralateral anatomy if significant swelling is present. In some instances, the patient may be near-fully immobilized with the AFO for 2-6 weeks, and, when cleared, can remove the anterior plate to continue wearing the AFO. This may allow for controlled mobility that can aid in the recovery process.

Figure 44:
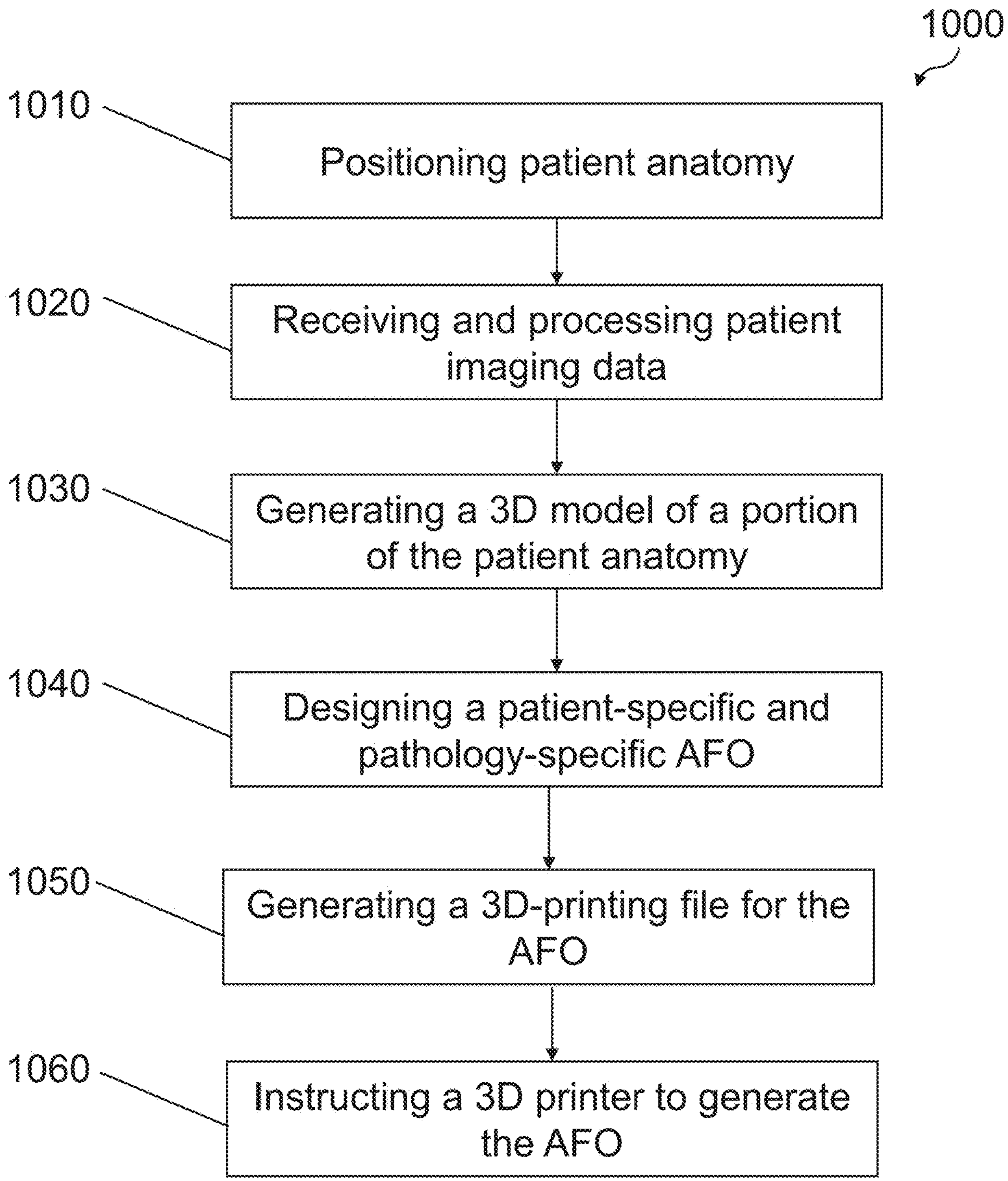
FIG. 44 is a flowchart of an AFO manufacturing process, according to one embodiment.

Referring now to FIG. 44, one method 1000 for designing and producing a patient-specific AFO in accordance with the principles of this disclosure generally includes: (1) positioning the patient anatomy 1010; (2) receiving and processing patient imaging data 1020; (3) generating a 3D model of a patient lower leg to be stabilized 1030; (4) designing a patient-specific AFO based on the 3D model and the pathology to be treated 1040; (5) generating a file for 3D-printing the patient-specific AFO 1050; and (6) instructing a 3D printer to generate the patient-specific AFO in one or more components 1060. Further manufacturing may include using/attaching one or more attachment members, and using/attaching one or more soft materials to the inner surfaces of the components of the AFO.

In some embodiments, step 1010 can optionally occur while the patient is sitting in a non-weight bearing or semi-weight bearing position. For instance, in one non-limiting case, the patient can sit on a table to achieve a desirable alignment for scanning, such that the knee extends perpendicularly from the table and the foot extends perpendicularly from the knee. In this way, the foot can rest on a platform having a solid surface such that the calf and the rest of the foot are perpendicularly or approximately perpendicularly aligned (e.g., the knee is directly above the ankle) and the foot rests in a semi-weight bearing position. In other instances, scanning the patient can be done in any suitable position. In some embodiments, the platform can be glass or any other transparent material. In some embodiments, the platform can be relatively flat while in other embodiments, the platform can include a raised topography designed to partially conform with the plantar surface of the patient foot. In other cases, the platform can be flat but oriented at an angle towards the patient.

In some embodiments, step 1020 involves using a 3D-scanner to scan the top of the foot, including side portions of the arch. In certain embodiments, the 3D-scanner can be a portable user device, wherein a clinician can manually scan the patient anatomy by orienting the 3D-scanner around the patient's lower leg as it rests on the platform. It may be desirable to conduct a 3D-scan while the foot is in a weight-bearing position in order to more accurately capture arch data. However, in another non-limiting case, the patient can extend the foot towards the 3D-scanner for scanning and without resting the foot on a surface. In another non-limiting case, the patient can extend the lower leg into a larger device configured for 3D-scanning. In cases of flexible deformities, a clinician may "stretch" the foot (e.g., via "posting" the heel) to achieve a perpendicular or approximately perpendicular position for scanning. In cases of rigid deformities, the patient foot can be scanned in a deformed position.

In some embodiments, step 1030 can involve rendering a 3D model of the scanned patient lower leg. In particular, based on the scanned or selected patient anatomy used as a reference, a 3D-scanning algorithm can digitally "recreate" (e.g., extrapolate, render) other portions of patient anatomy based on the reference. Thus, in one non-limiting example, an algorithm can digitally recreate the arch and the plantar surface of the foot of the 3D model based on a scan of the top of the patient foot (the reference) and the planar surface of the platform. In some cases, the algorithm may truncate a portion of the reference scan prior to extrapolating one or more angles indicative of the patient foot arch.

In some embodiments, step 1040 can involve designing a patient-specific AFO based, in part, on the outcome of step 1030. In some cases, a digital fabrication software can be used to design the patient-specific AFO. Additionally, in some cases, designing the patient-specific AFO can be based on the particular pathology, lower leg issue, or other deformity suffered by the patient. In one non-limiting example, a patient having light to moderate footdrop may require AFO 200 or AFO 300 adapted to their specific anatomy via step 1030. In another non-limiting example, an active patient having chronic ankle issues may require AFO 400 or 700 adapted to their specific anatomy via step 1030. In another non-limiting example, a patient having severe foot drop, ankle/hindfoot arthritis, and/or PTTI/PTTD may require AFO 500 or 600 adapted to their specific anatomy via step 1030. In another non-limiting example, a patient healing from ankle surgery may require AFO 800 adapted to their specific anatomy via step 1030. In another non-limiting example, a heavier or more active patient may require an AFO having a relatively thick baseline thickness. Generally, it can be desirable to construct the AFO based on the deformity present such that certain features of the AFO can at least partially correct the deformity when worn by the patient. Thus, in any of the aforementioned non-limiting examples, adaption of the particular AFO can involve omission/inclusion of an anterior plate, patient-specific variations in base device thickness and structural band thickness/distribution, patient-specific variations in the inner surface of the footplate, and variations in ventilation hole arrangement, among other variation.

Further, in some embodiments, step 1040 can involve additional pre-planning, wherein the clinician can conduct a gap analysis to determine the amount of force required for the patient to exert to walk normally based on the amount of force the patient exerts without the assistance of an AFO or other device. Based on the gap analysis, the clinician can more particularly design the AFO prior to step 1040. For instance, a patient's measurements/characteristics (e.g., height, weight, activity level, etc.) and anatomical features can be used as input parameters for designing an AFO with desirable baseline thickness and variable thickness. In certain embodiments, method 1000 can yield a trial AFO such that the clinician can conduct a gait analysis with the patient wearing the trial AFO to determine whether the patient can exert an appropriate amount of force. Thus, method 1000 can be performed iteratively to yield the end patient-specific AFO.

In some embodiments, step 1050 can be an optional step.

In some embodiments, step 1060 can involve a clinician selecting a desirable material for 3D-printing the patient-specific AFO.

Although the embodiment shown herein is an ankle foot orthosis device, the principles of this disclosure may extend to AFOs with any number and placement of components designed to engage with any type of patient body parts. Various alternate embodiments are contemplated herein, such as, but not limited to, devices wherein the body of the AFO can extend in a spiral pattern around the patient lower leg. In other embodiments, the body of the AFO can extend to cover at least a portion of the knee such that the patient can wear a knee ankle-foot orthotic (KAFO). In certain embodiments, the body of the AFO can extend a relatively short distance to encompass the ankle area without encompassing the shin/calf area. Alternative embodiments further include AFOs designed to adjust in one or more dimensions. Depending on patient-specific needs and patient anatomy type, any such alternative embodiment may include any suitable number of components in accordance with the principles of this disclosure.

The invention claimed is:

1. A patient-specific ankle-foot orthotic (AFO), the AFO comprising:
- a body comprising:
  - an upper support member comprising:
    - a first outer surface and a first inner surface, the first inner surface designed to selectively engage with at least a portion of a patient's calf;
  - a lower support member comprising:
    - a second outer surface and a second inner surface, the second inner surface designed to selectively engage with at least a portion of the patient's ankle;
  - a footplate comprising:
    - a third outer surface and a third inner surface, the third inner surface designed to selectively engage with at least a portion of the patient's foot; and one or more structural bands disposed on portions of the first outer surface, second outer surface, and third outer surface, wherein a first structural band of the one or more structural bands is configured to extend in a horseshoe pattern about an upper portion of the patient's ankle between a medial side of the patient's ankle and a lateral side of the patient's ankle, the first structural band designed to improve energy transfer throughout the body by storing and returning a custom-tailored amount of energy during the patient's gait; and the design of the body based on a 3D model of the patient's lower leg, wherein the design of the body is patient-specific and pathology-specific.

2. The patient-specific AFO of claim 1, further comprising a baseline thickness of about 1.5 mm to 5.0 mm.

3. The patient-specific AFO of claim 2, wherein the one or more structural bands include a width of about 1.0 mm to 10.0 mm and contribute to an added thickness of about 0.5 mm to 5.0 mm to the baseline thickness.

4. The patient-specific AFO of claim 3, wherein the lower support member comprises one or more struts.

5. The patient-specific AFO of claim 4, wherein each of the one or more struts is angled by about 10.0 degrees to 40.0 degrees from vertical.

6. The patient-specific AFO of claim 3, wherein the upper support member includes one or more ventilation holes.

7. The patient-specific AFO of claim 3, wherein the upper support member includes at least one attachment opening.

8. The patient-specific AFO of claim 7, further comprising:

an anterior plate, the anterior plate comprising a fourth outer surface having at least one attachment slot and a fourth inner surface, the fourth inner surface designed to selectively engage with an anterior portion of the patient's lower leg.

9. The patient-specific AFO of claim 8, further comprising at least one attachment member designed to selectively engage with the at least one attachment opening and the at least one attachment slot.

10. The patient-specific AFO of claim 3, wherein the footplate comprises one or more raised walls.

11. The patient-specific AFO of claim 1, wherein the one or more structural bands are edge structural bands.

12. The patient-specific AFO of claim 1, wherein the one or more structural bands are peripheral structural bands.

13. The patient-specific AFO of claim 1, wherein the one or more structural bands are crossing structural bands.

14. The patient-specific AFO of claim 1, wherein the one or more structural bands are gait-oriented structural bands.

15. The patient-specific AFO of claim 8, wherein the body and the anterior plate are additively manufactured.

16. The patient-specific AFO of claim 1, wherein a second structural band of the one or more structural bands is configured to be aligned centrally with the patient's Achilles tendon, the second structural band configured to be at least partially extending from a base of the patient's third metatarsal and towards the patient's first toe such that the second structural band is oriented along a path of maximum pressure during the patient's gait.

17. A patient-specific ankle-foot orthotic (AFO), the AFO comprising:

an additively manufactured body, the design of the body based on a 3D model of the patient's lower leg, wherein the design of the body is patient-specific and pathology-specific, the body comprising:

an upper support member comprising:

a first outer surface and a first inner surface, the first inner surface designed to selectively engage with a portion of a patient's calf;

a lower support member comprising:

a second outer surface and a second inner surface, the second inner surface designed to selectively engage with a portion of the patient's ankle;

a footplate comprising:

a third outer surface and a third inner surface, the third inner surface designed to selectively engage with a portion of the patient's foot;

an anterior plate comprising:

a fourth outer surface having at least one attachment slots and a fourth inner surface, the fourth inner surface designed to selectively engage with an anterior portion of the patient's lower leg;

at least one attachment member designed to selectively engage with at least one attachment opening and the at least one attachment slots to secure the AFO to the patient's lower leg;

one or more structural bands disposed on portions of the first outer surface, second outer surface, and third outer surface; and a baseline thickness of about 1.5 mm to 5.0 mm, wherein the one or more structural bands include a width of about 1.0 mm to 10.0 mm and contribute to an added thickness of about 0.5 mm to 5.0 mm to the baseline thickness, and wherein a first structural band of the one or more structural bands is configured to extend in a horseshoe pattern about an upper portion of the patient's ankle between a medial side of the patient's ankle and a lateral side of the patient's ankle, the first structural band is at least partially gait-oriented and configured to extend along a plantar surface of the patient's foot, wherein the first structural band is designed to improve energy transfer throughout the body by storing and returning a custom-tailored amount of energy during the patient's gait.

* * * * *